(12) United States Patent
Bebbington et al.

(10) Patent No.: US 8,354,251 B2
(45) Date of Patent: Jan. 15, 2013

(54) TRANSACTIVATION SYSTEM FOR MAMMALIAN CELLS

(75) Inventors: Christopher Robert Bebbington, San Mateo, CA (US); Bo Yu, Sunnyvale, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 1346 days.

(21) Appl. No.: 10/585,149

(22) PCT Filed: Dec. 30, 2004

(86) PCT No.: PCT/US2004/043830
§ 371 (c)(1),
(2), (4) Date: Jun. 30, 2006

(87) PCT Pub. No.: WO2005/065348
PCT Pub. Date: Jul. 21, 2005

(65) Prior Publication Data
US 2009/0111144 A1    Apr. 30, 2009

Related U.S. Application Data

(60) Provisional application No. 60/533,917, filed on Dec. 31, 2003.

(51) Int. Cl.
*C12P 21/00* (2006.01)
*C12N 15/85* (2006.01)

(52) U.S. Cl. ...................................... 435/70.1; 435/325

(58) Field of Classification Search .................. None
See application file for complete search history.

(56) References Cited

U.S. PATENT DOCUMENTS

| 5,866,359 A | 2/1999 | Cockett et al. |
| 6,274,341 B1 | 8/2001 | Bailey et al. |
| 6,653,101 B1 | 11/2003 | Cockett et al. |
| 2002/0106789 A1 | 8/2002 | Antoniou et al. |

FOREIGN PATENT DOCUMENTS

| WO | WO 00/05393 | 2/2000 |
| WO | WO 01/88194 | * 11/2001 |
| WO | WO 03/006607 | 1/2003 |

OTHER PUBLICATIONS

Rao et al (PNAS, 1992. vol. 89, pp. 7742-7746).*
Brian S. Chang et al., "Identification of Novel Regulatory Domain in Bcl-$x_L$ and Bcl-2", The EMBO Journal, vol. 16, No. 5, pp. 968-977, 1997.
Bruno Chatton, et al., "Transcriptional Activation by the Adenovirus Larger E1a Product Is Mediated by Members of the Cellular Transcription Factor ATF Family Which Can Directly Associate with E1a", Molecular and Cellular Biology, vol. 13, No. 1, Jan. 1993, pp. 561-670.
Mark I. Cockett, Christopher R. Bebbington and Geoffrey T. Yarranton, "The Use of Engineered E1A genes to Transactivate the hCMV-MIE Promoter in Permanent CHO Cell Lines",Nucleic Acids Research, vol. 19, No. 2, pp. 319-325.
Andrea Cuconati and Eileen White, "Viral Homologs of BCL-2: Role of Apoptosis in the regulation of Virus Infection", Genes & Development vol. 16, 2002, pp. 2465-2478.
Bruno Figueroa Jr., et al., "Comparison of Bcl-2 to a Bcl-2 Deletion Mutant for Mammalian Cells Exposed to Culture Insults", 2001 Biotechnology and Bioengineering, vol. 73, No. 3, pp. 211-222.
David Jones, et al., "High-Level Expression of Recombinant IgG in the Human Cell Line PER.C6", Biotechnol. Prog. 2003 American Chemical Society and American Institute of Chemical Engineers Published, pp. 163-168.
Jeng-Shin Lee, Xiaolin Zhang§ and Yang Shi, "Differential Interactions of the CREB/ATF Family of Transcription Factors with p300 and Adenovirus E1A", The Journal of Biological Chemistry, vol. 271, No. 30, Jul. 26, 1996, pp. 17666-17674.
Suk Kyoo Lee and Gyun Min Lee, "Development of Apoptosis-Resistant Dihydrofolate Reductase-Deficient Chinese Hamster Ovary Cell Line", Biotechnology and Bioengineering, vol. 82, No. 7, Jun. 30, 2003, pp. 872-876.
James W. Lillie, Paul M. Loewenstein, Michael R. Green and Maurice Green, "Functional Domains of Adenovirus Type 5 E1a Proteins", Cell, Sep. 25, 1987, vol. 50, pp. 1091-1100.
Sylvain Mercille and Bernard Massie, "Apoptosis-Resistant E1B-19K-Expressing NS/0 Myeloma Cells Exhibit Increased Viability and Chimeric Antibody Productivity under Perfusion Culture Conditions", Biotechnology and Bioengineering, vol. 63, No. 5, Jun. 5, 1999, pp. 529-543.
Traci A. Sanchez, et al., "Zinc Finger and Carboxyl Regions of Adenovirus E1A 13S CR3 Are Important for Transactivation of the Cytomegalovirus Major Immediate Early Promoter by Adenovirus", www.atsjournals.org, Am J. Respir. Cell Mol. Biol., vol. 23, 2000, pp. 670-677.
Tina M. Sauerwald, Michael J. Betenbaugh and George A. Oyler, "Inhibiting Apoptosisi in Mammalian Cell Culture Using the Caspase Inhibitor XIAP and Deletion Mutants", Biotechnology and Bioengineering, vol. 77, No. 6, Mar. 20, 2002, pp. 704-716.
Tina M. Sauerwald, George A. Oyler and Michael J. Betenbaugh, "Study of Caspase Inhibitors for Limiting Death in Mammalian Cell Culture", Biotechnology and Bioengineering, vol. 81, No. 3, Feb. 5, 2003, pp. 329-340.
BM Pützer, et al., "E1A Is Sufficient by Itself to Induce Apoptosis Independent of p53 and Other Adenoviral Gene Products", Cell Death and Differentiation, vol. 7, 2000, pp. 177-188.
B.T. Tey, et al., "Bcl-2 Medical Suppression of Apoptosis in Myeloma NS0 Cultures", www.elesvier.com/locate/jbiotec, Journal of Biotechnology 79, 2000, pp. 147-159.
Eckhard Bender, et al., "Recombinant Human Antibodies: Linkage of an Fab Fragment From a Combinatorial Library to an Fc Fragment for Expression in Mammalian Cell Culture", Hum. Antibod. Hybridomas, vol. 4, No. 2, Apr. 1993, pp. 39-41 & 74-79.
European Search Report.

* cited by examiner

*Primary Examiner* — Celine Qian
(74) *Attorney, Agent, or Firm* — HelixIP LLP

(57) ABSTRACT

The present invention is directed generally to compositions and methods for expressing recombinant proteins in a mammalian host cell using a co-expressed transcriptional activator. In particular, the invention provides vectors, host cells, and methods of expressing at least one desired polypeptide by transfecting a mammalian host cell with cistrons encoding a transactivator, a desired polypeptide, and an apoptosis-protective protein.

2 Claims, 22 Drawing Sheets

MAQAGRTGYDNREIVMKYIHYKLSQRGYEWDVGDVDAAPLG
AAPTPGIFSFQPESNPTPAVHRDMAARTSPLRPIVATTGPT
LSPVPPVVHLTLRRAGDDFSRRYRRDFAEMSSQLHLTPFTA
RGRFATVVEELFRDGVNWGRIVAFFEFGGVMCVESVNREMS
PLVDNIALWMTEYLNRHLHTWIQDNGGWDAFVELYGPSVRP
LFDFSWLSLKTLLSLALVGACITLGTYLGHK (SEQ ID NO: 1)

FIG. 1

MAQAGRTGYDNREIVMKYIHYKLSQRGYEWDVGDVDAAAAA
ASPVPPVVHLTLRRAGDDFSRRYRRDFAEMSSQLHLTPFTA
RGRFATVVEELFRDGVNWGRIVAFFEFGGVMCVESVNREMS
PLVDNIALWMTEYLNRHLHTWIQDNGGWDAFVELYGPSVRP
LFDFSWLSLKTLLSLALVGACITLGTYLGHK (SEQ ID NO: 2)

FIG. 2

```
  1 ATGGCTCAAG CTGGGAGAAC AGGGTATGAT AACCGAGAGA TCGTGATGAA
 51 GTACATCCAT TATAAGCTGT CACAGAGGGG CTACGAGTGG GATGTGGGAG
101 ATGTGGACGC CGCGGCCGCG GCCGCGAGCC CCGTGCCACC TGTGGTCCAC
151 CTGACCCTCC GCCGGGCTGG GGATGACTTC TCCCGTCGCT ACCGTCGCGA
201 CTTCGCGGAG ATGTCCAGTC AGCTGCACCT GACGCCCTTC ACCGCGAGGG
251 GACGCTTTGC TACGGTGGTG GAGGAACTCT TCAGGGATGG GGTGAACTGG
301 GGGAGGATTG TGGCCTTCTT TGAGTTCGGT GGGGTCATGT GTGTGGAGAG
351 CGTCAACAGG GAGATGTCAC CCCTGGTGGA CAACATCGCC CTGTGGATGA
401 CCGAGTACCT GAACCGGCAT CTGCACACCT GGATCCAGGA TAACGGAGGC
451 TGGGACGCAT TTGTGGAACT GTACGGCCCC AGTGTGAGGC CTCTGTTTGA
501 TTTCTCTTGG CTGTCTCTGA AGACCCTGCT CAGCCTGGCC CTGGTCGGGG
551 CCTGCATCAC TCTGGGTACC TACCTGGGCC ACAAGTGA     (SEQ ID NO: 3)
```

FIG. 3

MRHIICHGGVITEEMAASLLDQLIEEVLADNLPPPSHFE
PPTLHELHDLDVTAPEDPNEEAVSQIFPDSVMLAVQEGI
DLLTFPPAPGSPEPPHLSRQPEQPEQRALGPVSMPNLVP
EVIDLTGHEAGFPPSDDEDEEGEEFVLDYVEHPGHGCR
SCHYHRRNTGDPDIMCSLCYMRTCGMFVYSPVSEPEPE
PEPEPEPARPTRRPKMAPAILRRPTSPVSRECNSSTDSCD
SGPSNTPPEIHPVVPLCPIKPVAVRVGGRRQAVECIEDL
LNEPGQPLDLSCKRPRP    (SEQ ID NO: 4)

FIG. 4

```
  1 ATGAGACATA TTATCTGCCA CGGAGGTGTT ATTACCGAAG AAATGGCCGC
 51 CAGTCTTTTG GACCAGCTGA TCGAAGAGGT ACTGGCTGAT AATCTTCCAC
101 CTCCTAGCCA TTTTGAACCA CCTACCCTTC ACGAACTGCA TGATTTAGAC
151 GTGACGGCCC CCGAAGATCC CAACGAGGAG GCGGTTTCGC AGATTTTTCC
201 CGACTCTGTA ATGTTGGCGG TGCAGGAAGG GATTGACTTA CTCACTTTTC
251 CGCCGGCGCC CGGTTCTCCG GAGCCGCCTC ACCTTTCCCG GCAGCCCGAG
301 CAGCCGGAGC AGAGAGCCTT GGGTCCGGTT CTATGCCAA ACCTTGTACC
351 GGAGGTGATC GATCTTACCG GCCACGAGGC TGGCTTTCCA CCCAGTGACG
401 ACGAGGATGA AGAGGGTGAG GAGTTTGTGT TAGATTATGT GGAGCACCCC
451 GGGCACGGTT GCAGGTCTTG TCATTATCAC CGGAGGAATA CGGGGGACCC
501 AGATATTATG TGTTCGCTTT GCTATATGAG GACCTGTGGC ATGTTTGTCT
551 ACAGTAAGTG AAAATTATGG GCAGTGGGTG ATAGAGTGGT GGGTTTGGTG
601 TGGTAATTTT TTTTTTAATT TTTACAGTTT TGTGGTTTAA AGAATTTTGT
651 ATTGTGATTT TTTTAAAAGG TCCTGTGTCT GAACCTGAGC CTGAGCCCGA
701 GCCAGAACCG GAGCCTGCAA GACCTACCCG CCGTCCTAAA ATGGCGCCTG
751 CTATCCTGAG ACGCCCGACA TCACCTGTGT CTAGAGAATG CAATAGTAGT
801 ACGGATAGCT GTGACTCCGG TCCTTCTAAC ACACCTCCTG AGATACACCC
851 GGTGGTCCCG CTGTGCCCCA TTAAACCAGT TGCCGTGAGA GTTGGTGGGC
901 GTCGCCAGGC TGTGGAATGT ATCGAGGACT TGCTTAACGA GCCTGGGCAA
951 CCTTTGGACT TGAGCTGTAA ACGCCCCAGG CCATAA       (SEQ ID NO: 5)
```

FIG. 5

```
  1 GAATTCGCCG CCACCATGGA GGCTTGGGAG TGTTTGGAAG ATTTTTCTGC
 51 TGTGCGTAAC TTGCTGGAAC AGAGCTCTAA CAGTACCTCT TGGTTTTGGA
101 GGTTTCTGTG GGCTCATCC  CAGGCAAAGT TAGTCTGCAG AATTAAGGAG
151 GATTACAAGT GGGAATTTGA AGAGCTTTTG AAATCCTGTG GTGAGCTGTT
201 TGATTCTTTG AATCTGGGTC ACCAGGCGCT TTTCCAAGAG AAGGTCATCA
251 AGACTTTGGA TTTTTCCACA CCGGGGCGCG CTGCGGCTGC TGTTGCTTTT
301 TTGAGTTTTA TAAAGGATAA ATGGAGCGAA GAAACCCATC TGAGCGGGGG
351 GTACCTGCTG GATTTTCTGG CCATGCATCT GTGGAGAGCG GTTGTGAGAC
401 ACAAGAATCG CCTGCTACTG TTGTCTTCCG TCCGCCCGGC GATAATACCG
451 ACGGAGGAGC AGCAGCAGCA GCAGGAGGAA GCCAGGCGGC GGCGGCAGGA
501 GCAGAGCCCA TGGAACCCGA GAGCCGGCCT GGACCCTCGG GAATGAATGT
551 TGGTCGAC         (SEQ ID NO: 15)
```

FIG. 6

```
     SalI
   1 GTCGACGCCG CCACCATGCC GCCCAAAACC CCCCGAAAAA CGGCCGCCAC
                     M  P  P  K  T  P  R  K  T  A  A  T

51 CGCCGCCGCT GCCGCCGCGG AACCCCCGGC ACCGCCGCCG CCGCCCCCTC
      A  A  A  A  A  A  E  P  P  A  P  P  P  P  P  P  P

101 CTGAGGAGGA CCCAGAGCAG GACAGCGGCC CGGAGGACCT GCCTCTCGTC
      L  E  E  D  P  E  Q  D  S  G  P  E  D  L  P  L  V

151 AGGCTTGAGT TTGAAGAAAC AGAAGAACCT GATTTTACTG CATTATGTCA
      R  L  E  F  E  E  T  E  E  P  D  F  T  A  L  C  Q

201 GAAATTAAAG ATACCAGATC ATGTCAGAGA GAGAGCTTGG TTAACTTGGG
      K  L  K  I  P  D  H  V  R  E  R  A  W  L  T  W  E

251 AGAAAGTTTC ATCTGTGGAT GGAGTATTGG GAGGTTATAT TCAAAAGAAA
      K  V  S  S  V  D  G  V  L  G  G  Y  I  Q  K  K

301 AAGGAACTGT GGGGAATCTG TATCTTTATT GCACGAGTTG ACCTAGATGA
      K  E  L  W  G  I  C  I  F  I  A  R  V  D  L  D  E

351 GATGTCGTTC ACTTTACTGA GCTACAGAAA AACATACGAA ATCAGTGTCC
      M  S  F  T  L  L  S  Y  R  K  T  Y  E  I  S  V  H

401 ATAAATTCTT TAACTTACTA AAAGAAATTG ATACCAGTAC CAAAGTTGAT
      K  F  F  N  L  L  K  E  I  D  T  S  T  K  V  D

451 AATGCTATGT CAAGACTGTT GAAGAAGTAT GATGTATTGT TTGCACTCTT
      N  A  M  S  R  L  L  K  K  Y  D  V  L  F  A  L  F

501 CAGCAAATTG GAAAGGACAT GTGAACTTAT ATATTTGACA CAACCCAGCA
      S  K  L  E  R  T  C  E  L  I  Y  L  T  Q  P  S  S

551 GTTCGATATC TACTGAAATA AATTCTGCAT TGGTGCTAAA AGTTTCTTGG
      S  I  S  T  E  I  N  S  A  L  V  L  K  V  S  W

601 ATCACATTTT TATTAGCTAA AGGGGAAGTA TTACAAATGG AAGATGATCT
      I  T  F  L  L  A  K  G  E  V  L  Q  M  E  D  D  L

651 GGTGATTTCA TTTCAGTTAA TGCTATGTGT CCTTGACTAT TTTATTAAAC
      V  I  S  F  Q  L  M  L  C  V  L  D  Y  F  I  K  L
```

FIG. 7A

```
701  TCTCACCTCC CATGTTGCTC AAAGAACCAT ATAAAACAGC TGTTATACCC
      S  P  P    M  L     K  E  P  Y   K  T  A    V  I  P

751  ATTAATGGTT CACCTCGAAC ACCCAGGCGA GGTCAGAACA GGAGTGCACG
      I  N  G  S  P  R  T   P  R  R    G  Q  N  R   S  A  R

801  GATAGCAAAA CAACTAGAAA ATGATACAAG AATTATTGAA GTTCTCTGTA
      I  A  K    Q  L  E  N   D  T  R    I  I  E    V  L  C  K

851  AAGAACATGA ATGTAATATA GATGAGGTGA AAAATGTTTA TTTCAAAAAT
      E  H  E    C  N  I    D  E  V  K   N  V  Y    F  K  N

EcoRI
901  TTTATACCTT TTATGAATTC TCTTGGACTT GTAACATCTA ATGGACTTCC
      F  I  P  F   M  N  S    L  G  L    V  T  S  N   G  L  P

951  AGAGGTTGAA AATCTTTCTA AACGATACGA AGAAATTTAT CTTAAAAATA
      E  V  E    N  L  S  K   R  Y  E    E  I  Y    L  K  N  K

1001 AAGATCTAGA TCGAAGATTA TTTTTGGATC ATGATAAAAC TCTTCAGACT
      D  L  D    R  R  L    F  L  D  H   D  K  T    L  Q  T

1051 GATTCTATAG ACAGTTTTGA ACACAGAGA ACACCACGAA AAAGTAACCT
      D  S  I  D   S  F  E    T  Q  R    T  P  R  K   S  N  L

1101 TGATGAAGAG GTGAATATAA TTCCTCCACA CACTCCAGTT AGGACTGTTA
      D  E  E    V  N  I  I   P  P  H    T  P  V    R  T  V  M

1151 TGAACACTAT CCAACAATTA ATGATGATTT TAAATTCTGC AAGTGATCAA
      N  T  I    Q  Q  L    M  M  I  L   N  S  A    S  D  Q

1201 CCTTCAGAAA ATCTGATTTC CTATTTTAAC AACTGCACAG TGAATCCAAA
      P  S  E  N   L  I  S    Y  F  N    N  C  T    V  N  P  K

1251 AGAAAGTATA CTGAAAAGAG TGAAGGATAT AGGATACATC TTTAAAGAGA
      E  S  I    L  K  R  V   K  D  I    G  Y  I    F  K  E  K

1301 AATTTGCTAA AGCTGTGGGA CAGGGTTGTG TCGAATTGG ATCACAGCGA
      F  A  K    A  V  G    Q  G  C  V   E  I  G    S  Q  R

1351 TACAAACTTG GAGTTCGCTT GTATTACCGA GTAATGGAAT CCATGCTTAA
      Y  K  L  G   V  R  L    Y  Y  R    V  M  E  S   M  L  K
```

FIG. 7B

```
1401 ATCAGAAGAA GAACGATTAT CCATTCAAAA TTTTAGCAAA CTTCTGAATG
      S  E  E   E  R  L   S  I  Q  N   F  S  K   L  L  N  D

1451 ACAACATTTT TCATATGTCT TTATTGGCGT GCGCTCTTGA GGTTGTAATG
      N  I  F   H  M  S   L  L  A  C   A  L  E   V  V  M

1501 GCCACATATA GCAGAAGTAC ATCTCAGAAT CTTGATTCTG AACAGATTT
      A  T  Y   S  R  S  T   S  Q  N   L  D  S  G   T  D  L

1551 GTCTTTCCCA TGGATTCTGA ATGTGCTTAA TTTAAAAGCC TTTGATTTTT
      S  F  P   W  I  L  N   V  L  N   L  K  A   F  D  F  Y

1601 ACAAAGTGAT CGAAAGTTTT ATCAAAGCAG AAGGCAACTT GACAAGAGAA
      K  V  I   E  S  F   I  K  A  E   G  N  L   T  R  E

1651 ATGATAAAAC ATTTAGAACG ATGTGAACAT CGAATCATGG AATCCCTTGC
      M  I  K  H   L  E  R   C  E  H   R  I  M  E   S  L  A

1701 ATGGCTCTCA GATTCACCTT TATTTGATCT TATTAAACAA TCAAAGGACC
      W  L  S   D  S  P  L   F  D  L   I  K  Q   S  K  D  R

1751 GAGAAGGACC AACTGATCAC CTTGAATCTG CTTGTCCTCT TAATCTTCCT
      E  G  P   T  D  H   L  E  S  A   C  P  L   N  L  P

1801 CTCCAGAATA ATCACACTGC AGCAGATATG TATCTTTCTC CTGTAAGATC
      L  Q  N  N   H  T  A   A  D  M   Y  L  S  P   V  R  S

1851 TCCAAAGAAA AAAGGTTCAA CTACGCGTGT AAATTCTACT GCAAATGCAG
      P  K  K   K  G  S  T   T  R  V   N  S  T   A  N  A  E

1901 AGACACAAGC AACCTCAGCC TTCCAGACCC AGAAGCCATT GAAATCTACC
      T  Q  A   T  S  A   F  Q  T  Q   K  P  L   K  S  T

1951 TCTCTTTCAC TGTTTTATAA AAAAGTGTAT CGGCTAGCCT ATCTCCGGCT
      S  L  S  L   F  Y  K   K  V  Y   R  L  A  Y   L  R  L

2001 AAATACACTT TGTGAACGCC TTCTGTCTGA GCACCCAGAA TTAGAACATA
      N  T  L   C  E  R  L   L  S  E   H  P  E   L  E  H  I

2051 TCATCTGGAC CCTTTTCCAG CACACCCTGC AGAATGAGTA TGAACTCATG
      I  W  T   L  F  Q   H  T  L  Q   N  E  Y   E  L  M
```

FIG. 7C

```
2101 AGAGACAGGC ATTTGGACCA AATTATGATG TGTTCCATGT ATGGCATATG
      R  D  R  H    L  D     I  M  M    C  S  M  Y    G  I  C

2151 CAAAGTGAAG AATATAGACC TTAAATTCAA AATCATTGTA ACAGCATACA
      K  V  K    N  I  D  L  K  F  K    I  I  V    T  A  Y  K

2201 AGGATCTTCC TCATGCTGTT CAGGAGACAT TCAAACGTGT TTTGATCAAA
      D  L  P    H  A  V    Q  E  T  F    K  R  V    L  I  K

2251 GAAGAGGAGT ATGATTCTAT TATAGTATTC TATAACTCGG TCTTCATGCA
      E  E  E  Y  D  S  I    I  V  F    Y  N  S  V    F  M  Q

2301 GAGACTGAAA ACAAATATTT TGCAGTATGC TTCCACCAGG CCCCCTACCT
      R  L  K    T  N  I  L  Q  Y  A    S  T  R    P  P  T  L

2351 TGTCACCAAT ACCTCACATT CCTCGAAGCC CTTACAAGTT TCCTAGTTCA
      S  P  I    P  H  I    P  R  S  P    Y  K  F    P  S  S

2401 CCCTTACGGA TTCCTGGAGG GAACATCTAT ATTTCACCCC TGAAGAGTCC
      P  L  R  I   P  G  G    N  I  Y    I  S  P  L    K  S  P

2451 ATATAAAATT TCAGAAGGTC TGCCAACACC AACAAAAATG ACTCCAAGAT
      Y  K  I    S  E  G  L    P  T  P    T  K  M    T  P  R  S

2501 CAAGAATCTT AGTATCAATT GGTGAATCAT TCGGGACTTC TGAGAAGTTC
      R  I  L    V  S  I    G  E  S  F    G  T  S    E  K  F

2551 CAGAAAATAA ATCAGATGGT ATGTAACAGC GACCGTGTGC TCAAAAGAAG
      Q  K  I  N  Q  M  V    C  N  S    D  R  V  L    K  R  S

2601 TGCTGAAGGA AGCAACCCTC CTAAACCACT GAAAAAACTA CGCTTTGATA
      A  E  G    S  N  P  P    K  P  L    K  K  L    R  F  D  I

2651 TTGAAGGATC AGATGAAGCA GATGGAAGTA AACATCTCCC AGGAGAGTCC
      E  G  S    D  E  A    D  G  S  K    H  L  P    G  E  S

2701 AAATTTCAGC AGAAACTGGC AGAAATGACT TCTACTCGAA CACGAATGCA
      K  F  Q  Q    K  L  A    E  M  T    S  T  R  T    R  M  Q

2751 AAAGCAGAAA ATGAATGATA GCATGGATAC CTCAAACAAG GAAGAGAAAT
      K  Q  K    M  N  D  S    M  D  T    S  N  K    E  E  K  *

NotI
2801 GAGGATCTCA GGACCGGCGG CCGC
```

FIG. 7D

```
     EcoRI
  1  GAATTCGCCG CCACCATGAC CATGGACTCT GGAGCAGACA ACCAGCAGAG
                      M  T  M  D  S  G  A  D  N  Q  Q  S

51  TGGAGATGCA GCTGTAACAG AAGCTGAAAA CCAACAAATG ACAGTTCAAG
      G  D  A  A  V  T  E  A  E  N  Q  Q  M  T  V  Q  A

101  CCCAGCCACA GATTGCCACA TTAGCCCAGG TATCTATGCC AGCAGCTCAT
      Q  P  Q  I  A  T  L  A  Q  V  S  M  P  A  A  H

151  GCAACATCAT CTGCTCCCAC CGTAACTCTA GTACAGCTGC CCAATGGGCA
      A  T  S  S  A  P  T  V  T  L  V  Q  L  P  N  G  Q

201  GACAGTTCAA GTCCATGGAG TCATTCAGGC GGCCCAGCCA TCAGTTATTC
      T  V  Q  V  H  G  V  I  Q  A  A  Q  P  S  V  I  Q

251  AGTCTCCACA AGTCCAAACA GTTCAGATTT CAACTATTGC AGAAAGTGAA
      S  P  Q  V  Q  T  V  Q  I  S  T  I  A  E  S  E

301  GATTCACAGG AGTCAGTGGA TAGTGTAACT GATTCCCAAA AGCGAAGGGA
      D  S  Q  E  S  V  D  S  V  T  D  S  Q  K  R  R  E

351  AATTCTTTCA AGGAGGCCTT CCTTCAGGAA AATTTTGAAT GACTTATCTT
      I  L  S  R  R  P  S  F  R  K  I  L  N  D  L  S  S

401  CTGATGCACC AGGAGTGCCA AGGATTGAAG AAGAGAAGTC TGAAGAGGAG
      D  A  P  G  V  P  R  I  E  E  E  K  S  E  E  E

451  GCTTCAGCAC CTGCCATCAC CGCTGTAGCG GTGCCAACGC CAATTTACCG
      A  S  A  P  A  I  T  A  V  A  V  P  T  P  I  Y  R

501  GACTAGCAGT GGACAGTATA TTACCATTAC CCAGAGAGGA GCAATACAGC
      T  S  S  G  Q  Y  I  T  I  T  Q  R  G  A  I  Q  L

551  TGGCTAGCAA TGGTACCGAT GGGGTACAGG GCCTGCAAAC ATTAACCATG
      A  S  N  G  T  D  G  V  Q  G  L  Q  T  L  T  M

601  GCCAATGCAG CAGCCACTCA GCCGGGTACT ACCATTCTAC AGTATGCACA
      A  N  A  A  A  T  Q  P  G  T  T  I  L  Q  Y  A  Q

651  GACCACTGAT GGACAGCAGA TCTTAGTGCC CAGCAACCAA GTTGTTGTTC
      T  T  D  G  Q  Q  I  L  V  P  S  N  Q  V  V  V  Q
```

FIG. 8A

```
701 AAGCTGCCTC TGGAGACGTA CAAACATACC AGATTCGCAC AGCACCCACT
     A   A   S   G   D   V   Q   T   Y   Q   I   R   T   A   P   T

751 AGCACTATTG CCCCTGGAGT TGTTATGGCA TCCTCCCCAG CACTTCCTAC
     S   T   I   A   P   G   V   V   M   A   S   S   P   A   L   P   T

801 ACAGCCTGCT GAAGAAGCAG CACGAAAGAG AGAGGTCCGT CTAATGAAGA
     Q   P   A   E   E   A   A   R   K   R   E   V   R   L   M   K   N

851 ACAGGGAAGC AGCTCGTGAG TGTCGTAGAA AGAAGAAAGA ATATGTGAAA
     R   E   A   A   R   E   C   R   R   K   K   E   Y   V   K

901 TGTTTAGAAA ACAGAGTGGC AGTGCTTGAA AATCAAAACA AGACATTGAT
     C   L   E   N   R   V   A   V   L   E   N   Q   N   K   T   L   I

951 TGAGGAGCTA AAAGCACTTA AGGACCTTTA CTGCCACAAA TCAGATTAAT
     E   E   L   K   A   L   K   D   L   Y   C   H   K   S   D   *

SalI
1001 TTGGGTCGAC
```

FIG. 8B

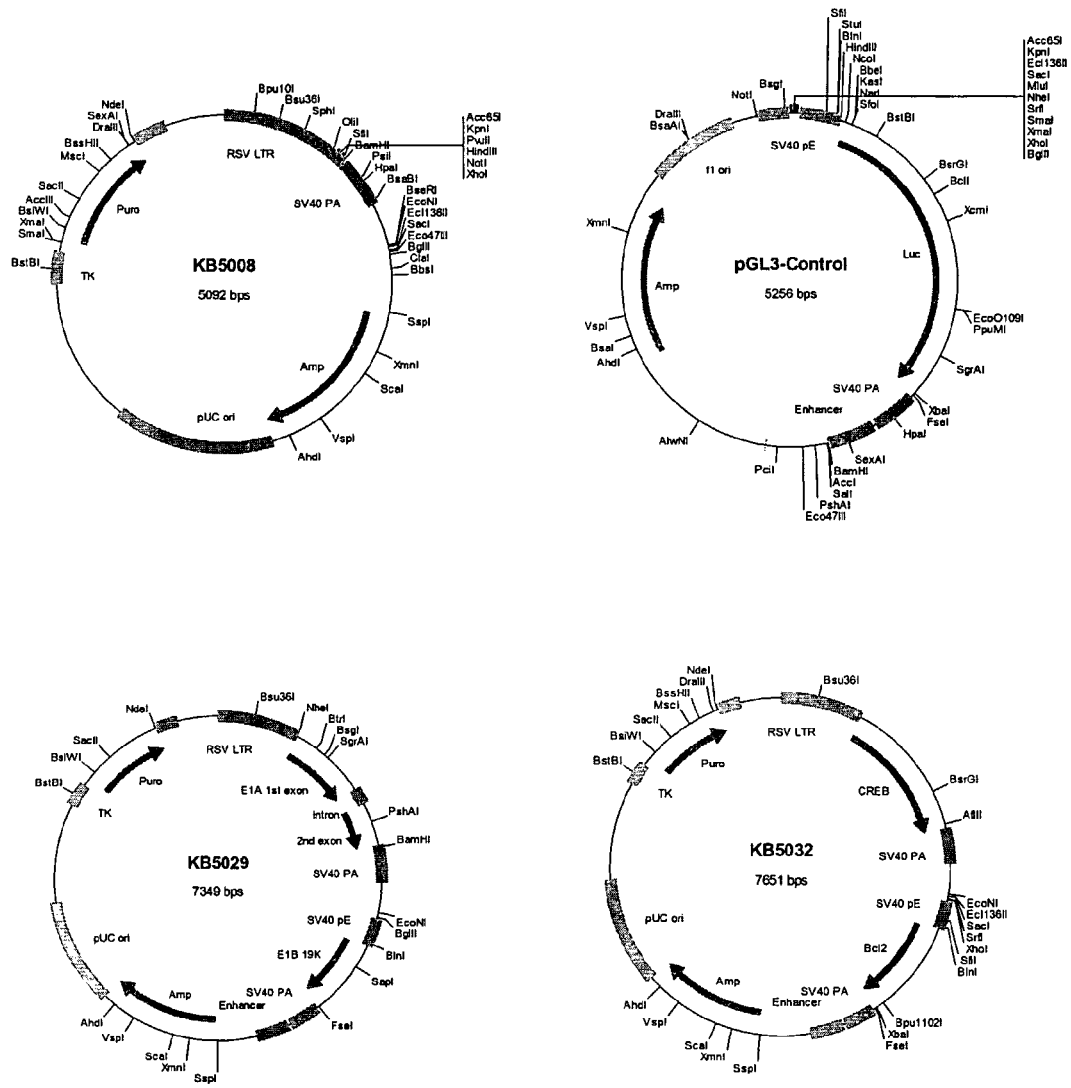
Figure 9. Maps of KB5008, pGL3-Control, KB5029, and KB5032.
KB5008 carries a RSVLTR promoter and was used to clone E1a and CREB. pGL3-Control carries a SV40 promoter and was used to clone E1b-19K and Bcl2. KB5029 carries the double expression cassettes for E1a and E1b-19K. KB5032 carries the double expression cassettes for CREB and Bcl2.

| | | | | | |
|---|---|---|---|---|---|
| 1 | aagcttgccg HindIII | ccaccatgag M | acatattatc R H I I | tgccacggag C H G | gtgttattac G V I |
| 51 | cgaagaaatg T E M | gccgccagtc A A S | ttttggacca L L D | gctgatcgaa Q L I E | gaggtactgg E V L |
| 101 | ctgataatct A D N | tccacctcct L P P P | agccattttg S H F | aaccacctac E P P | ccttcacgaa T L H E |
| 151 | ctgtatgatt L Y D | tagacgtgac L D V | ggcccccgaa T A P E | gatcccaacg D P N | aggaggcggt E E A |
| 201 | ttcgcagatt V S Q I | tttcccgact F P D | ctgtaatgtt S V M | ggcggtgcag L A V Q | gaagggattg E G I |
| 251 | acttactcac D L L | ttttccgccg T F P P | gcgcccggtt A P G | ctccggagcc S P E | gcctcacctt P P H L |
| 301 | tcccggcagc S R Q | ccgagcagcc P E Q | ggagcagaga P E Q R | gccttgggtc A L G | cggtttctat P V S |
| 351 | gccaaacctt M P N L | gtaccggagg V P E | tgatcgatct V I D | tacctgccac L T C H | gaggctggct E A G |
| 401 | ttccacccag F P P | tgacgacgag S D D E | gatgaagagg D E E | gtgaggagtt G E E | tgtgttagat F V L D |
| 451 | tatgtggagc Y V E | accccgggca H P G | cggttgcagg H G C R | tcttgtcatt S C H | atcaccggag Y H R |
| 501 | gaatacgggg R N T G | gacccagata D P D | ttatgtgttc I M C | gctttgctat S L C Y | atgaggacct M R T |
| 551 | gtggcatgtt C G M | tgtctacagt F V Y S | cctgtgtctg P V S | aacctgagcc E P E | tgagcccgag P E P E |
| 601 | ccagaaccgg P E P | agcctgcaag E P A | acctacccgc R P T R | cgtcctaaaa R P K | tggcgcctgc M A P |
| 651 | tatcctgaga A I L R | cgcccgacat R P T | cacctgtgtc S P V | tagagaatgc S R E C | aatag

```
1   aagcttgccg ccaccatgag acatattatc tgccacggag gtgttattac
    HindIII    M  R  H  I  I  C  H  G  G  V  I 51  cgaagaaatg gccgccagtc ttttggacca gctgatcgaa gaggtactgg
    T  E  E  M  A  A  S  L  L  D  Q  L  I  E  E  V  L 101 ctgataatct tccacctcct agccattttg aaccacctac ccttcacgaa
    A  D  N  L  P  P  P  S  H  F  E  P  P  T  L  H  E 151 ctgcatgatt tagacgtgac ggccccgaa gatcccaacg aggaggcggt
    L  H  D  L  D  V  T  A  P  E  D  P  N  E  E  A 201 ttcgcagatt tttcccgact ctgtaatgtt ggcggtgcag gaagggattg
    V  S  Q  I  F  P  D  S  V  M  L  A  V  Q  E  G  I 251 acttactcac ttttccgccg gcgcccggtt ctccggagcc gcctcacctt
    D  L  L  T  F  P  P  A  P  G  S  P  E  P  P  H  L 301 tcccggcagc ccgagcagcc ggagcagaga gccttgggtc cggtttctat
    S  R  Q  P  E  Q  P  E  Q  R  A  L  G  P  V  S 351 gccaaacctt gtaccggagg tgatcgatct tacctgccac gaggctggct
    M  P  N  L  V  P  E  V  I  D  L  T  C  H  E  A  G 401 ttccacccag tgacgacgag gatgaagagg gtgaggagtt tgtgttagat
    F  P  P  S  D  D  E  D  E  E  G  E  E  F  V  L  D 451 tatgtggagc accccgggca cggttgcagg tcttgtcatt atcaccggag
    Y  V  E  H  P  G  H  G  C  R  S  C  H  Y  H  R 501 gaatacgggg gacccagata ttatgtgttc gctttgctat atgaggacct
    R  N  T  G  D  P  D  I  M  C  S  L  C  Y  M  R  T 551 gtggcatgtt tgtctacagt cctgtgtctg aacctgagcc tgagcccgag
    C  G  M  F  V  Y  S  P  V  S  E  P  E  P  E  P  E 601 ccagaaccgg agcctgcaag acctacccgc cgtcctaaaa tggcgcctgc
    P  E  P  E  P  A  R  P  T  R  R  P  K  M  A  P 651 tatcctgaga cgcccgacat cacctgtgtc tagagaatgc aatagtagta
    A  I  L  R  R  P  T  S  P  V  S  R  E  C  N  S  S 701 cggatagctg tgactccggt ccttctaaca cacctcctga gatacacccg
    T  D  S  C  D  S  G  P  S  N  T  P  P  E  I  H  P 751 gtggtcccgc tgtgccccat taaaccagtt gccgtgagag ttggtgggcg
    V  V  P  L  C  P  I  K  P  V  A  V  R  V  G  G 801 tcgccaggct gtggaatgta tcgaggactt gcttaacgag cctgggcaac
    R  R  Q  A  V  E  C  I  E  D  L  L  N  E  P  G  Q 851 ctttggactt gagctgtaaa cgccccaggc cataactcga g
    P  L  D  L  S  C  K  R  P  R  P  -  XhoI
```

Figure 11. Nucleotide coding sequence of E1a_Y47H (SEQ ID NO: 41). Cloning sites HindIII and XhoI are underscored.

```
  1  aagcttgccg ccaccatgac catggaatct ggagcagaca accagcagag
     HindIII             M  T  M  E  S   G  A  D   N  Q  Q 51  tggagatgct gctgtaacag aagctgaaaa tcaacaaatg acagctcaag
     S  G  D  A  A  V  T   E  A  E    N  Q  Q  M   T  A  Q 101  cccaaccaca gattgccaca ttagcccagg tatccatgcc agcagctcat
     A  Q  P   D  I  A  T   L  A  Q   V  S  M    P  A  A  H 151  gcgacatcat ctgctcccac tgtaacctta gtgcagctgc ccaatgggca
     A  T  S    S  A  P    T  V  T  L  V  Q  L   P  N  G 201  gacagtccaa gtccatggag ttattcaggc ggcccagcca tcagttattc
     Q  T  V  Q  V  H  G   V  I  Q   A  A  Q  P   S  V  I 251  agtctccaca agtccaaaca gttcagtctt cctgtaagga cttaaaaaga
     Q  S  P   Q  V  Q  T  V  Q  S   S  C  K    D  L  K  R 301  ctttctccg  gaactcagat ttcaactatt gcagaaagtg aggattcaca
     L  F  S    G  T  Q   I  S  T  I  A  E  S   E  D  S 351  ggaatctgtg gatagtgtaa ctgattccca aaagcgaagg gaaattcttt
     Q  E  S  V  D  S  V   T  D  S   Q  K  R  R  E  I  L 401  caaggaggcc ttcctacagg aaaatttga  atgacttatc ttctgatgca
     S  R  R    P  S  Y  R  K  I  L  N  D  L    S  S  D  A 451  ccaggggtgc caaggattga agaagaaaag tcggaagagg agacttcagc
     P  G  V   P  R  I    E  E  E  K  S  E  E   E  T  S 501  ccctgccatc accactgtga cagtgccaac tccgatttac cagacaagca
     A  P  A  I  T  T  V   T  V  P   T  P  I  Y  Q  T  S 551  gtgggcagta tattgccatt acccagggag gagctataca gctggctaac
     S  G  Q    Y  I  A  I  T  Q  G   G  A  I   Q  L  A  N 601  aatggtaccg atggggtaca gggccttcag acattaacca tgaccaatgc
     N  G  T    D  G  V   Q  G  L  Q  T  L  T   M  T  N 651  agctgccact cagccgggta ccactattct acagtatgca cagaccactg
     A  A  T    Q  P  G   T  T  I   L  Q  Y  A   Q  T  T 701  atggacagca gattctagtg cccagcaacc aagttgttgt tcaagctgcc
     D  G  Q    Q  I  L  V  P  S  N  Q  V  V    V  Q  A  A 751  tctggcgatg tacaaacata ccaaattcgt acagcaccca ctagcaccat
     S  G  D    V  Q  T   Y  Q  I  R  T  A  P   T  S  T 801  cgcccctgga gttgttatgg catcctcccc agcacttcct acgcagcctg
     I  A  P  G  V  V  M   A  S  S   P  A  L  P  T  Q  P 851  ctgaagaagc agcccggaag agagaggttc gtctaatgaa gaacagggaa
     A  E  E    A  A  R  K  R  E  V   R  L  M    K  N  R  E 901  gcagcaagag aatgtcgtag aaagaagaaa gaatatgtga aatgtttaga
     A  A  R    E  C  R   R  K  K  K  E  Y  V   K  C  L 951  gaacagagtg gcagtgcttg aaaaccaaaa caagacattg attgaggagc
     E  N  R  V  A  V  L   E  N  Q   N  K  T  L   I  E  E 1001 taaaagcact taaggacctt tactgccaca aatcagatta aggatcc
     L  K  A    L  K  D  L  Y  C  H   K  S  D    - BamHI
```

Figure 12. Nucleotide coding sequence of hamster CREB-B cDNA (SEQ ID NO: 42). Cloning sites HindIII and BamHI are underscored.

```
   1  aagcttgccg ccaccatgac catggaatct ggagcagaca accagcagag
      HindIII         M    T  M  E  S  G  A  D    N  Q  Q 51  tggagatgct gctgtaacag aagctgaaaa tcaacaaatg acagctcaag
      S  G  D  A  A  V  T  E  A  E    N  Q  Q  M  T  A  Q 101  cccaaccaca gattgccaca ttagcccagg tatccatgcc agcagctcat
      A  Q  P    Q  I  A  T  L  A  Q  V  S  M    P  A  A  H 151  gcgacatcat ctgctccac  tgtaaccta  gtgcagctgc ccaatgggca
      A  T  S    S  A  P    T  V  T  L  V  Q  L  P  N  G 201  gacagtccaa gtccatggag ttattcaggc ggcccagcca tcagttattc
      Q  T  V  Q  V  H  G  V  I  Q    A  A  Q  P  S  V  I 251  agtctccaca agtccaaaca gttcagtctt cctgtaagga cttaaaaga
      Q  S  P    Q  V  Q  T  V  Q  S  S  C  K    D  L  K  R 301  cttttctccg gaactcagat ttcaactatt gcagaaagtg aggattcaca
      L  F  S    G  T  Q    I  S  T  I  A  E  S  E  D  S 351  ggaatctgtg gatagtgtaa ctgattccca aaagcgaagg gaaattcttt
      Q  E  S  V  D  S  V  T  D  S    Q  K  R  R  E  I  L 401  caaggaggcc ttcctccagg aaaatttga  atgacttatc ttctgatgca
      S  R  R    P  S  F  R  K  I  L  N  D  L    S  S  D  A 451  ccaggggtgc caaggattga agaagaaaag tcggaagagg agacttcagc
      P  G  V    P  R  I    E  E  E  K  S  E  E  E  T  S 501  ccctgccatc accactgtga cagtgccaac tccgatttac cagacaagca
      A  P  A  I  T  T  V  T  V  P    T  P  I  Y  Q  T  S 551  gtgggcagta tattgccatt acccagggag gagctataca gctggctaac
      S  G  Q    Y  I  A  I  T  Q  G  G  A  I    Q  L  A  N 601  aatggtaccg atggggtaca gggccttcag acattaacca tgaccaatgc
      N  G  T    D  G  V    Q  G  L  Q  T  L  T  M  T  N 651  agctgccact cagccgggta ccactattct acagtatgca cagaccactg
      A  A  T    Q  P  G    T  T  I  L  Q  Y  A  Q  T  T 701  atggacagca gattctagtg cccagcaacc aagttgttgt tcaagctgcc
      D  G  Q    Q  I  L  V  P  S  N  Q  V  V    V  Q  A  A 751  tctggcgatg tacaaacata ccaaattcgt acagcaccca ctagcaccat
      S  G  D    V  Q  T    Y  Q  I  R  T  A  P  T  S  T 801  cgcccctgga gttgttatgg catcctcccc agcacttcct acgcagcctg
      I  A  P  G  V  V  M  A  S  S    P  A  L  P  T  Q  P 851  ctgaagaagc agcccggaag agagaggttc gtctaatgaa gaacagggaa
      A  E  E    A  A  R  K  R  E  V  R  L  M    K  N  R  E 901  gcagcaagag aatgtcgtag aaagaagaaa gaatatgtga atgtttaga
      A  A  R    E  C  R    R  K  K  K  E  Y  V  K  C  L 951  gaacagagtg gcagtgcttg aaaaccaaaa caagacattg attgaggagc
      E  N  R  V  A  V  L  E  N  Q    N  K  T  L  I  E  E 1001  taaaagcact taaggacctt tactgccaca aatcagatta aggatcc
      L  K  A    L  K  D  L  Y  C  H  K  S  D    - BamHI
```

Figure 13. Nucleotide coding sequence of hamster CREB-B Y134F cDNA (SEQ ID NO: 43). Cloning sites HindIII and BamHI are underscored.

```
  1  aagcttactg ttggtaaagc cgccaccatg gaggcttggg agtgtttgga
     HindIII                       M  E  A  W  E   C   L 51  agattttttct gctgtgcgta acttgctgga acagagctct aacagtacct
     E  D  F  S   A  V  R   N  L  L   E  Q  S  S   N  S  T 101  cttggttttg gaggtttctg tggggctcat cccaggcaaa gttagtctgc
     S  W  F    W  R  F  L  W  G  S   S  Q  A    K  L  V  C 151  agaattaagg aggattacaa gtgggaattt gaagagcttt tgaaatcctg
     R  I  K    E  D  Y    K  W  E  F  E  E  L   L  K  S 201  tggtgagctg tttgattctt tgaatctggg tcaccaggcg cttttccaag
     C  G  E  L  F  D  S   L  N  L   G  H  Q  A   L  F  Q 251  agaaggtcat caagactttg gatttttcca caccggggcg cgctgcggct
     E  K  V    I  K  T  L  D  F  S   T  P  G   R  A  A  A 301  gctgttgctt ttttgagttt tataaaggat aaatggagcg aagaaaccca
     A  V  A    F  L  S   F  I  K  D  K  W  S    E  E  T 351  tctgagcggg gggtacctgc tggattttct ggccatgcat ctgtggagag
     H  L  S  G  G  Y  L   L  D  F    L  A  M  H  L  W  R 401  cggttgtgag acacaagaat cgcctgctac tgttgtcttc cgtccgcccg
     A  V  V    R  H  K  N  R  L  L    L  L  S    S  V  R  P 451  gcgataatac cgacggagga gcagcagcag cagcaggagg aagccaggcg
     A  I  I    P  T  E    E  Q  Q  Q  Q  Q  E    E  A  R 501  gcggcggcag gagcagagcc catggaaccc gagagccggc ctggaccctc
     R  R  R  Q  E  Q  S   P  W  N    P  R  A  G  L  D  P 551  gggaatgatc taga
     R  E  -    XbaI
```

Figure 14. Nucleotide coding sequence of E1b-19K (SEQ ID NO: 44). Cloning sites HindIII and XbaI are underscored.

```
        NcoI
  1  ccatggctca agctgggaga acagggtatg ataaccgaga gatcgtgatg
         M  A    Q  A  G  R  T  G  Y   D  N  R   E  I  V  M 51  aagtacatcc attataagct gtcacagagg ggctacgagt gggatgtggg
      K  Y  I   H  Y  K   L  S  Q  R   G  Y  E   W  D  V 101  agatgtggac gccgcggccg cggccgcgag ccccgtgcca cctgtggtcc
      G  D  V  D  A  A  A   A  A  A   S  P  V  P   P  V  V 151  acctgaccct ccgccgggct ggggatgact tctcccgtcg ctaccgtcgc
      H  L  T   L  R  R  A  G  D  D   F  S  R   R  Y  R  R 201  gacttcgcgg agatgtccag tcagctgcac ctgacgccct tcaccgcgag
      D  F  A   E  M  S   S  Q  L  H   L  T  P   F  T  A 251  gggacgcttt gctacggtgg tggaggaact cttcagggat ggggtgaact
      R  G  R  F  A  T  V   V  E  E   L  F  R  D   G  V  N 301  gggggaggat tgtggccttc tttgagttcg gtggggtcat gtgtgtggag
       W  G  R   I  V  A  F   F  E  F   G  G  V   M  C  V  E 351  agcgtcaaca gggagatgtc acccctggtg gacaacatcg ccctgtggat
       S  V  N   R  E  M   S  P  L  V   D  N  I   A  L  W 401  gaccgagtac ctgaaccggc atctgcacac ctggatccag gataacggag
       M  T  E  Y  L  N  R   H  L  H   T  W  I  Q   D  N  G 451  gctgggacgc atttgtggaa ctgtacggcc ccagtgtgag gcctctgttt
       G  W  D   A  F  V  E   L  Y  G   P  S  V   R  P  L  F 501  gatttctctt ggctgtctct gaagaccctg ctcagcctgg ccctggtcgg
       D  F  S   W  L  S   L  K  T  L   L  S  L   A  L  V 551  ggcctgcatc actctgggta cctacctggg ccacaagtga tctaga
       G  A  C  I  T  L  G   T  Y  L   G  H  K  -    XbaI
```

Figure 15. Nucleotide coding sequence of hamster Bcl2 deletion mutant (SEQ ID NO: 45). Cloning sites NcoI and XbaI are underscored.

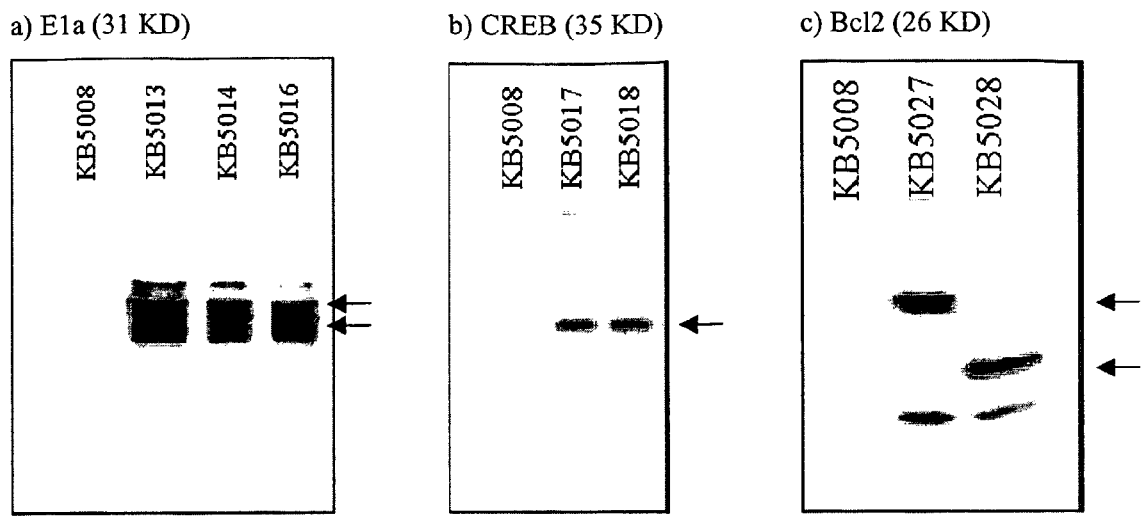
Figure 16. Western blots of E1a, CREB and Bcl2.
In a), b), and c), $1 \times 10^5$ CHO-K1 cells were transfected with 0.4 μg of indicated plasmid DNA. Cell lysates were collected after 48 hours and probed with appropriate antibodies. KB5008 transfected cells were used as negative controles.

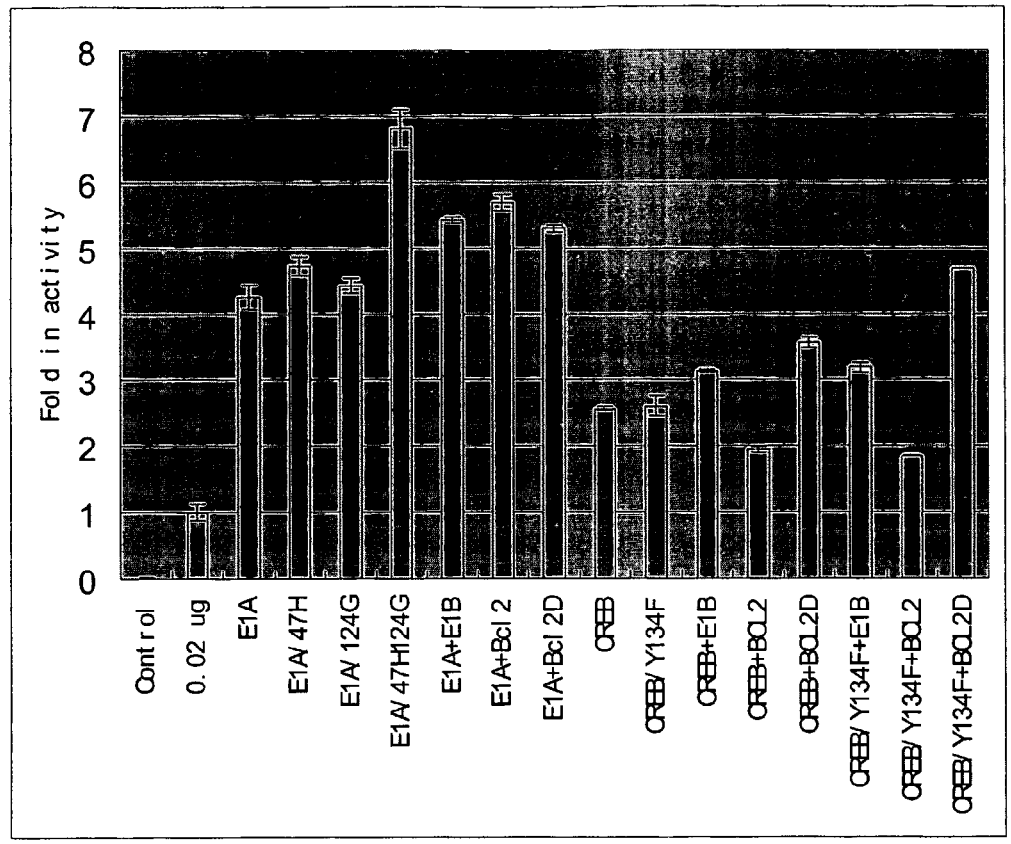

Figure 17. E1a and CREB enhanced CMV promoter in CHO-K1 cells.

$1 \times 10^5$ cells were transfected with 0.02 µg of SEAP reporter construct KB5019 and 0.2 µg of E1a or CREB expressing constructs. Total DNA was added up to 0.4 µg/well by control plasmid KB5008, E1b-19K or Bcl2 expressing plasmids. SEAP activities from culture media were assay 48 hours after transfection. The control was mock transfected CHO-K1 cells.

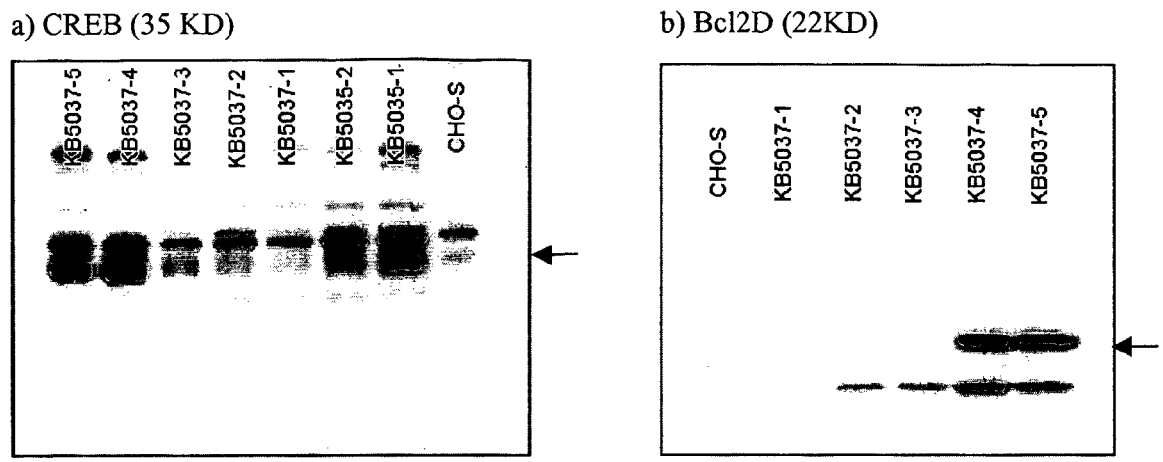
Figure 18. Western blots showing overexpression of hamster CREB-B Y134F and hamster ΔBcl-2 in stable transfectant CHO-S cell lines.

TRANSACTIVATION SYSTEM FOR MAMMALIAN CELLS

CROSS-REFERENCE TO RELATED APPLICATION

This application is the U.S. National Phase under 35 U.S.C. §371 of International Application No. PCT/US2004/043830, filed Dec. 30, 2004, which in turn claims priority to U.S. Provisional Application No. 60/533,917 filed Dec. 31, 2003, the entire disclosure of which is incorporated herein by reference.

FIELD OF THE INVENTION

The present invention relates to recombinant protein expression in a mammalian host cell. More specifically, the invention relates to the enhancement of recombinant protein production by reducing apoptosis in a population of cells that contain a recombinant transcriptional activator (transactivator) protein introduced into the cell to enhance gene expression of the recombinant protein.

BACKGROUND OF THE INVENTION

Recombinant engineered antibodies and other recombinant human glycoproteins are typically produced by transfection into mammalian cells of genes. Available expression systems for antibodies and other complex proteins generally involve the use of vectors that integrate into the host cell genome. These vectors typically integrate at essentially random sites in the genome and the level of expression is profoundly influenced by the site of integration and the chromatin structure at the site. This fact is generally regarded as limiting the maximum expression that can be achieved from each copy of the vector and leads to a great deal of variability in the productivity of different transfectant clones. The most efficient mammalian expression systems make use of a selectable marker that can be subjected to progressively more stringent selection conditions in order to select for transfectants that express at the highest possible levels from the integrated vector sequences or have undergone gene amplification. Increasing the number of vector copies at the site of integration typically leads to concomitant increase in the productivity of the cell line. Two such amplifiable markers have been widely used: dihydrofolate reductase (DHFR; see for example U.S. Pat. Nos. 5,179,017 and 6,455,275) and glutamine synthetase (G S; Bebbington et al (1992) Bio/Technology 10, 169-175; U.S. Pat. Nos. 5,591,693; 5,827,739; 5,770,359; 5,747,308; 5,122,464).

Cell-line development using such systems is time consuming and labor-intensive because of the need to screen a large number of transfectants to identify rare clones in which the vector has integrated into a favorable site in the genome for transcription. The available gene-amplification systems also suffer from the major drawback of being limited to use in a restricted number of cell-types. In practice, the DHFR system has been largely limited to use in DHFR-minus mutant CHO cells; and GS selection has been most widely used in the NS0 mouse myeloma line.

Other cell types may have advantages in terms of growth at large scale in simple defined culture media but their use is limited by the absence of efficient gene expression systems for these cells. Furthermore, different mammalian cell types show differences in the patterns of glycosylation of the glycoproteins that they secrete or in other post-translational modifications. Altering the carbohydrate structure of antibodies, for example, can have profound effects on biological activity. Thus there is considerable interest in using cell types with particular patterns of glycosylation for generating antibodies and other recombinant proteins with different biological activities.

Therefore, there is a need for a versatile expression system that could be used in different cell types and that permits more rapid cell-line development. In addition, production of recombinant human proteins and antibodies at commercial scale is costly and there is a continuing need to develop more cost-efficient manufacturing processes. One general approach to achieving increased yields of protein from fermentors is to generate increased cell biomass and to maintain cell viability for longer periods through modifications to the culture medium, feeding of nutrients and appropriate adjustments to oxygenation rates. An extension of this approach has been to engineer cells to better withstand environmental stress and so prolong viability and secretion of product.

High-Efficiency Expression Systems

A general approach to enhancing productivity of recombinant cell lines is to enhance the rate of protein production from each cell. There would be considerable advantages in enhancing productivity from single-copy genes such that efficient production could be achieved without the need for selection for vector amplification. If expression systems could be developed that provide highly efficient single-copy gene expression, these would provide improved yields in cell lines for which amplifiable vectors are not effective, as well as potentially providing improved yields from cell lines compatible with vector amplification. Efficient single-copy gene expression also provides the prospect of more rapid and reliable, and less labor-intensive cell line selection.

Accordingly, methods have been developed to target introduced vectors to particular sites in the genome of the host cell that are particularly favorable for gene expression. Such approaches have, in some instances, led to improved gene expression Examples of such an approach are provided in U.S. Pat. Nos. 5,648,267, 5,733,779, 6,017,733 and 6,159,730 pertaining to the NEOSPLA vector, and U.S. Pat. Nos. 5,830,698 and 5,998,144 pertaining to homologous recombination.

An alternative approach to ensuring efficient expression from vectors that integrate into the host cell genome has been to provide DNA elements on the vector that establish a favorable chromatin structure and insulate the genes of interest from chromosomal position effects. A number of genetic elements have been identified that may mitigate position effects in integrating vectors. It is now generally accepted that eukaryotic genomes are organized into chromatin domains containing individual genes or gene clusters sharing co-ordinate regulation in different tissues or developmental stages. Several kinds of DNA elements marking the boundaries of these domains have been identified including Matrix attachment regions (MARs, also called scaffold attachment regions, SARs); locus control regions (LCRs), ubiquitous chromatin opening elements (UCOEs; WO 00/05393; WO 02/081677; U.S. Pat. No. 6,689,606) and insulators (including sub-elements designated "barriers" Recillas-Targa et al (2002) Proc Natl Acad Sci USA. 99:6883-8). Of these, UCOEs and barriers are attractive elements that can function in a variety of cell types to isolate vector elements from position effects. UCOEs have been used for the production of recombinant antibodies in suspension-adapted CHO cells suitable for manufacturing (WO 02/099089; WO 02/099070). However, the yields currently attainable with these expression systems are not typically as high as can be attained using DHFR or GS-mediated vector amplification.

The use of transcriptional activator proteins ("transactivators") in combination with highly efficient promoters has also been explored. The Adenovirus E1a transactivator has been used in transfected CHO cells to increase expression levels directed from the human cytomegalovirus (hCMV) major immediate early (MIE) promoter-enhancer. This expression system has been used for expression of antibodies and other proteins (Cockett et al 1991 Nucl. Acids Res. 19:319-25, U.S. Pat. No. 5,866,359; U.S. Pat. No. 6,653,101; Bender et al 1993 Hum Antibodies Hybridomas. 4:74-9, each of these references is incorporated herein by reference). However, overexpression of E1a was correlated with cell toxicity. Subsequently, others have shown that Adenovirus E1 gene products can function to provide efficient expression in a human fetal retina-derived line PER.C6 although the levels of antibody reported do not achieve the highest levels attained by vector amplification in rodent cells (Jones et al (2003) Biotechnol Prog. 19:163-8). E1a also acts as a transactivator in the human embryonic kidney cell line HEK293, which is widely used at laboratory scale for transient transfection and has been used in the development of defective adenoviral vectors. However, this cell line does not seem suitable for large-scale growth in suspension culture. Furthermore, these and other expression systems still suffer from positional-dependent expression of recombinant proteins.

The E1a gene of Adenoviruses encodes two major proteins as a result of differential splicing. The proteins are characterized by their sedimentation coefficients (13S and 12 S) or their molecular size (289 and 243 amino acids, respectively, in Ad5) and are identical except for the presence of an additional "unique" region toward the C terminus of the 289 amino-acid protein (in one of three regions of the molecule, which are highly conserved between different strains of Adenovirus, designated conserved region 3). This region is required for transactivation and so only the 289 amino-acid form of E1a is a potent transactivator. The other conserved regions, CR1 and CR2 have been implicated in other functions of E1a in modulation of the cell cycle.

E1a proteins lack a sequence-specific DNA-binding activity, but modulate cellular gene expression by interacting with a diverse array of cellular factors, among them sequence-specific transcription factors, proteins of the general transcription machinery, co-activators and chromatin-modifying enzymes such as the histone acetylases, p300 and CBP (Ogryzko (1996) Cell 87:953-9).

E1a contains a minimum of four independent transactivation functions (reviewed by Frisch and Mymryk 2002 Nat Rev Mol Cell Biol 3, 441-52). The unique region and regions in exons 1 and 2 can each independently induce gene expression. Of the trans-activation pathways through which E1a acts, that involving CR3 is the most potent: most of the activation of viral early genes and of exogenous cellular genes by E1a is brought about by this region. CR3 alone is sufficient to activate transcription, as microinjection of a synthetic 49 residue peptide representing CR3 into HeLa cells activates expression (Lillie et al (1987) Cell 50:1091-1100). CR3 consists of two domains At its C-terminal end, residues 183-188 interact with a promoter-bound transcription factors, in this way recruiting E1a to a promoter. Once recruited, the activation domain in the N-terminal part of CR3, residues 141-178, containing a zinc finger, binds to the TATAA box binding protein, TBP, and activates transcription by stimulating the formation of a multi-protein transcription initiation complex with RNA polymerase II. Evidence suggests that the region of CR3 that binds TBP binds another cellular factor as well (reviewed by Frisch and Mymryk 2002 Nat Rev Mol Cell Biol 3, 441-52).

The mechanism for activation of the hCMV-MIE promoter-enhancer by adenovirus E1a has also been studied. In addition to activation of TATAA box associated transcription factors, the CR3 domain of the E1a protein is necessary for transactivation mediated by the 19 base-pair repeats in the CMV enhancer, which contain binding sites for the CREB/ATF family of transcription factors (Sanchez et al 2000 Am J Respir Cell Mol. Biol. 23:670-7). Certain ATF family members interact directly with the CR3 domain of E1a-289 (Chatton et al 1993 Mol Cell Biol. 13:561-70). The adenovirus E1a-associated cellular protein p300 also acts as a transcriptional cofactor that interacts with the repressor YY1 and mediates the relief of YY1 transcriptional repression by E1a. CREB has been shown to be modulated by E1a in a p300 binding-dependent manner (Lee et al 1996 J Biol Chem. 271:17666-74). This effect of E1a was correlated with a specific physical interaction between CREB and p300. Two separate domains within p300 were identified as capable of activating transcription. One of the domains interacted with the basal transcription factor TFIIB, indicating that p300 functions as a coactivator by making contacts with both CREB/ATF family members and the basal transcriptional machinery.

Despite the extensive characterization of E1a function, E1a transactivation has not been successfully applied to other cell types for the production of recombinant proteins. Its utility in mammalian cells has been limited because, in addition to its role in transcription, E1a is pro-apoptotic (White et al. 1991 J. Virol. 65: 2968-2978) and hence leads to early death of the host cell if expressed at high level. Apoptosis seems to be p53-dependent in human and rodent cells. Expression of adenovirus E1a protein deregulates normal cellular constraints on cell-cycle regulation by interacting with RB, with its relatives p107 and p130, and with the transcriptional co-activators p300 and CBP (Cuconati and White (2002 Genes and Development 16: 2465-2478). These activities activate apoptosis mediated by p53 (Debbas and White 1993 Genes Dev. 7: 546-554) a pathway that includes processing and activation of initiator procaspase-8, redistribution of cytochrome c, and activation of procaspase-3. Apoptosis is thought to be triggered primarily by binding of E1a to the retinoblastoma protein (RB). In the $G_0/G_1$ phase of the cell cycle, hypophosphorylated pRB complexes with transcription factors of the E2F family preventing their ability to activate transcription. Cell cycle dependent phosphorylation of pRB by cyclin/cdk complexes releases E2F to activate transcription of target genes required for S-phase of the cell cycle. Expression of E1a overrides the normal cellular control of the pRR-E2F interaction by binding hypophosphorylated pRB and releasing E2F. Among other effects the aberrant induction of E2F, leads to elevation of p53 levels and activation of the p53-dependent pro-apoptotic activity.

Apoptosis Protective Proteins

Apoptosis (programmed cell death) is a conserved cellular process that is required for normal development and is observed, in some instances, in cultured cell lines subject to environmental stresses such as serum-starvation, nutrient depletion or accumulation of toxic metabolites. However, cells in culture also die by an alternative, and less controlled process, necrosis. In the induction of apoptosis, numerous stimuli and signaling pathways converge to bring about the demise of the cell via activation of cysteine aspartic proteases (caspases), the key effectors of cell death. In one pathway of caspase activation, procaspase-9 is activated in a cytoplasmic protein complex known as the apoptosome by association with cytochrome c and other pro-apoptotic effector proteins released into the cytosol from the mitochondria. Mitochondrial release is, in turn, triggered by permeabilization of the mitochondrion by BAX or BAK proteins positively regulated by BID and BAD proteins at the surface of the mitochondrion. The activation of BID and BAD can be induced by the key regulator of the cell-cycle, p53. p53 responds to numerous signals relating to the transcriptional status of the cell by triggering apoptosis, cell-cycle arrest or cell proliferation.

In addition to activators of apoptosis, there are also multiple proteins within the cell that serve as checkpoints to restrict or prevent inappropriate apoptosis. In recent years the inhibitor of apoptosis (IAP) family of proteins have emerged as key inhibitors of the caspase cascade and thus represent central regulatory factors in apoptotic signaling. The IAPs, XIAP, cIAP-1, cIAP-2 and Survivin, can prevent caspase activation by blocking cytochrome c-induced activation of procaspase-9. Bcl-2 and Bcl-X(L) represent two additional apoptosis regulators that act upstream of the caspases to prevent BAX and BAK activation and hence limit apoptosis induction.

Anti-apoptotic genes have been introduced into cell lines expressing recombinant products in attempts to achieve prolonged maintenance of cell viability and hence increased yields of product. IAPs have been introduced into CHO cells and 293 cells and delayed cell death caused by depleted culture medium (Sauerwald T M, Betenbaugh M J, Oyler G A (2002) Biotechnol Bioeng. 77:704-16; Sauerwald T M, Oyler G A, Betenbaugh M J (2003) Biotechnol Bioeng. 81:329-40). Apoptosis-resistant CHO DUKX-B11 cells have been prepared by transfection of Bcl-2 (Lee and Lee (2003) Biotechnol. Bioeng. 82: 872-6). Bcl-2 has also been introduced into NS0 cells expressing a chimeric antibody that led to a modest (40%) increase in antibody titer (Tey et al 2000 J. Biotechnol. 79: 147-159). The activity of Bcl-2 is believed to be modulated by cleavage of a regulatory domain, the unstructured loop domain, present in both Bcl-2 and Bcl-X(L) (residues 32-80 in human Bcl-X(L); Chang et al (1997) EMBO J. 16:968-77). Deletion of this loop domain has been reported to lead to enhanced anti-apoptotic activity (Chang et al (1997) EMBO J. 16:968-77; Figueroa et al (2001) Biotechnol. Bioeng. 5: 211-222).

Adenoviruses generate a viral homologue of Bcl-2, the E1b-19K protein, which has a similar anti-apoptotic activity. E1b-19K has been transfected into recombinant NS0 cells and shown to increase productivity of an antibody under perfusion conditions (Mercille and Massie (1999) Biotechnol. Bioeng. 5: 529-543). However, no increase in product yield was seen as a result of E1b-19K expression if the same cell line was grown in a batch fermentation (Mercille, et al., Biotechnol. Bioeng. 63:516-528 (1999)). E1b-19K has also been evaluated alone and in combination with Aven in DHFR-minus CHO cells for delaying apoptosis in a host cell expressing the recombinant antibody IDEC-131 in a high vector copy-number, DHFR gene-amplification system (WO 03/006607). In this case a 20% increase in product yield was achieved using Aven and E1b-19K together. Such attempts to regulate cell death have had limited success, possibly in part because cells in culture can also respond to environmental stress by necrosis.

The modest increases in productivity demonstrated by delaying apoptosis in batch fermentations of mammalian cells are distinct from the teachings of the present invention, which use anti-apoptotic proteins as protective proteins to both permit the efficient expression of a transactivator in the same cell and prevent transactivator-induced apoptosis.

Adenoviral Protection Against Apoptosis

In cell lines transformed with large segments of adenoviral DNA, such as the human HEK 293 cell line, expression of other adenoviral gene products compensates for the pro-apoptotic effects of E1a to permit cell survival by interfering with p53-dependent apoptotic pathways. The E1b region encodes two proteins, E1b-19K and E1b-55K that interfere with different elements of the apoptosis pathways in cells. E1b-55K acts in concert with another adenoviral protein, E4-Orf6, to inactivate p53, while E1b-19K is a homologue of the cellular Bcl-2 protein and acts in a similar manner to Bcl-2 to regulate downstream mediators of apoptosis, particularly BAX and BAK. The E4 and E1b genes are both regulated by E1a and cellular transcription factors in human cells such that, in HEK293 cells, they are produced in sufficient quantity to inhibit apoptosis. In further dissection of these apoptosis pathway in human cells, co-expression of E1b-19K, Bcl-2 or RB has been shown to significantly inhibit E1a-mediated cell death (Putzer B M, Stiewe T, Parssanedjad K, Rega S, Esche H. (2000) Cell Death and Differentiation 7, 177-188; Cuconati and White (2002 Genes and Development 16: 2465-2478).

In primary cultures of rodent cells, E1a and E1b co-operate to permit oncogenic transformation. In these cells, E1a in the absence of E1b induces apoptosis in a p53-dependent manner. Indeed elevation of p53 expression is sufficient to induce apoptosis (Hale and Braithwaite (1999) J. Biol. Chem. 274: 23777-23786) and functional p53 is required for E1a-induced apoptosis primary rat kidney cells (Lowe and Ruley (1993) Genes Dev. 7: 535-545; Debbas and White (1993) Genes Dev. 7: 546-554).

The effects of adenoviral proteins on cellular signaling pathways in permanent established rodent cell lines, such as those used for production of recombinant proteins, have not been extensively studied. Nevertheless, there are several indications of fundamental differences between the control of cellular proliferation and apoptosis in primary cells and established cell lines. Thus primary cells respond to adjacent cell contact by growth arrest (a phenomenon known as "contact inhibition" of cell proliferation). In contrast, established cell lines are typically not sensitive to contact inhibition. E1b has been shown to influence apoptotic pathways in only some cell lines (such as NS0) and not, for example, in hybridomas derived from NS0 (Mercille et al (1999) Biotechnol Bioeng. 63:516-528), indicating that pathways of cell growth-regulation differ in different cell lines.

The p53 protein is a critical regulator of the cell cycle in normal cells and is frequently mutated and hence defective in oncogenically transformed cells and cultured cell lines. As described above, p53 is also a key mediator of E1a-induced apoptosis in primary rodent cells and in productive adenoviral infections in human cells. However, the fact that p53 may be defective in many established cell lines suggests that responses to E1a will be different in such cells. Thus, for example the Chinese hamster ovary cell line CHO-K1 has a mutation in codon 211 of the p53 gene leading to a protein with mutant function, abnormally high-level expression and lacking normal cell-cycle control function at the $G_1$ checkpoint (Hu et al (1999) Mutation Res. 426: 51-62).

E1a has also been transfected into CHO cells for enhancing recombinant gene expression. Substantial cell killing due to E1a expression was noted in this case, although the pathways leading to apoptosis have not been fully characterized. Thus careful titration of the level of E1a expression is required in CHO cells in order to select cell lines that have sufficient E1a for transactivation but low enough levels not to interfere unduly with cell survival and proliferation. Methods for accomplishing this are described in U.S. Pat. Nos. 5,866,359 and 6,653,101. The present invention provides improved methods for transactivation that allow efficient expression of a recombinant protein under control of a transactivator in mammalian cell lines and provides protection from transactivator-mediated apoptosis, regardless of the level of E1a expression.

In the early studies, human primary embryonic kidney cell cultures were transformed using sheared Adenovirus DNA (from Ad5). Although the adenoviral DNA inserted into the genome of HEK-293 cells is poorly characterized, the HEK-293 cell line isolated from this transformation process has been shown to contain viral DNA homologous to the leftmost 12% and to the rightmost 10% of the Ad5 genome, and to express E1a and E1b, among several other adenoviral proteins (Jochemsen et al 1981 J. Virol. 37:530), under the control of the natural adenoviral E1a and E1b promoters. The HEK-293 cells are generally unsuitable for robust, large scale recombinant protein expression.

Additional human primary cell cultures transformed with adenoviral DNA have also been described. PER cell lines (Fallaux et al 1998 Hum Gene Ther. 1998 Sep. 1; 9 (13):1909-17) were generated by transformation and immortalization of human primary embryonic retinal cells with cloned fragments of adenoviral genome. This was done in order to generate helper cell lines to support the replication of defective adenoviral vectors and, specifically, to prevent the formation of replication-competent adenovirus by recombination between the adenoviral vector and adenoviral DNA present in the host cell, seen in HEK-293 cells. PER cells (such as clone PER.C6) contain the Ad serotype 5 (Ad5) E1A- and E1B-encoding sequences (Ad5 nucleotides 459-3510) under the control of the human phosphoglycerate kinase (PGK) promoter. Thus the use of fragments of adenoviral genomes to transform and immortalize human primary cell cultures to generate permanent cell lines capable of sustained growth in tissue culture is well established.

In both PER.C6 and HEK-293 cells, the E1b-19K gene is transcribed from a promoter downstream from the E1a gene. However in such an arrangement, the use of upstream promoters interferes with transcription from a downstream promoter in mammalian cells, thereby diluting or obviating the protective benefits of the E1b-19K encoded anti-apoptotic protein on transactivator-induced apoptosis. For the purposes of polypeptide expression, these cells are also difficult to grow in suspension and in high cell density. It is an object of the present invention to provide compositions and methods for recombinant polypeptide expression in established mammalian cell lines through the combined efficient expression of a transactivator protein and the efficient and adequate expression of an apoptosis protective protein in order to prevent transactivator-induced apoptosis.

SUMMARY OF THE INVENTION

It is an object of the invention to provide methods and compositions for expressing a recombinant protein within a mammalian host cell using a co-expressed transcriptional activator. It is a further object of the invention to minimize or prevent adverse effects of the transactivator on host cell survival and proliferation.

One aspect of the invention provides vector systems for transfection and recombinant polypeptide expression in a mammalian host cell comprising (a) a first cistron encoding a transactivator under control of a first promoter and (b) a second cistron encoding an apoptosis-protective protein under the control of the first promoter or optionally under the control of a second promoter. In another embodiment the invention provides a third cistron encoding at least one desired polypeptide under control of a third promoter, wherein said third promoter is responsive to the transactivator protein. The vector system optionally includes a fourth cistron encoding at a second desired polypeptide under control of a promoter that is responsive to the transactivator protein. Alternatively, the vector system comprises a fourth cistron under control of the third promoter. In some embodiments the third and fourth cistrons are separated by a internal (IRES) element. In addition to the first and second citrons, the invention also provides a vector system further comprising a library of cistrons, with each cistron encoding a desired recombinant polypeptide.

The vector system can contain the first, second and third cistrons in separate vectors, in two vectors (one containing a single cistron and the second containing two), or in a single vector containing all three cistrons.

In some embodiments, the transactivator and the apoptotic protective protein are homologous to the endogenous transactivator and apoptotic protective proteins of the host cell.

In a preferred embodiment the first cistron encodes an adenoviral E1a protein or a variant thereof, more preferably an E1a protein from human Ad2, Ad5 or Ad12. In some embodiments, the invention provides cistrons encoding E1a 13s proteins. In still other embodiments the cistrons encode an adenoviral E1a polypeptide comprising a mutation in CR1 such as Y47H. In another preferred embodiment, the transactivator is CREB and the third promoter comprises a CREB-binding element. In yet another embodiment the transactivator is a hamster derived CREB, a CREB variant, or a CREB variant having a Y134F mutation.

The first and second promoters of the invention independently include for example, a strong, efficient heterologous promoter, a cytomegalovirus promoter, a SV-40 Early or Late promoter, or a RSV-LTR promoter. In other embodiments the first or second promoter is not a phosphoglycerate kinase promoter, a E1a promoter, or a E1b promoter. The third promoter includes for example, a CREB-binding element, a 19 bp repeat from a hCMV-MIE enhancer, a promoter having a TATAA transcription initiation signal, or a hCMV-MIE promoter having a TATAA box region.

In another embodiment the invention provides a kit containing one or more of the cistrons of the invention. In some embodiments the kit contains the first and the second cistron encoding the respective transactivator and apoptotic protective proteins. In still other embodiments the kit further contains instructions for using the cistrons to express recombinant proteins or a library of recombinant proteins.

Another aspect of the invention provides methods of expressing or enhancing the yield of a desired recombinant protein in a mammalian host cell comprising introducing into the mammalian cell: (a) a first cistron encoding a transactivator under control of a first promoter, (b) a second cistron encoding an apoptosis-protective protein under the control of the first promoter or optionally under the control of a second promoter, and (c) a third cistron encoding a desired polypeptide under control of a third promoter, wherein said third promoter is responsive to the transactivator protein. Preferably, expression of the transactivator protein under control of the first promoter in the absence of the apoptosis-protective protein would cause significant cell death and expression of the apoptosis-protective protein prevents cell-killing due to expression of the transactivator. In one embodiment, the invention provides a method of linearizing a plasmid containing a transactivator protein and an apoptosis protective protein such that the apoptosis protective protein is transcribed upstream of the transactivator protein after integration into the host chromosome.

The first, second and third cistrons can be introduced to the host cell on the same or separate vectors. Additionally, one or two cistrons can be introduced into the host cell line and the other cistron(s) introduced subsequently. In yet other embodiments the method of the present invention is used to individually express multiple polypeptides for the purpose of generating a library of polypeptides.

In a preferred embodiment, the mammalian host cell is selected from the group consisting of a CHO cell, a mouse myeloma cell, a mouse hybridoma cell, a rat myeloma cell, and a rat hybridoma cell. In other embodiments, the mammalian cell is a non-human mammalian cell. The host cells provided by the invention also include cells capable of growing in suspension. In some embodiments the host cell is a CHO-S cell. In other embodiments the host cell is a YB2/0 rat hybridoma cell.

Yet another aspect of the invention provides mammalian host cells comprising a first cistron encoding a transactivator, a second cistron encoding an apoptosis-protective protein that prevents cell-killing due to expression of the transactivator, and a third cistron encoding one or more desired proteins under the control of a promoter responsive to the transactivator. In a preferred embodiment, the transactivator is expressed from an efficient heterologous promoter at a level that, in the absence of the protective protein, causes significant cell death. In some embodiments, the invention provides a non-human mammalian host cell. An aspect of the invention also provides methods for producing a recombinant protein comprising culturing the mammalian host cells in a suitable medium such that the desired protein(s) is secreted into the medium.

A further aspect of the invention provides mammalian host cells comprising a cistron encoding a variant E1a protein and a cistron encoding a recombinant protein under the control of an activatable promoter, wherein the E1a protein retains transactivation activity but is defective in the ability to trigger apoptosis. Preferably, the variant E1a comprises a point mutation in the N-terminal region (which includes the N-terminal portion of E1a, up to and including CR1) that inhibits binding to retinoblastoma protein (RB).

Yet another aspect of the invention provides methods of expressing a desired polypeptide in a mammalian host cell comprising introducing into the mammalian host cell (a) a first cistron encoding a variant E1a protein under control of a first promoter, wherein the E1a protein retains transactivation activity but is defective in the ability to trigger apoptosis and (b) a second cistron encoding a desired polypeptide under control of a second promoter, wherein said second promoter is responsive to the transactivator protein. In a preferred embodiment, this method further comprises introducing into the host cell a third cistron encoding an apoptosis-protective protein.

In some embodiments of the vectors, methods, and host cells of the invention, when the first or second promoter is a phosphoglycerate kinase promoter, an E1a promoter, or an E1b promoter, then the first cistron does not lie immediately upstream of the second cistron. In other embodiments the first and second cistrons are on one vector and are separated by a transcriptional terminator.

In still other embodiments, the invention provides vectors, host cells, and methods for producing polypeptides in quantities of greater than 10, 20, 30, 40, 50, 60, 70, 80, 90, or 100 pg/cell/day.

The polypeptides of the vector systems, methods, and host cells of the invention include, but are not limited to, cytokines, growth hormones, antibodies or antibody fragments, single-chain antibodies, and fusion proteins. In one aspect of the invention, the polypeptides are part of a library of polypeptides.

Apoptosis protective proteins of the vector systems, methods, and host cells of the invention include, for example, the E1b-19K protein, a protein that interacts with BAX, a protein that interacts with BAK, Bcl-2, Bcl-X(L), a Bcl-2 protein having a deletion in the regulatory loop region, an inhibitor of apoptosome formation, a downstream apoptosis inhibitor, retinoblastoma (RB) protein, and a p53 mutant protein that acts as a dominant negative mutant and abrogates the activity of wild-type p53.

In some embodiments of the vector systems, methods, and host cells of the invention, the cistrons encoding the polypeptides of the invention are associated with a ubiquitous chromatin opening element (UCOE), an insulator, a barrier element, an intron, a polyadenylation signal, a 5' untranslated region, or a signal peptide. In other embodiments the ubiquitous chromatin opening element comprises a hnRNP A2 promoter. In still other embodiments the ubiquitous chromatin opening element comprises an extended methylation-free CpG-island or a 16 kb DNA fragment spanning the human hnRNP A2 gene with 5 kb 5' and 1.5 kb 3' flanking sequences or a functional homologue or fragment thereof.

BRIEF DESCRIPTION OF THE FIGURES

For a better understanding of the nature and objects of some embodiments of the invention, reference should be made to the following detailed description taken in conjunction with the accompanying drawings, in which:

FIG. 1 provides the amino acid sequence of hamster Bcl-2 (SEQ ID NO: 1).

FIG. 2 provides the amino acid sequence of hamster ΔBcl-2 (SEQ ID NO: 2).

FIG. 3 provides the nucleotide sequence of the hamster ΔBcl-2 cDNA open reading frame (SEQ ID NO: 3).

FIG. 4 provides the amino acid sequence of E1a-289R pm47/124 protein (SEQ ID NO: 4).

FIG. 5 provides the nucleotide sequence of E1a pm47/124 coding region (SEQ ID NO: 5).

FIG. 6 provides the nucleotide sequence of E1b-19K coding sequence spanning the EcoR1 site to the Sal1 site (SEQ ID NO: 15).

FIG. 7 (FIG. 7A-7D) provides the nucleotide (SEQ ID NO: 18) and deduced amino acid sequence (SEQ ID NO: 19) of human RB coding sequence cloned between Sal1 and Not1 restriction sites.

FIG. 8 (FIG. 8A-8B) provides the nucleotide (SEQ ID NO: 20) and deduced amino acid (SEQ ID NO: 21) sequence of variant rat CREB-B coding sequence cloned between EcoR1 and Sal1 sites. The single point mutation at nucleotide 374 is underlined and the resulting Y134F amino acid substitution is shown in bold.

FIG. 9 provides maps of KB5008, pGL3-Control, KB5029, and KB5032. KB5008 carries a RSVLTR (SEQ ID NO: 54) promoter and was used to clone E1a and CREB. pGL3-Control carries a SV40 promoter and was used to clone. E1b-19K and Bcl2. KB5029 carries the double expression cassettes for E1a and E1b-19K. KB5032 carries the double expression cassettes for CREB and Bcl2.

FIG. 10 provides the nucleotide coding sequence of E1a cDNA (SEQ ID NO: 40). The amino acid sequence in FIG. 10 is disclosed as SEQ ID NO: 48.

FIG. 11 provides the nucleotide coding sequence of E1 A mutant Y47H (SEQ ID NO: 41). The amino acid sequence in FIG. 11 is disclosed as SEQ ID NO: 49.

FIG. 12 provides the nucleotide coding sequence of hamster CREB-B cDNA. Amino acid residue Y134 is underscored (SEQ ID NO: 42). The amino acid sequence in FIG. 12 is disclosed as SEQ ID NO: 50.

FIG. 13 provides the nucleotide coding sequence of hamster CREB-B mutant Y134F (SEQ ID NO: 43). The amino acid sequence in FIG. 13 is disclosed as SEQ ID NO: 51.

FIG. 14 provides the nucleotide coding sequence of E1b-19K (SEQ ID NO: 44). The amino acid sequence in FIG. 14 is disclosed as SEQ ID NO: 52.

FIG. 15 provides the nucleotide coding sequence of hamster Bcl2 deletion mutant Bcl2D (SEQ ID NO: 45). The amino acid sequence in FIG. 15 is disclosed as SEQ ID NO: 53.

FIG. 16 provides Western blots of E1a, CREB, and Bcl2.

FIG. 17 shows CMV promoter activity enhanced by E1a and CREB in CHO-K1 cells determined using a SEAP reporter gene assay.

FIG. 18(A-B) provides Western blots of hamster CREB-B Y134F and hamster Bcl2D from stable CHO-S transfectant cell lines.

DETAILED DESCRIPTION OF THE INVENTION

The present invention is directed generally to compositions and methods for enhancing expression of desired proteins by a mammalian host cell using a co-expressed transcriptional activator. In particular, the invention provides vectors, host cells and methods of expressing at least one desired polypeptide by introducing into a mammalian host cell cistrons encoding a transactivator, a desired polypeptide and an apoptosis-protective protein. The invention also provides vectors, host cells and methods of expressing desired polypeptides by stably introducing into a mammalian host cell a cistron encoding a variant E1a protein that retains transactivation activity but is defective in the ability to trigger apoptosis.

DEFINITIONS

The term "cistron" refers to a specific sequence of nucleotides that encodes one or more polypeptide(s). More than one cistron may be transcribed from a single promoter.

As used herein, the term "variant," as it applies to a polynucleotide refers to a polynucleotide sequence that differs from the corresponding wild type at one or more nucleotides. Polypeptide "variant," as the term is used herein, is a polypeptide that typically differs from a wildtype polypeptide sequence in one or more substitutions, deletions, additions and/or insertions. For example, certain illustrative variants of the polypeptides of the invention include those in which one or more portions, such as an N-terminal leader sequence or flexible loop region, have been removed. Other illustrative variants include variants in which a small portion (e.g., 1-30 amino acids, preferably 5-15 amino acids) has been removed from the N- and/or C-terminal of the mature protein. Such polynucleotide or polypeptide variants may be naturally occurring or may be synthetically generated, for example, by modifying one or more of the above polypeptide sequences of the invention and evaluating their immunogenic activity as described herein and/or using any of a number of techniques well known in the art.

The term "transactivator," as used herein, refers to a recombinant polypeptide product that interacts, directly or indirectly, with a region associated with a promoter, thereby turning on (activating) transcription of a structural gene.

The term "defective in the ability to trigger apoptosis" refers to a characteristic of a variant transactivator that when expressed from a vector under the control of a CMV promoter decreases transfection efficiency by no more than 90% as compared to transfection of a control vector containing no transactivator. Preferably, the variant transactivators of the invention will decrease transfection efficiency by no more than 50%.

The term "apoptosis-protective protein," as used herein refers to a polypeptide product that, when expressed, decreases the frequency of transactivator mediated apoptosis in a population of cells.

"Isolated," as used herein in reference to nucleotides, means that a polynucleotide is substantially away from other coding sequences, and that a DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man. An "isolated" polypeptide is one that is removed from its original environment. For example, a naturally-occurring protein or polypeptide is isolated if it is separated from some or all of the coexisting materials in the natural system.

As used herein, the terms "protein" and "polypeptide" are used in their conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring.

Expression Systems of the Invention

The invention provides improved methods for the activation of transcription from activatable cistrons by a transcriptional activator in a mammalian host cell that minimize or prevent adverse effects of the transactivator on cell growth and survival.

The activatable cistron or cistrons are expressed from one or more promoters responsive to the transactivator. Examples include promoters or enhancers containing CREB-binding elements or the 19 bp repeat from the hCMV-MIE enhancer and promoters containing the TATAA transcription initiation signal. Preferred enhancers are cytomegalovirus enhancers such as the enhancer from the hCMV-MIE gene or the mouse CMV-MIE gene. A preferred promoter is the TATAA box region of the hCMV-MIE promoter. The activatable promoters are used to direct transcription of genes encoding recombinant protein products.

Transactivators of the invention are polypeptides that enhance the expression of a desired gene by interacting directly or indirectly with nucleic acid sequences that are located in cis to the desired gene. The activator of the invention is a protein that serves to activate transcription of an activatable cistron when expressed in a host cell but that shows adverse effects on host cell growth and survival when expressed in its normal or unmutated form at wildtype levels. In one embodiment, the transactivator of the invention is a protein that serves to activate transcription from an activatable control region in a host cell but that shows adverse effects on host cell growth and survival when expressed in its normal or unmutated form. The transactivators of the invention can be homologous or heterologous to the normal transactivator of the host cell. Examples of such transactivators include E1a proteins from adenoviruses and mammalian proteins that are components of signal transduction pathways, including mammalian p53, c-myc and cyclic-AMP response-element binding proteins (CREBs). Preferably, the homologous transactivator protein is derived from the host cell species. In one embodiment, the invention provides a hamster CREB derived from a hamster cell line.

A preferred activator of the invention is an E1a activator from an adenovirus such as a human, monkey or rodent adenovirus. Preferred examples include E1a from human Ad2, Ad5 and Ad12. The E1a activator contains an activation domain such as that present in the 289 amino acid Ad5 E1a protein. Specific preferred E1a proteins are the E1a 13S proteins. The E1a protein may also be a variant E1a protein and contain point mutations or deletions. A preferred variant E1a protein is the Y47H mutant of Ad5. In one embodiment the Y47H mutant comprises Seq. ID NO: 41 or a variant thereof. Another preferred variant is an E1a variant having a mutation in CR1.

In another embodiment, the invention provides CREB proteins and variants thereof. Preferred CREB proteins include those derived from hamsters. Preferred variants include the CREB variant Y134F. In some embodiments, the CREB variant comprises Seq. ID. NO: 43 or a variant thereof. CREB proteins activate transcription of promoters containing DNA sequences known as cyclic-AMP response elements (CREs) and typically do so in response to cAMP-mediated signal transduction involving phosphorylation of CREB protein by cAMP-activated Protein Kinase A. A constitutively active mutant CREB has been characterized, which does not require cAMP-mediated signal-transduction to activate promoters containing CREs (Du et al (2000) Mol. Cell. Biol. 20: 4320-4327). However, the practical utility of CREB as an activator protein is limited since overexpression of CREB proteins has been shown to induce apoptosis in several cell lines (Saeki et al (1999) Biochem. J. 343: 249-255). Similarly, p53 regulates the expression of numerous genes and its overexpression induces apoptosis (Yonish-Rouach et al (1993) Mol. Cell. Biol. 13: 1415-1423; Yonish-Rouach et al (1995) Oncogene 11: 2197-205). The present invention overcomes this constraint Apoptosis Protective Proteins One embodiment of the invention provides methods of enhancing transcription of a cistron within a mammalian host cell comprising introducing into a mammalian host cell (a) a first cistron encoding a transactivator under control of a first promoter, (b) a second cistron encoding an apoptosis-protective protein, and (c) a third cistron encoding a desired polypeptide under control of a third promoter, wherein said third promoter is responsive to the transactivator protein. Preferably, expression of the transactivator protein under control of the first promoter in the absence of the apoptosis-protective protein would cause significant cell death and expression of the apoptosis-protective protein prevents cell-killing due to expression of the transactivator.

The apoptosis-protective protein of the invention serves to prevent transactivator-mediated cell death. Examples of suitable proteins include a target to which E1a binds and that initiates a pro-apoptotic signaling cascade such as the retinoblastoma (RB) protein. Alternatively the protective protein may be a downstream inhibitor of E1a-stimulated cell killing such as an anti-apoptotic protein. An example of a suitable anti-apoptotic protein is a mutant p53 protein that acts as a dominant negative mutant and abrogates the activity of the wild-type p53. Other suitable anti-apoptotic proteins include proteins that interact with BAX or BAK and inhibit their activity, such as Bcl-2, Bcl-X(L) or an adenovirus E1b-19K protein. Alternative anti-apoptotic proteins include an inhibitor of apoptosome formation such as Aven, or a downstream apoptosis inhibitor such as IAP or survivin. Preferably the anti-apoptotic protein is a cellular protein from a species related to that of the host cell, such as a hamster or rodent protein. Particularly preferred protective proteins are the variant Bcl-2 protein that has a deletion in the regulatory loop domain or a hamster derived Bcl-2.

Most preferably, the protective protein is a variant hamster Bcl-2 deleted of the loop domain. FIG. 1 shows the sequence of a hamster Bcl-2 protein (Genbank AJ271720) and FIG. 2 provides a novel deletion mutant, hamster ΔBcl-2 in which the loop domain is replaced by a sequence of 4 alanine residues. The nucleotide sequence of the hamster ΔBcl-2 is shown in FIG. 3.

The protective protein of this aspect of the invention is expressed in an expression vector allowing appropriate expression in the mammalian host cell. Preferably the protective protein is expressed from an efficient heterologous promoter such as a SV40, RSV or CMV promoter. If the protective protein is E1b-19K, it is preferred that the E1b-19K coding sequence is under the control of a non-adenoviral promoter.

The combination of transactivator, protective protein, and activatable cistron in the same cell leads to significant increases in productivity of the activatable cistron. Preferably the specific production rate (production rate per cell) is enhanced at least two-fold by the combination of the transactivator and the protective protein. More preferably, the specific production rate is enhanced at least five-fold.

Variant Transactivator Proteins

In addition, the invention also provides methods of expressing a desired polypeptide in a mammalian host cell comprising introducing into a mammalian host cell: (a) a first cistron encoding a variant E1a protein under control of a first promoter, wherein the variant E1a protein retains transactivation activity but is defective in the ability to trigger apoptosis and (b) a second cistron encoding a desired polypeptide under control of a second promoter, wherein said second promoter is responsive to the transactivator protein. This aspect of the invention also includes mammalian host cells comprising a first cistron encoding a variant E1a protein that is defective in apoptosis induction, and a second cistron encoding a desired polypeptide under the control of an activatable promoter, preferably wherein the host cell is not a human cell.

The E1a protein of this aspect of the invention retains the transactivation activity of E1a-289 but is defective in binding to the retinoblastoma protein and thereby permits cell survival and proliferation. Sequences required for RB binding have been described (for example see Shisler et al 1996 J. Virol 70: 68-77). Two regions of the E1a protein interact with RB, a region at the N-terminus, encompassing sequences in CR1, and a distinct site in CR2. Suitable mutations that inactivate RB binding are deletions or point mutations in the RB-binding sites in the N-terminal/CR1 region of E1a and in the CR2 region, e.g. deltaCR2 (Samuelson and Lowe (1997) Proc. Natl. Acad. Sci. 94: 12094-12099). In a particularly preferred embodiment of this aspect of the invention, the E1a transactivator is a E1a-289 protein that retains regions of the molecule required for p300 binding but that is defective in RB binding. Most preferably, the variant E1a has mutations in either one or both of the two regions that bind RB. An example is the deletion of residues 26-35 and 111-123 (Shisler et al 1996 J. Virol 70: 68-77). Another example is the combination of two point mutations: changing tyrosine to histidine at amino acid 47 (47H) and cysteine to glycine at residue 124 (124G) (pm 47/124; Samuelson and Lowe 1997 Proc. Natl. Acad. Sci. 94: 12094-12099). The sequence of Ad5 E1a pm47/124 is shown in FIG. 4 and the nucleotide sequence in FIG. 5 (in which the mutated residues are underlined). The nucleotide sequence contains an intron that is differentially spliced to generate both the 243 and 289 amino-acid forms of E1a (E1a-243R and E1a-289R). Only the 289 amino-acid form is a potent transactivator.

Additionally, the E1a protein may be modified at its N-terminus to increase the protein's stability. For example deletion of arginine at amino acid 2 or deletion of the first 14 residues may lead to the production of a more stable protein (Slavicek et al (1988) EMBO J. 7:3171-80).

In an alternative embodiment of this aspect of the invention, the variant E1a protein is a novel variant protein identified by screening or selecting a variant E1a defective in RB binding from a plurality of variant E1a proteins. A library of variant E1a proteins can be generated and screened in a microbial expression system for binding to RB. The library of variant E1a proteins is preferably a focused library in which sequence variation is restricted to particular regions of the E1a molecule. More preferably, mutations are restricted to the N-terminal (including CR1) and CR2 regions of E1a. For illustration, the library of variant E1a proteins may be expressed in *E. coli* as a fusion protein with a bacterial beta-lactamase and variants defective in RB binding selected using an in vitro selection system. For this purpose, RB protein or a fragment of RB capable of binding to wildtype. E1a may be co-expressed with the E1a variant library. The RB fragment is co-expressed, for example, as a fusion protein with an inhibitor of beta-lactamase such as a BLIP protein and defective E1a variants are selected by their ability to prevent BLIP-fusion protein associating with beta-lactamase. In this way, *E. coli* cells containing a defective E1a are able to grow in the presence of the antibiotic ampicillin whereas cells containing E1a capable of binding RB are killed by this concentration of ampicillin. An example of a suitable BLIP protein is the BLIP from *Streptomyces clavuligerus* (Strynadka et al (1994) Nature 368: 657-660). The RB protein can be fused to either the carboxy- or amino-terminus of BLIP via a peptide linker such as a peptide of the sequence (Gly-Gly-Gly-Gly-Ser) (SEQ ID NO: 55) also designated (Gly4-Ser) (SEQ ID NO: 55) or multiples thereof. An example of a beta-lactamase protein is a masked beta-lactamase described in WO/03/069312. The E1a protein is fused to the N- or C-terminus of beta-lactamase by a Gly4-Ser (SEQ ID NO: 55) linker peptide The masked beta-lactamase has reduced affinity for BLIP and binds BLIP detectably only in the presence of associated RB and E1a.

A polypeptide "variant," as the term is used herein, is a polypeptide that typically differs from its wildtype counterpart in one or more substitutions, deletions, additions, and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics, e.g., with the ability to transactivate transcription. When it is desired to alter the amino acid sequence of a polypeptide to create an equivalent, or even an improved variant or portion of a polypeptide, one skilled in the art will typically change one or more of the codons of the encoding DNA sequence according to Table 1.

For example, certain amino acids may be substituted for other amino acids in a protein structure without appreciable loss of interactive binding capacity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

TABLE 1

| Amino Acids | 3-letter | 1-letter | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

TABLE 1-continued

| Amino Acids | 3-letter | 1-letter | Codons |
|---|---|---|---|
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.01±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein or a protein with similar functional characteristics. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, tip, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Variant E1a genes according to this aspect of the invention, originating from the library of variants expressed in E. coli or from another source, can be introduced into mammalian expression vectors and expressed in mammalian host cells from a promoter that is active in the chosen host cell. Preferably the promoter used is an efficient heterologous promoter such as a RSV-LTR promoter or a cytomegalovirus promoter.

Preferably, the host cell is an established cell line, capable of indefinite proliferation in cell culture in vitro. Most preferably the host cell is an established rodent cell such as a CHO cell (e.g. CHO-S, DG44, DUKX-B11, CHO-K1), a mouse myeloma or a hybridoma cell (e.g. NS0, SP2/0), or rat myeloma or hybridoma line (e.g. YB2/0). The host cell line comprises a cistron encoding the variant E1a protein and a cistron for a recombinant protein under the control of an activatable promoter. The two cistrons can be introduced to the host cell on the same or separate vectors. The cistrons can be introduced to the host cell by any of the methods widely known in the art including electroporation, calcium-phosphate co-precipitation, cell fusion and cationic lipid mediated transfection. At least one selectable marker gene may be included in order to select for stable integration of plasmid DNA into the host cell genome. The selectable marker can be on the same plasmid as the transactivator cistron or the activatable cistron or on a separate plasmid or DNA fragment. For transfection of CHO cells such as CHO-S, numerous methods are known in the art. A particularly suitable method is cationic lipid-mediated transfection, for example using lipofectamine (Invitrogen) according to the manufacturer's instructions. For myeloma and hybridoma cell lines, electroporation is a preferred method for transfection. For example, rat YB2/0 cells can be successfully transfected by electroporation (Shinkawa et al (2003) J. Biol. Chem. 278: 3466; Shitara et al (1994) J. Immunol. Methods 167: 271). Murine NS0 cells can also be transfected by electroporation (Bebbington et al (1992) Biotechnology 10 (2): 169-75).

Additional elements may be included with the activatable gene to ensure appropriate high-level expression, including ubiquitous chromatin opening elements UCOE, insulators, barrier elements, introns, polyadenylation signals, 5'-untranslated regions and signal peptides.

The UCOE of the present invention can be any element, which opens chromatin or maintains chromatin in an open state and facilitates reproducible expression. Use of UCOE provides an advantage over other expression systems that are positional dependent. In a preferred embodiment, the UCOE comprises an extended methylation-free, CpG-island. CpG-islands have an average GC content of approximately 60%, compared with a 40% average in bulk DNA. One skilled in the art can easily identify CpG-islands using standard techniques such as using restriction enzymes specific for C and G sequences. An extended methylation-free CpG island is a methylation-free CpG island that extends across a region encompassing more than one transcriptional start site and/or extends for more than 300 bp and preferably more than 500 bp. In a further preferred embodiment of the present invention, the UCOE is a 16 kb DNA fragment spanning the human hnRNP A2 gene with 5 kb 5' and 1.5 kb 3' flanking sequence, or a functional homologue or fragment thereof. Other UCOE of the present invention are described in U.S. Pat. No. 6,689,606.

The term "functional homologues or fragments" as used herein means homologues or fragments, which open chromatin or maintain chromatin in an open state and facilitate reproducible expression of an operably-linked gene. Preferably, the homologues are species homologues corresponding to the identified UCOEs or are homologues associated with other ubiquitously expressed genes.

In this aspect of the invention, the expression of the variant E1a protein leads to at least two-fold enhancement of expression of the activatable cistron in the host cell. Preferably the expression of the variant E1a leads to five-fold enhancement of expression of the activatable cistron. The variant E1a protein is efficiently expressed in the host cell and does not significantly inhibit the survival and proliferation of the host cell.

Host Cells of the Invention

An aspect of the invention provides a mammalian host cell comprising a first cistron encoding a transactivator, a second cistron encoding an apoptosis-protective protein that prevents cell-killing due to expression of the transactivator, and a third cistron encoding one or more desired proteins under the control of a promoter responsive to the transactivator. In a preferred embodiment, the transactivator is expressed from an efficient heterologous promoter at a level at which, in the absence of the protective protein, significant cell death would occur. Another aspect of the invention provides a mammalian host cell comprising a first cistron encoding a variant transactivator that retains transactivation activity but is defective in the ability to trigger apoptosis, and a second cistrons encoding one or more desired polypeptides under the control of a promoter responsive to the variant transactivator.

In a preferred embodiment, the mammalian host cell is selected from the group consisting of a CHO cell, a mouse myeloma cell, a mouse hybridoma cell, a rat myeloma cell, and a rat hybridoma cell. In other embodiments the host cell is a YB2/0 rat hybridoma cell. In yet other embodiments, the mammalian cell is a non-human mammalian cell. In still other embodiments, the host cell is not a HEK293 human embryonic kidney cell or a PER cell.

The cell line may be maintained adhering to plastic or another surface or may be maintained in suspension culture. Numerous tissue culture media are available for the growth of mammalian cell lines and the appropriate medium will be selected for the particular cell line and growth conditions. Additives and modifications to the basal medium may be made. For example one or more proteins such as insulin, transferrin or albumen, or animal serum may be added if desired. Lipid supplements may be required for certain cell lines such as the myeloma NS0. Antibiotics and selective agents such as zeocin, G418, hygromycin, methotrexate or methionine sulphoximine may also be added to maintain sterility or to maintain selective pressure according to the vectors introduced into the host cell. In a preferred embodiment of this aspect of the invention, the host cell is a CHO cell line maintained in serum-free suspension culture. In a particularly preferred embodiment, the CHO line is the CHO-S cell line (Invitrogen) cultured in a protein-free culture medium. An example of a suitable medium is CD-CHO medium (Invitrogen). Other suitable protein-free media are HyQ SFM4CHO and HyQ CDM4CHO (HyClone). The base medium may be supplemented with suitable medium supplements, for example comprising one or more amino acids, sugars, vitamins, hydrolysates (from either soy or yeast extract) or minerals. Media lacking glutamine may alternatively be used. For example, a derivative of CDCHO or CDM4CHO medium may be prepared without glutamine. If a glutamine-free medium is used, the basal medium may advantageously be supplemented with a suitable supplement comprising one or more of the following: glutamate, asparagine, and nucleosides. Recombinant cell lines expressing a gene of interest may be grown in any suitable fermentation process, including batch suspension and fed-batch fermentations. The cells may be grown at 37° C. and, advantageously, the temperature may be controlled in order to optimize cell viability and recombinant protein expression. For example, the temperature may be reduced to a temperature in the range 31-34° C. once the cells reach or are close to the peak viable cell density.

Any number of selection systems may be used to recover cell-lines containing the nucleic acids. These include, but are not limited to, the herpes simplex virus thymidine kinase (Wigler, M. et al. (1977) Cell 11:223-32) and adenine phosphoribosyltransferase (Lowy, l. et al. (1990) Cell 22:817-23) genes that can be employed in tk⁻ or aprt⁻ cells, respectively. Also, antimetabolite, antibiotic or herbicide resistance can be used as the basis for selection; for example, DHFR, which confers resistance to methotrexate (Wigler, M. et al. (1980) Proc. Natl. Acad. Sci. 77:3567-70); glutamine synthetase (GS), which confers glutamine-independent growth and resistance to methionine sulphoximine (Bebbington et al. (1992) Biotechnology 10 (2):169-75; and Cockett et al. (1991) Nucleic Acids Res. 25; 19 (2):319-25); npt, which confers resistance to the aminoglycosides, neomycin and G-418 (Colbere-Garapin, F. et al (1981) J Mol Biol. 150:1-14); and als or pat, which confer resistance to chlorsulfuron and phosphinotricin, respectively (Murry, supra). Additional selectable genes have been described, for example, trpB, which allows cells to utilize indole in place of tryptophan, or his, which allows cells to utilize histinol in place of histidine (Hartman, S. C. and R. C. Mulligan (1988) *Proc. Natl. Acad Sci* 85:8047-5). The use of visible markers has gained popularity with such markers as green fluorescent protein (GFP), anthocyanins, betaglucuronidase and its substrate GUS, and luciferase and its substrate luciferin, being widely used not only to identify transformants, but also to quantify the amount of transient or stable protein expression attributable to a specific vector system (Rhodes, et al. (1995) Methods Mol. Biol. 55:121-131).

Although the presence/absence of marker gene expression suggests that the cistron of interest is also present, the presence and expression of the desired polypeptide may need to be confirmed. For example, if the sequence encoding a desired polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques, which include, for example, membrane, solution, or chip based technologies for the detection and/or quantification of nucleic acid or protein.

A variety of protocols for detecting and measuring the expression of desired polypeptide products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990, Serological Methods, a Laboratory Manual, APS Press, St Paul. Minn.) and Maddox, et al. (1983; J Exp. Med 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligo labeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure).

Vectors of the Invention

The vector systems of the invention may comprise any vector capable of transferring DNA to a cell. Preferably, the vector is an integrating vector or an episomal vector. Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication of the target cells. In such cases, the replication defective viral genome can be packaged by a helper virus in accordance with conventional techniques. Generally, any retrovirus meeting the above criteria of infectiousness and capability of functional gene transfer can be employed in the practice of the invention.

Suitable retroviral vectors include but are not limited to pLJ, pZip, pWe and pEM, well known to those of skill in the art. Suitable packaging virus lines for replication-defective retroviruses include, for example, Ψrip, ΨCre, Ψ2 and ΨAm.

Other vectors useful in the present invention include adenovirus, adeno-associated virus, SV40 virus, vaccinia virus, HSV and pox virus vectors. A preferred vector is an adenovirus vector. Adenovirus vectors are well known to those skilled in the art and have been used to deliver genes to numerous cell types, including airway epithelium, skeletal muscle, liver, brain and skin (Hitt, et al. (1997) *Pharmacology* 40: 137-206; and Anderson (1998) *Nature* 392 (6679 Suppl): 25-30).

A further preferred vector is the adeno-associated (AAV) vector. AAV vectors are well known to those skilled in the art and have been used to stably transduce human T-lymphocytes, fibroblasts, nasal polyp, skeletal muscle, brain, erythroid and hematopoietic stem cells for gene therapy applications (Philip et al., 1994, *Mol. Cell. Biol.*, 14:2411-2418; Russell et al., 1994, *PNAS USA*, 91:8915-8919; Flotte et al., 1993, *PNAS USA*, 90:10613-10617; Walsh et al., 1994, *PNAS USA*, 89:7257-7261; Miller et al., 1994, *PNAS USA* 91:10183-10187; Emerson, 1996, *Blood*, 87:3082-3088). International Patent Application WO 91/18088 describes specific AAV based vectors.

Preferred episomal vectors include transient non-replicating episomal vectors and self replicating episomal vectors with functions derived from viral origins of replication such as those from EBV, human papovavirus (BK) and BPV Such integrating and episomal vectors are well known to those skilled in the art and are fully described in the body of literature well known to those skilled in the art. In particular, suitable episomal vectors are described in W098/07876.

Mammalian artificial chromosomes are also preferred vectors for use in the present invention. The use of mammalian artificial chromosomes is discussed by Calos (1996, *Trends Genet.* 12:463-466).

Various vectors and methods for introducing them into host cells are available for obtaining appropriate expression of the transactivator and the protective cistron of the invention. For example the cistrons can each be expressed from a strong constitutive promoter such as the hCMV-MIE promoter in plasmids pCI-neo or pCDNA3, or from a RSV-LTR promoter. The cistrons can be on the same or separate plasmids and appropriate selectable markers are used to select for clones in which the vectors have integrated into the genome. For example markers that confer resistance to hygromycin, neomycin (G418) or zeocin can be used. The cistron or cistrons used to express the recombinant protein may also be introduced on the same or a different plasmid and can be introduced using various selectable markers including resistance markers or amplifiable markers such as GS or DHFR. Various additional elements that are known in the art may be included with the transactivator cistron, the protective cistron or the activatable cistron to ensure appropriate levels of expression. For example splice sites, polyadenylation signals, 5' or 3' untranslated regions may be added. For the activatable cistron, efficient expression is desired and additional elements intended to enhance expression levels may be added, including UCOEs, insulators, barrier elements and signal peptides. The vectors for expression of the cistrons are introduced into the mammalian host cell by any of the available methods including calcium phosphate co-precipitation, electroporation or cationic lipid mediated transfection.

Suitable vector systems for expression of recombinant proteins and/or polypeptides according to the present invention may include one or more of the following attributes: (a) ease of manipulation; (b) elements that make high-level expression site-of-integration independent; (c) elements that make expression resistant to silencing/repression thereby allowing for sustained, stable expression over long periods of time; and (d) elements that express at high-levels in different cell types and in different species.

In order to express a desired protein and/or polypeptide, the nucleotide sequences encoding the polypeptide, or functional equivalents, may be inserted into appropriate expression vector, i.e., a vector that contains the necessary elements for the transcription and translation of the inserted coding sequence. Methods that are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

Depending on the vector system and host utilized, any number of suitable transcription and translation elements, including constitutive and inducible promoters, may be used. In mammalian cell systems, promoters from mammalian genes or from mammalian viruses are generally preferred. If it is necessary to generate a cell-line that contains multiple copies of the sequence encoding a polypeptide, vectors containing GS or DHFR selectable markers or vectors based on SV40 or EBV may be advantageously used with an appropriate selectable marker.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan and Shenk, (1984) Proc. Natl. Acad Sci USA 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic.

As will be understood by those of skill in the art, expression vectors containing polynucleotides of the invention may be designed to contain signal sequences that direct secretion of the encoded polypeptide through a eukaryotic cell membrane. Other recombinant constructions may be used to join sequences encoding a polypeptide of interest to nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen) between the purification domain and the encoded polypeptide may be used to facilitate purification.

One such expression vector provides for expression of a fusion protein containing a polypeptide of interest and a nucleic acid encoding six histidine residues preceding a thioredoxin or an enterokinase cleavage site. The histidine residues facilitate purification on IMIAC (immobilized metal ion affinity chromatography) as described in Porath, et al. (1992, Prot. Exp. Purif 3:263-281) while the enterokinase cleavage site provides a means for purifying the desired polypeptide from the fusion protein. A discussion of vectors that contain fusion proteins is provided in Kroll, et al. (1993; DNA Cell Biol 12:441-453).

Introducing Nucleic Acid into Host Cells

A vector of the invention may be delivered to a host cell non-specifically or specifically (i.e., to a designated subset of host cells) via a viral or non-viral means of delivery. Suitable protocols are readily known and/or available to those of skill in the art. Exemplary protocols that are suitable for achieving high-level, large-scale introduction of nucleic acids include electroporation, calcium phosphate-mediated transfection, cell fusion, and those recommended by Invitrogen/Gibco for transfection of the CHO-S host cell-line. Generally, positive selection of cells containing the nucleic acid may be achieved using agents such as, for example, hygromycin, G418, and puromycin. Following selection, the pool of resulting clones may, optionally, be further subcloned to identify individual clones with the desired levels of protein expression.

Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

Nucleic Acids of the Invention

The nucleic acid sequences of the invention are further directed to sequences that encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the variant transactivator proteins are changed via site-directed mutagenesis. This method uses oligonucleotide sequences that encode the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487-6500 (1982).

PCR may also be used to create variants of the transactivator proteins of the invention. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the collagen at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., Molecular Cloning: A Laboratory Manual, Cold Spring Harbor Laboratories, Cold Spring Harbor, N.Y., 1989, and Current Protocols in Molecular Biology, Ausubel et al.

Due to the inherent degeneracy of the genetic code, other DNA sequences that encode substantially the same or a functionally equivalent amino acid sequence may be used in the practice of the invention for the cloning and expression of these novel nucleic acids. Such DNA sequences include those that are capable of hybridizing to the appropriate novel nucleic acid sequence under stringent conditions.

Polynucleotides of the invention may comprise a native sequence (i.e. an endogenous sequence that encodes a protein and/or polypeptide or a portion thereof) or may comprise a sequence that encodes a variant or derivative. Typically, polynucleotide variants will contain one or more substitutions, additions, deletions and/or insertions, preferably such that the activity of the polypeptide encoded by the variant polynucleotide is not substantially diminished relative to a polypeptide encoded by the wildtype gene. For example, a variant E1a protein of the invention would maintain the ability to transactivate transcription. The term "variants" should also be understood to encompass homologous genes of xenogeneic origin.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Polynucleotides suitable for high-level, large-scale expression according to the present invention may be identified, prepared and/or manipulated using any of a variety of well established techniques—(see generally, Sambrook et al., Molecular Cloning: A Laboratory Manual, Cold Spring Harbor Laboratories, Cold Spring Harbor, N.Y., 1989, and other like references). For example, a polynucleotide may be identified by screening a microarray of cDNAs for tumor-associated expression. Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR), which is described in detail in U.S. Pat. Nos. 4,683,195, 4,683,202 and 4,800,159, each of which is incorporated herein by reference in its entirety. Briefly, in PCR, two primer sequences are prepared that are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR T' amplification procedure may be performed in order to quantify the amount of mRNA amplified. Polymerase chain reaction methodologies are well known in the art.

Any of a number of other template dependent processes, many of which are variations of the PCR amplification technique, are readily known and available in the art. Illustratively, some such methods include the ligase chain reaction, described, for example, in Eur. Pat. Appl. Publ. No. 320,308 and U.S. Pat. No. 4,883,750; Qβ Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., PCR Methods Applic. 1:1 1 1-19, 1991) and walking PCR (Parker et al., Nucl. Acids. Res. 19:3055-60, 1991). Other methods employing amplification may also be employed to obtain a full length cDNA sequence. Other amplification methods such as "one-sided PCR" (Ohara, 1989) are also well-known to those of skill in the art.

An amplified portion of a polynucleotide of the present invention may be used to isolate a full length gene from a suitable library (e.g., a tumor cDNA library or a library of mutagenized E1a DNAs) using well known techniques. Within such techniques, a library is screened using one or more polynucleotide probes or primers suitable for amplification.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular eukaryotic host can be selected to increase the rate of protein expression or to produce a recombinant RNA transcript having desirable properties, such as a half-life that is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations that modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

Recombinant Polypeptides

One aspect of the invention provides a method for producing a recombinant protein comprising culturing a cell line of the invention in a suitable medium such that the recombinant protein is secreted into the medium. A polypeptide may be an entire protein, or a portion thereof. Particular polypeptides of interest in the context of this invention are therapeutic polypeptides such as receptors, enzymes, ligands, regulatory factors, hormones, antibodies or antibody fragments and structural proteins, or variants thereof. Therapeutic polypeptides also include sequences encoding nuclear proteins, cytoplasmic proteins, mitochondrial proteins, secreted proteins, membrane-associated proteins, serum proteins, viral antigens, bacterial antigens, protozoal antigens and parasitic antigens. The product may be a single polypeptide such as a cytokine, a growth hormone or a single-chain antibody. Alternatively the product may be derived from more than one polypeptide such as an immunoglobulin, which contains a heavy-chain and a light-chain polypeptide. In this case each polypeptide is expressed from a separate copy of the activatable promoter or both polypeptides may be translated from a single mRNA with separate open reading frames separated by an internal ribosome entry site (IRES) element.

Within other illustrative embodiments, a polypeptide may be a fusion polypeptide that comprises multiple polypeptides. A fusion partner can, for example, assist in expressing the protein (an expression enhancer) at higher yields than the native recombinant protein. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences that may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Exemplary desired polypeptides according to the present invention include binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunologically bind," and/or is "immunologically reactive" to an antigen if it reacts at a detectable level (within, for example, an ELISA assay) with the polypeptide, and does not react detectably with unrelated polypeptides under similar conditions.

Natural antibodies have been known for many years. Natural antibodies of most vertebrates comprise a generally Y-shaped molecule having an antigen-binding site towards the free end of each upper arm. The remainder of the structure, and particularly the stem of the Y, mediates the effector functions associated with antibodies. Specifically, antibody molecules are comprised of two heavy (H) and two light (L) polypeptide chains, held together by disulfide bonds. Each chain of an antibody chain is divided into regions or domains, each being approximately 110 amino acids. The light chain has two such domains while the heavy chain has four domains. The amino acid sequence of the amino-terminal domain of each polypeptide chain is highly variable (V region), while the sequences of the remaining domains are conserved or constant (C regions). A light chain is therefore composed of one variable (VL) and one constant domain (CL) while a heavy chain contains one variable (VH) and three constant domains (CH1, CH2 and CH3). An arm of the Y-shaped molecule consists of a light chain (V+CL) and the variable domain (VH) and one constant domain (CH1) of a heavy chain. The tail of the Y is composed of the remaining heavy chain constant domains (CH2+CH3). The C-terminal ends of the heavy chains associate to form the Fc portion. Within each variable region are three hypervariable regions. These hypervariable regions are also described as the complementarity determining regions (CDRs) because of their importance in binding of antigen. The four more conserved regions of the variable domains are described as the framework regions (FRs). Each domain of an antibody consists of two beta-sheets held together by a disulfide bridge, with their hydrophobic faces packed together. The individual beta strands are linked together by loops. The overall appearance can be described as a beta barrel having loops at the ends. The CDRs form the loops at one end of the beta barrel of the variable region. Certain vertebrate immunoglobulins have a different structure. Thus camellids and some sharks have functional immunoglobulins comprised exclusively of heavy chains (e.g. Lauwereys et al (1998), EMBO J. 17, 5312, 1998; Stanfield et al (2004) Science 305: 1770). Recombinant derivatives of antibodies have also been described which have similarities to camellid antibodies and in which the antigen-binding domain does not involve a light chain, including "nanobodies," single-domain antibodies and "camelized" antibodies.

A number of therapeutically useful molecules are known in the art that comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule.

Fv fragments are, however, more commonly derived using recombinant techniques known in the art. Any fragment of an antibody that is produced by enzymatic cleavage can also be made using recombinant techniques to express the desired fragment without requiring enzymatic processing. The Fv fragment includes a non-covalent VH::VL heterodimer including an antigen-binding site, which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091 A single chain Fv ("sFv") polypeptide is a covalently linked VH::VL heterodimer that is expressed from a gene fusion including VH- and VL-encoding genes linked by a peptide-encoding linker. Huston et al. (1988) Proc. Nat. Acad. Sci. USA 85 (16):5879. A number of methods have been described to discern chemical structures for converting the naturally aggregated—but chemically separated—light and heavy polypeptide chains from an antibody V region into an sFv molecule that will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

By 1990, over 100 murine monoclonal antibodies were in clinical trials, particularly in the U.S. and especially for application in the treatment of cancer. However, by this time it was recognized that rejection of murine monoclonal antibodies by the undesirable immune response in humans termed the HAMA (Human Anti-Mouse Antibody) response was a severe limitation, especially for the treatment of chronic disease. Therefore, the use of rodent MAbs as therapeutic agents in humans is inherently limited by the fact that the human subject will mount an immunological response to the MAb and either remove the MAb entirely or at least reduce its effectiveness.

Proposals have therefore been made for making MAbs less antigenic in humans. Such techniques can be generically termed "humanization" techniques. These techniques generally involve the use of recombinant DNA technology to manipulate DNA sequences encoding the polypeptide chains of the antibody molecule. The use of recombinant DNA technology to clone antibody genes has provided an alternative whereby a murine monoclonal antibody can be converted to a predominantly human-form (i.e., humanized) with the same antigen binding properties. Generally, the goal of the humanizing technology is to develop humanized antibodies with very little or virtually no murine component apart from the CDRs so as to reduce or eliminate their immunogenicity in humans.

A number of "humanized" antibody molecules comprising an antigen binding site derived from a immunoglobulin have been described. One method utilizes chimeric antibodies. "Chimeric" antibodies comprise a light chain and a heavy chain: the light chain is comprised of a light chain variable region and a light chain constant region; the heavy chain is comprised of a heavy chain variable region and a heavy chain constant region. Chimeric antibodies comprise variable regions from one species and constant regions from another species (for example, mouse variable regions joined to human constant regions). (See, e.g., U.S. Pat. Nos. 4,816,397 and 4,816,567, Winter et al. (1991) Nature 349:293-299; Lobuglio et al. (1989) Proc. Nat. Acad. Sci. USA 86:4220-4224; Shaw et al. (1987) J Immunol. 138:45344538; and Brown et al. (1987) Cancer Res. 47:3577-3583). Other methods of humanizing antibodies include grafting rodent CDRs into a human supporting. FR prior to fusion with an appropriate human antibody constant domain (Riechmann et al. (1988)

Nature 332:323-327; Verhoeyen et al. (1988) Science 239: 1534-1536; and Jones et al. (1986) Nature 321:522-525), and providing rodent CDRs supported by recombinantly veneered rodent FRs (European Patent Publication No. 519.596, published Dec. 23, 1992). These "humanized" molecules are designed to minimize unwanted immunological response toward rodent antihuman antibody molecules, which limits the duration and effectiveness of therapeutic applications of those moieties in human recipients.

Recombinant technology now allows the preparation of antibodies having the desired specificity from recombinant genes encoding a range of antibodies (Van Dijk et al., 1989; incorporated herein by reference). Certain recombinant techniques involve the isolation of the antibody genes by immunological screening of combinatorial antibody phage expression libraries prepared from RNA isolated from the spleen of an immunized animal (Morrison et al., 1986; Winter and Milstein, 1991; each incorporated herein by reference).

For such methods, combinatorial antibody phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids," yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference).

This general technique for filamentous phage display is described in U.S. Pat. No. 5,658,727, incorporated herein by reference. In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for producing diverse libraries of antibodies and screening for desirable binding specificities is described in U.S. Pat. Nos. 5,667,988 and 5,759,817, each incorporated herein by reference. The method involves the preparation of libraries of heterodimeric antibody molecules in the form of phagemid libraries using degenerate oligonucleotides and primer extension reactions to incorporate the degeneracies into the CDR regions of the antibody variable heavy and light chain variable domains, and display of the mutagenized polypeptides on the surface of the phagemid. Thereafter, the display protein is screened for the ability to bind to a preselected antigen.

The method for producing a heterodimeric antibody molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions that encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDRI or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an antibody while requiring only one of the two antibody chains.

Specifically, the method is practiced in the absence of the antibody light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

Alternatively, the polypeptide expressed using the present invention can be a fully-human antibody. To prepare an antibody with a desired specificity from a human patient, one would simply obtain human lymphocytes from an individual having the desired specific antibodies, for example from human peripheral blood, spleen, lymph nodes, tonsils or the like, utilizing techniques that are well known to those of skill in the art. The use of peripheral blood lymphocytes will often be preferred.

Human monoclonal antibodies may be obtained from the human lymphocytes producing the desired antibodies by immortalizing the human lymphocytes, generally in the same manner as described above for generating any monoclonal antibody. The reactivities of the antibodies in the culture supernatants are generally first checked, employing one or more selected antigen(s), and the lymphocytes that exhibit high reactivity are grown. The resulting lymphocytes are then fused with a parent line of human or mouse origin, and further selection gives the optimal clones.

The recovery of monoclonal antibodies from the immortalized cells may be achieved by any method generally employed in the production of monoclonal antibodies. For instance, the desired monoclonal antibody may be obtained by cloning the immortalized lymphocyte by the limiting dilution method or the like, selecting the cell producing the desired antibody, growing the selected cells in a medium or the abdominal cavity of an animal, and recovering the desired monoclonal antibody from the culture supernatant or ascites.

Such techniques have been used, for example, to isolate human monoclonal antibodies to *Pseudomonas aeruginosa* epitopes (U.S. Pat. Nos. 5,196,337 and 5,252,480, each incorporated herein by reference); polyribosylribitol phosphate capsular polysaccharides (U.S. Pat. No. 4,954,449, incorporated herein by reference); the Rh(D) antigen (U.S. Pat. No. 5,665,356, incorporated herein by reference); and viruses, such as human immunodeficiency virus, respiratory syncytial virus, herpes simplex virus, varicella zoster virus and cytomegalovirus (U.S. Pat. Nos. 5,652,138; 5,762,905; and 4,950,595, each incorporated herein by reference). After isolation, the genes encoding the desired antibody can be identified and cloned using standard techniques. The desired genes can then be utilized in the present system to express high levels of recombinant human antibody.

Recombinant technology can also be used to prepare antibodies from transgenic mice containing human antibody libraries. Such techniques are described in U.S. Pat. No. 5,545,807, incorporated herein by reference. In a most general sense, these methods involve the production of a transgenic animal that has inserted into its germline genetic material that encodes for at least part of an antibody of human origin or that can rearrange to encode a repertoire of antibodies. The inserted genetic material may be produced from a human source, or may be produced synthetically. The material may code for at least part of a known antibody or may be modified to code for at least part of an altered antibody.

The inserted genetic material is expressed in the transgenic animal, resulting in production of an antibody derived at least in part from the inserted human antibody genetic material. It is found the genetic material is rearranged in the transgenic animal, so that a repertoire of antibodies with part or parts derived from inserted genetic material may be produced, even if the inserted genetic material is incorporated in the germine in the wrong position or with the wrong geometry.

Once a suitable transgenic animal has been prepared, the animal is simply immunized with the desired immunogen. Depending on the nature of the inserted material, the animal may produce a chimeric antibody, e.g. of mixed mouse/human origin, where the genetic material of foreign origin encodes only part of the antibody; or the animal may produce an entirely foreign antibody, e.g. of wholly human origin, where the genetic material of foreign origin encodes an entire antibody.

The foregoing transgenic animals are usually employed to produce human antibodies of a single isotype, more specifically an isotype that is essential for B cell maturation, such as IgM and possibly IgD. Another preferred method for producing human antibodies is described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes. The genes encoding the desired antibodies generated by the transgenic animal can be cloned utilizing standard techniques and produced using the expression system of the present invention.

Additional modifications can be made to the sequences of antibodies to alter the effector function or to reduce the potential for immunogenicity or for another purpose. For example, point mutations may be introduced into the constant region of the antibody Heavy chain to modify effector function as described in U.S. Pat. Nos. 5,624,821 and 5,648,260. Alterations may be made in the V-region of antibodies with the purpose of altering the binding specificity or affinity or to remove T-cell epitopes and hence reducing immunogenicity, a process known as “de-immunization”. For this purpose, computer algorithms are used to predict peptide sequences within the antibody coding sequence which may be involved in binding to human MHC Class II molecules. These potential T-cell epitopes may be removed by appropriate alteration in the sequence. Such altered or designed antibody sequences may be constructed synthetically by construction and assembly of chemically synthesized oligonucleotides or may be introduced into cloned DNA sequences by site-directed mutagenesis according to standard techniques known in the art.

EXAMPLES

The following examples are provided as a guide for a practitioner of ordinary skill in the art. The examples should not be construed as limiting the invention, as the examples merely provide specific methodology useful in understanding and practicing an embodiment of the invention.

Example 1

Cloning and Expression of E1a and a Variant E1a Defective in RB Binding

The E1a gene from Ad5 is cloned by PCR from adenoviral DNA in the adherent HEK293 cell line (Stratagene) using the following oligonucleotide primers and cloned between the EcoR1 and Sal1 sites of pCI-neo (Promega) to construct pCI-E1a.neo.

```
                                          (SEQ ID NO: 6)
Primer 1: CCCGAATTCGCCGCCACCATGAGACATATTATCTGCCAC (SEQ ID NO: 7)
Primer 2: CCCGTCGACCTTATGGCCTGGGGCGTTT.
```

Alternatively, the gene is expressed from the RSV-LTR promoter in the plasmid pOPRSVI/MCS (Stratagene) between the Kpn1 and Not1 sites using the following amplification primers to construct an expression plasmid pRSV-E1a.

```
                                          (SEQ ID NO: 8)
Primer 3: CCCGGTACCGCCGCCACCATGAGACATATTATCTGCCAC (SEQ ID NO: 9)
Primer 4: CCCGCGGCCGCCTTATGGCCTGGGGCGTTT.
```

The tyrosine a amino acid 47 is mutated to histidine (47H) and the cysteine a amino acid 124 is mutated to glycine (124G) by PCR mutagenesis. To introduce the 124G mutation, the forward primer is:

```
                                         (SEQ ID NO: 10)
Primer 5: GGAGGTGATC GATCTTACCG GCCAC.
```

The reverse primer is either Primer 2 or Primer 4 above for cloning into vectors containing Sal1 or Not1 sites respectively. Primer 5 contains a Cla1 site that can be used for reconstruction of the 5' end of the gene (360 bp Kpn1-Cla1 fragment from pRSV-E1a). For this purpose, the E1a gene is cloned in a plasmid introduced into an *E. coli* strain that is defective in dam methylase.

For construction of the 47H mutation in pRSV-E1a, mutagenesis is carried out using Primers 3 and 4 together with mutagenesis primers 6 and 7:

```
                                         (SEQ ID NO: 11)
Primer 6:
CCTACCCTTCACGAACTGCATGATTTAGACGTGACG (SEQ ID NO: 12)
Primer 7:
CGTCACGTCTAAATCATGCAGTTCGTGAAGGGTAGG.
```

PCR reactions are set up using titered amounts of template DNA. (e.g. 1 ng, 4 ng, 8 ng and 16 ng) and 100 ng each of forward and reverse primers. Reactions are run using Pfu polymerase (Stratagene) according to the manufacturer's instructions. PCR fragments are digested with appropriate restriction enzymes and subcloned into plasmid vectors. All DNA clones are verified by DNA sequencing; the nucleotide coding sequence for mutant E1a (47/124) is given in FIG. 5.

The vectors for expressing E1a or a variant E1a are introduced into CHO-S cells by lipofectamine-mediated transfection (Invitrogen) according to the manufacturer's instructions. Stable transfectants are selected using G418 (0.5 mg/ml). Because wild-type E1a induces apoptosis in the host cell when expressed from the efficient hCMV or RSV-LTR promoters, the transfection efficiency for E1a-expressing plasmids is greatly reduced compared to a pCI-neo control plasmid. The variant E1a defective in RB binding can be successfully transfected into the CHO-S cells at high frequency when expressed from strong promoters.

For detection of E1a expression, cells are fixed in phosphate-buffered saline containing 4% paraformaldehyde and stained with anti-E1a antibody (M73; Santa Cruz Biotechnology) followed by FITC-conjugated secondary antibody.

For analysis of transactivation, CHO-S cells are transfected with a reporter gene under the control of the hCMV-MIE promoter enhancer. The plasmid phrGFP-1 (Stratagene) expresses a modified green fluorescent protein (GFP) with reduced toxicity in mammalian cells under the control of the hCMV-MIE promoter. This plasmid is transiently transfected into CHO-S cells stably expressing E1a genes and relative GFP levels are determined by flow cytometry 24-48 hours post-transfection. For selection of stable GFP-expressing cell lines, a hygromycin selectable marker is introduced at the LoxP site in phrGFP-1 using the EC-Hyg expression cassette (Stratagene) according to the manufacturer's instructions and CHO-S transfectants selected using hygromycin.

Cell lines expressing E1a transactivate the hCMV promoter and lead to increased levels of expression of GFP both in transient and stable transfections compared with GFP levels in CHO-S cells lacking E1a activity.

Example 2

Cloning and Expression of E1b-19K Protein

E1b-19K coding sequence is cloned from Ad5 DNA by PCR amplification as described in Example 1 but using the following primers:

```
                                         (SEQ ID NO: 13)
Primer 8:
CCCGAATTCGCCGCCACCATGGAGGCTT GGGAGTGTTT (SEQ ID NO: 14)
Primer 9:
CCCGTCGACCAACATTCAT TCCCGACGGT.
```

The PCR fragment is cloned between the EcoR1 and Sal1 sites of pExchange-1 (Stratagene) such that the gene is expressed from the hCMV promoter. The nucleotide sequence of the EcoR1-Sal1 DNA fragment is shown in FIG. 6. A selectable marker is inserted in the vector using LoxP mediated exchange (Stratagene) and the expression plasmid is used to transfect CHO-S cells as described in Example 1.

For analysis of protein expression by immunofluorescence, cells are seeded on coverslips, fixed in phosphate-buffered saline containing 4% paraformaldehyde, and the preparations stored in phosphate-buffered saline at 4° C. Cells are stained with rat monoclonal antibody to E1b-19-kDa (DP07L; EMD Biosciences) according to the manufacturer's instructions. The samples are then stained with fluorescein isothiocyanate (FITC)-conjugated secondary anti-rat antibodies and visualized with a fluorescence microscope.

Cells expressing E1b-19K are transfected with wild-type or variant E1a as described in Example 1. The E1b-19K expressing cells are resistant to apoptosis induction induced by E1a. Transactivation by E1a is determined as described in Example 1.

Example 3

Cloning and Expression of Variant Hamster Bcl-2

The hamster Bcl-2 cDNA is cloned by PCR amplification using standard techniques using amplification primers based on the known sequence of hamster Bcl-2 (Genbank AJ271720). PCR mutagenesis is used to construct the deletion variant Bcl-2 coding sequence shown in FIG. 3.

Standard recombinant polymerase chain reaction methodology is employed to insert oligonucleotides encoding the HA epitope, (M)AYPDYVPDYAV (SEQ ID NO: 56), at the 5'-end of the protein-coding sequence of BCL-2 cDNA. The coding sequences are cloned into the vector pCI-neo (Promega) carrying a neomycin resistance gene or into a derivative vector carrying a hygromycin resistance gene. The authenticity of all constructs is verified by DNA sequencing.

The vectors are transfected into CHO-S cells, using Lipofectamine (Invitrogen) according to the manufacturer's instructions and stable transfectants obtained by selection in G418 or hygromycin B and identified by Western blot analysis and immunofluorescence. Western blots are carried out using antisera to HA Tag.

Cells expressing recombinant Bcl-2 are transfected with Wild-type or variant E1a as described in Example 1. The Bcl-2 expressing cells are resistant to apoptosis induction induced by E1a. Transactivation by E1a is determined as described in Example 1.

Example 4

Cloning and Expression of Human RB

The cDNA encoding human RB protein (Genbank sequence M15400; Lee W H, Bookstein R, Hong F, Young L J, Shew J Y, Lee E Y (1987) Science. 235:1394-9) is cloned between the Sal1 and Not1 sites in the expression vector pCI-neo. PCR primers used are:

```
                                       (SEQ ID NO: 16)
Primer 10:
CCCGTCGACGCCGCCACCATGCCGCCCA AAACCCCCG (SEQ ID NO: 17)
Primer 11:
CCCGCGGCCGCCGGTCCTGAGA TCCTCATTTC.
```

The sequence of the constructed human RB coding sequence (Sal1-Not1 fragment; SEQ ID NO: 18) is shown in FIG. 7. CHO-S cells are transfected as described in Example 1 and RB-transfected cells are detected by Western blotting using antibody XZ55 (Pharmingen).

Example 5

Interaction of E1a and RB in the Periplasm of *E. coli*

The bait fragment, is subcloned by ligating an EcoRI-MunI fragment (amino acids 379 to 835) of Rb into the EcoRI site of pAS2 (Clontech). This fragment of Rb spans the A-B and C pockets of Rb that are necessary and sufficient for binding to E1a. The RB fragment is then cloned in-frame with a beta lactamase protein. E1a proteins are expressed in *E. coli* in functional form as described by Ferguson et al (1985) Mol Cell Biol. 5:2653-61). E1a-BLIP fusion proteins are constructed by insertion of E1a fragments N-terminal to BLIP. For this purpose, a fragment of the E1a coding sequence with the intron and CR3 deleted, is used. Thus the single Sma1 site can be used to define the C-terminus of the E1a fragment. Fragments of E1a are inserted in frame N-terminal to a BLIP fragment in an *E. coli* expression vector.

On co-expression in *E. coli*, the fusion proteins are generated in the periplasm and association of E1a and RB will lead to inhibition of beta-lactamase activity. The bacteria are therefore sensitive to ampicillin. Mutants of E1a defective in RB association will confer resistance to ampicillin by release of BLIP from beta-lactamase. Variant clones are characterized by DNA sequencing.

Example 6

Cloning and Expression of a Mutant CREB

Human cAMP response-element binding protein (CREB) exists in two forms, a longer form denoted CREB-B and a shorter alternative splice variant, CREB-A (Berkowitz and Gilman (1990) Proc. Natl. Acad. Sci. 87: 5258-5262). The cDNA encoding human CREB-A is cloned using PCR for insertion between EcoR1 and Sal1 sites with the following primers:

```
                                       (SEQ ID NO: 22)
Primer 12:
CCCGAATTCGCCGCCACCATGACCATGGACTCTGGAGCAGACA (SEQ ID NO: 23)
Primer 13:
GTCGACCCAAATTAATCTGATTTGTGGCAG.
```

A variant CREB with constitutive transactivation activity (Du et al (2000) Mol. Cell. Biol. 20: 4320-4327) is generated by changing the Tyrosine residue at position 134 to Phenylalanine (Y134F) by site-directed mutagenesis according to standard procedures. A single point mutation at nucleotide 374 in the sequence shown in FIG. 8 (changing A to T) generates the Y134F mutation.

The variant CREB coding sequence (FIG. 8) can be cloned between EcoR1 and Sal sites in the pCIneo expression vector and introduced into mammalian cells as described in Example 1. In order to protect host cells from apoptosis induced by overexpression of CREB or variant CREB, a gene encoding a protective protein may also be introduced into the host cell as described in Examples 2 and 3.

Example 7

Cloning and Expression of E1a and a Variant E1a Defective in RB Binding

Mammalian expression vector KB5008 was derived from pREP4 (Invitrogen) by deleting its OriP and EBNA-1 components and replacing its Hygromycin resistance gene with a Puromycin resistance gene. A plasmid map of KB5008 is shown on FIG. 9. It carries a multiple cloning site between a RSV LTR promoter and SV40 polyA signal. It also carries an Ampicillian resistance gene for *E. coli* selection and a Puromycin resistance gene for mammalian cell selection.

The E1a gene from Ad5 was amplified by PCR from genomic DNA of HEK293 cells (Stratagene) using the following oligonucleotide primers, and was cloned between the HindIII and XhoI sites of KB5008 to give vector KB5013. The E1a gene included 2 exons and 1 intron and was expressed from the RSV-LTR promoter.

```
                                       (SEQ ID NO: 24)
Primer 14:
GTCAAGCAAGCTTGCCGCCACCATGAGACATATTATCTGCCACGG (SEQ ID NO: 25)
Primer 15:
CGCAGTCTCGAGTTATGGCCTGGGGCGTTTACAGCTC.
```

The Tyrosine amino acid 47 was mutated to Histidine (47H) by bridge-PCR mutagenesis to generate plasmid KB5014. The 47H mutation was introduced using Primer 14 and 15 together with mutagenesis Primers 16 and 17.

```
                                          (SEQ ID NO: 26)
Primer 16:
CACCTACCCTTCACGAACTGCATGATTTAGACGTGACGGCC.

(SEQ ID NO: 27)
Primer 17:
GGCCGTCACGTCTAAATCATGCAGTTCGTGAAGGGTAGGTG.
```

The Cysteine amino acid 124 was mutated to Glycine (124G) by bridge-PCR mutagenesis to generate plasmid KB5015. The 124G mutation was introduced using Primer 14 and 15 together with mutagenesis primers 18 and 19.

```
                                          (SEQ ID NO: 28)
Primer 18:
CGGAGGTGATCGATCTTACCGGCCACGAGGCTGGCTTTCCAC (SEQ ID NO: 29)
Primer 19:
GTGGAAAGCCAGCCTCGTGGCCGGTAAGATCGATCACCTCCG.
```

Double mutation of 47H and 124G was constructed similarly by bridge-PCR mutagenesis using Primers 14, 15, 16, 17, 18 and 19 to generate plasmid KB5016.

PCR reactions were set up using Qiagen's Taq PCR Master Mix Kit. PCR fragments were digested with appropriate restriction enzymes and subcloned into plasmid vectors. All DNA clones were verified by DNA sequencing. The nucleotide coding sequence for E1a is shown in FIG. 10 and the coding sequence for E1a Y47H in FIG. 11.

The plasmids for expressing E1a or its variants were introduced into CHO-S or CHO-K1 cells by lipofectamine-mediated transfection (Invitrogen) according to the manufacturer's instructions. E1a expression was detected by Western Blot with anti-E1a antibody (M58; BD PharMingen) using transfected CHO cells (FIG. 16*a*).

To assay promoter activities, a reporter gene vector KB5019 was constructed by digesting pSEAP-Control (Clontech) with EcoRI and HpaI, and ligating the 1694 bp DNA fragment into EcoRI and SmaI sites of pCI-neo (Promega). This plasmid expresses SEAP under the control of hCMV-MIE promoter and was transiently transfected into CHO-K1 cells. Relative SEAP levels from culture media were determined by calorimetric assay using 1-Step PNPP as substrate (Pierce) after 48 hours. $1 \times 10^5$ cells/well in 0.5 ml of F-12K medium (ATCC) were seeded in 24-well plates the day before transfection. Each well was transfected with 0.4 μg of total DNA and 1 μl of lipofectamine. A titration of 0 to 0.1 μg of SEAP reporter plasmid KB5019 were used to transfect cells in duplicate wells, and control plasmid KB35008 or E1a expressing plasmid KB5013 were used to make the total DNA to 0.4 μg/well. 48 hours after transfection, 5 μl of culture media was mixed with 100 μl of PNPP substrate solution (Pierce) for 10 min to assay SEAP activity by taking absorption at 405 nm. The control was mock transfected CHO-K1 cells. When cells were transfected with 0 to 0.1 μg of KB5019, SEAP activities increased approximately in proportion to the amount of DNA used for transfection, indicating that the assay was in the linear range and sensitive to the amount of SEAP protein.

To investigate the effect of E1a expression on CMV promoter activity, CHO-K1 cells were co-transfected with KB5019 and E1a expressing plasmids. After 48 hours, SEAP activities were assayed from the culture media. Wild-type E1a and its variants were found to increase SEAP activities by 3-5 fold indicating that E1a trans-activated the CMV promoter (FIG. 17).

E1a expression plasmids carry a Puromycin resistance gene and can be used to select stable transfected cells under Puromycin (10 μg/ml). CHO-K1 cells were transfected with E1a expression plasmids or control plasmid KB5008 under similar conditions, and then were cultured under Puromycin selection for 10 days before colonies were counted. All plasmids were linearized either by XmnI (within the Amp gene) or EcoNI (downstream of the E1a gene) before transfection (FIG. 9). $2 \times 10^6$ CHO-K1 cells were transfected with 5 μg of linearized plasmids and 12.5 μl lipofectamine in 10-cm tissue culture plates. 48 hours after transfection, Puromycin (10 μg/ml) was added and plates were cultured for 10 days. Numbers of stable colonies were then counted under microscope. Transfection of E1a and its variants exhibited less than 10% of colonies compared to the control plasmid, KB5008, indicating that E1a induced apoptosis and greatly reduced colony formation efficiency. (The site of linearization does not affect the frequency of transfectant colonies recovered in this instance).

Example 8

Cloning and Expression of Hamster CREB and its Constitutive Active Mutant cAMP response-element binding protein (CREB) exists in two forms, a longer form denoted CREB-B and a shorter alternative splice variant, CREB-A (Berkowitz and Gilman (1990) Proc. Natl. Acad. Sci. 87: 5258-5262). The cDNA encoding hamster CREB-B was cloned using RT-PCR from CHO-S cells with the following primers:

```
                                          (SEQ ID NO: 30)
Primer 20:
GTCAAGCAAGCTTGCCGCCACCATGACCATGGAATCTGGAGC (SEQ ID NO: 31)
Primer 21:
CGCAGTGGATCCTTAATCTGATTTGTGGCAGTAAAGG.
```

It was then cloned between the HindIII and BamHI sites of KB5008 to give vector KB5017 in which the CREB gene was expressed from the RSV-LTR promoter.

A variant CREB with constitutive transactivation activity (described in human cells, Du et al (2000) Mol. Cell. Biol. 20: 4320-4327) was generated by changing the Tyrosine residue at position 134 to Phenylalanine (Y134F) by bridge-PCR mutagenesis using Primer 7 and 8 together with mutagenesis primers 22 and 23.

```
                                          (SEQ ID NO: 32)
Primer 22:
GTCATTCAAAATTTTCCTGAAGGAAGGCCTCCTTGAAAG (SEQ ID NO: 33)
Primer 23:
TCTTTCAAGGAGGCCTTCCTTCAGGAAAATTTTGAATGAC.
```

The nucleotide coding sequence for hamster CREB-B is shown in FIG. 12 and the coding sequence for hamster CREB-B variant Y134F is shown in FIG. 13:

The plasmids KB5017 and KB5018 for expressing CREB or CREB/Y134F were introduced into CHO-S or CHO-K1 cells as described in Example 7. CREB expression was detected by Western Blot with anti-CREB antibody (Upstate, FIG. 16b).

Trans-activating effects of CREB on CMV promoter were assayed similarly using SEAP reporter gene as in Example 7. CHO-K1 cells were co-transfected with KB5019 and CREB expressing plasmids, and then SEAP activities were assayed from culture media after 48 hours. Hamster CREB-B and CREB-B/Y134F were found to increase SEAP activities by 3-5 fold (FIG. 17).

Colony formation assay of CREB and CREB/Y134F were performed as in Example 7. Stable CREB expressing cells were generated by transfecting CHO-K1 cells and selected under Puromycin (10 µg/ml). All plasmids were linearized by XmnI digestion before transfection. Similar to E1a, over-expression of CREB induced apoptosis in the host cell, and the colony formation efficiency of CREB-expressing plasmids were greatly reduced compared to the control plasmid.

Example 9

Cloning of E1b-19K Protein

E1b-19K coding sequence was cloned from HEK293 cells by PCR amplification as described in Example 7 but using the following primers:

```
                                           (SEQ ID NO: 34)
Primer 24:
GGCATTCCAAGCTTACTGTTGGTAAAGCCGCCACCATGGAGGCTTGGG

AGTGTTTGG (SEQ ID NO: 35)
Primer 25:
GATCGACTCTAGATCATTCCCGAGGGTCCAGGCCGG.
```

The PCR fragment was then cloned between the HindIII and XbaI sites of pGL3-control (Promega, map is shown in FIG. 9) to give vector KB5026 in which E1b-19K was expressed from the SV40 promoter. The nucleotide coding sequence is shown in FIG. 14.

Example 10

Cloning and Expression of Hamster Bcl-2 and its Deletion Mutant

The hamster Bcl-2 cDNA was cloned by RT-PCR with the following primers:

```
                                           (SEQ ID NO: 36)
Primer 26:
TAAAGCCACCATGGCTCAAGCTGGGAGAACAGGGTATG (SEQ ID NO: 37)
Primer 27:
GATCGACTCTAGATCACTTGTGGCCCAGGTAGGTACCC.
```

It was then cloned between the NcoI and XbaI sites of pGL3-control to give vector KB5027 in which the Bcl2 gene was expressed from the SV40 promoter.

A deletion mutant of hamster Bcl-2 was constructed by bridge-PCR using Primer 26 and 27 together with following primers:

```
                                           (SEQ ID NO: 38)
Primer 28:
GTGGGAGATGTGGACGCCGCGGCCGCGGCCGCGAGCCCCGTGCCAC

CTGTGGTCC (SEQ ID NO: 39)
Primer 29:
GGACCACAGGTGGCACGGGGCTCGCGGCCGCGGCCGCGGCGTCCAC

ATCTCCCAC.
```

The nucleotide coding sequence of hamster Bcl2 deletion mutant Bcl2D is given in FIG. 15.

Plasmids for expression of Bcl2 or Bcl2D (KB5027 and KB5028) were transfected into CHO-K1 cells and their expression was confirmed by Western Blot using anti-Bcl2 antibody (ab7973, Abcam, FIG. 16c).

Example 11

Protection of E1b-19K from Apoptosis Induced by Over-Expression of E1a

In order to co-express anti-apoptosis protein E1b-19K together with E1a, double expression vectors for E1a and E1b-19K were constructed. The E1b-19K expression cassette was obtained as a SmaI-BamHI fragment from KB5026, and cloned into KB5013 between the Eco47III and BglII sites to give vector KB5029 that expresses E1a from RSV promoter and E1b-19K from SV40 promoter (FIG. 9). A similar double expression vector was constructed for expression of E1a-Y47H and E1b-19K (KB5054).

The anti-apoptosis activity of E1b-19K was investigated by colony formation assay under Puromycin (10 µg/ml) in transfected CHO-K1 cells as described in Example 7. When the double expression plasmid KB5029 was linearized by XmnI digestion downstream of the E1b-19K gene, co-expression of E1b-19K had little effect on colony formation of E1a expressing cells. However, when the plasmids KB5029 or KB5054 were linearized by EcoNI digestion between the two expression cassettes, E1b-19K rescued E1a cells fully from apoptosis and led to the generation of equivalent numbers of stable colonies as the control plasmid KB5008 (Table 3). It is known that the $2^{nd}$ promoter in tandem expression cassettes can have sub-optimum activity because of reading through of the $1^{st}$ promoter in mammalian cells. It is therefore likely that the SV40 promoter had a higher activity when the plasmid was linearized between the two cassettes leading to more efficient expression of E1b-19K than if the SV40 E1b-19K transcription unit was directly downstream of the E1a gene. Consistent with this hypothesis, linearization by EcoNI showed better anti-apoptotic activity than linearization by XmnI. These experiments suggested that E1b-19K could be used as anti-apoptosis protein to enable cells to maintain high level of E1a expression in established cell lines.

TABLE 2

Colony formation assay to determine rescue from E1a-induced apoptosis.

| Plasmid | First cistron (RSV-E1a) | Second cistron (SV40-apoptosis protective gene) | Stable Colonies (% of KB5008 transfectants) | |
|---------|-------------------------|------------------------------------------------|-------------------|-------------------|
|         |                         |                                                | Linearized with XmnI | Linearized with EcoNI |
| KB5008  | —                       | —                                              | 100%              | 100%              |
| KB5013  | E1a                     | —                                              | 8%                | 8%                |

TABLE 2-continued

Colony formation assay to determine rescue from E1a-induced apoptosis.

| Plasmid | First cistron (RSV-E1a) | Second cistron (SV40-apoptosis protective gene) | Stable Colonies (% of KB5008 transfectants) | |
|---|---|---|---|---|
| | | | Linearized with XmnI | Linearized with EcoNI |
| KB5014 | E1a/47H | — | 10% | 10% |
| KB5015 | E1a/124G | — | 0 | 0 |
| KB5016 | E1a/47H124G | — | 6% | 6% |
| KB5029 | E1a | E1b | 8% | 125% |
| KB5031 | E1a | Bcl2 | 20% | N/A |
| KB5033 | E1a | Bcl2D | 0% | N/A |
| KB5054 | E1a/47H | E1b | N/A | 70% |
| KB5055 | E1a/47H | Bcl2D | N/A | 110% |

Results are normalized to the number of colonies obtained with control plasmid KB5008 (100%). Actual colony numbers varied between experiments but were in the range 800-1600 colonies per transfected plate. Xmn1 linearizes plasmid downstream of the second cistron; EcoNI linearizes the plasmid between the two cistrons.

Example 12

Protection by E1b-19K from Apoptosis Induced by Over-Expression of CREB

The double expression vectors of CREB and E1b-19K were constructed as in is Example 11. The E1b-19K expression cassette was cut out with SmaI and BamHI from KB5026, and was cloned into KB5017 between Eco47III and BglII to give vector KB5030.

Colony formation assays were carried out and E1b-19K was found to fully eliminate the CREB-induced apoptosis (Table 3), regardless of the linearization site. Unlike the case of E1a, rescue from CREB-induced apoptosis can be readily achieved by co-expression of E1b-19K without the requirement of linearizing plasmids between the two expression cassettes.

TABLE 3

Colony formation assay to determine rescue from CREB-induced apoptosis.

| Plasmid | First cistron (RSV-CREB) | Second cistron (SV40-apoptosis protective gene) | Stable Colonies (% of KB5008 transfectants) |
|---|---|---|---|
| KB5008 | — | — | 100% |
| KB5017 | CREB | — | 17% |
| KB5018 | CREB/Y134F | — | 11% |
| KB5030 | CREB | E1b-19K | 123% |
| KB5032 | CREB | Bcl2 | 100% |
| KB5034 | CREB | Bcl2D | 100% |
| KB5035 | CREB/Y134F | E1b-19K | 122% |
| KB5036 | CREB/Y134F | Bcl2 | 71% |
| KB5037 | CREB/Y134F | Bcl2D | 100% |

Results are normalized to the number of colonies obtained with control plasmid KB5008 (100%). Actual colony numbers varied between experiments but were in the range 800-1600 colonies per transfected plate. Xmn1 was used to linearize plasmid downstream of the second cistron.

Example 13

Protection by Bcl2 from Apoptosis Induced by Over-Expression of E1a

The Bcl2 expression cassette was cut out with SacI and PshAI from KB5027, and was cloned into KB5013 between Eco47III and SacI to give KB5031. Thus KB5031 expresses E1a from RSV promoter and Bcl2 from SV40 promoter. Similar double expression vectors were made for E1a variants.

Colony formation assay as in Example 11 was carried out and Bcl2 was found to fully eliminate the E1a-induced apoptosis when the plasmids were linearized by EcoNI digestion (Table 2).

Example 14

Protection by Bcl2 from Apoptosis Induced by Over-Expression of CREB

The double expression vector of CREB and Bcl2 was constructed similarly as in Example 13. The Bcl2 expression cassette was cut out with SacI and PshAI from KB5027, and was cloned into KB5017 between Eco47III and SacI to give KB5032. The map is shown in FIG. 9.

Similar colony formation assay as in Example 11 was carried out and Bcl2 was found to fully eliminate the CREB-induced apoptosis (FIG. 18). Consistent with the results of E1b-19K, Bcl2 rescued CREB expressing cells without the requirement of linearizing plasmid between the RSV and SV40 cassettes (Table 3).

Example 15

Selection of Stable CHO-S Cells Expressing CREB

10 μg of plasmid KB5035 expressing both CREB/Y134F and E1b-19K was linearized by XmnI digestion and was used to transfected $1 \times 10^7$ CHO-S cells. After limited limiting—dilution cloning into 3 in 96-well plates and incubation in CHO-S-SFM II media (Invitrogen) with 10 μg/ml of Puromycin for 10 days, 2 stable clones KB5035-1 and 2 were selected. Expression of CREB was confirmed by Western blot (FIG. 18). Clone KB5035-1 showed high level of CREB expression and was chosen for continued study.

Plasmid KB5037, expressing CREB/Y134F and Bcl2D, was transfected similarly as above, and 5 stable CHO-S clones KB5037-1 to 5 were obtained under Puromycin selection. Expression of CREB and Bcl2D were confirmed by Western blot (FIG. 18). $4 \times 10^5$ indicated cells were incubated with 50 μl of lysis buffer for 5 minutes at room temperature. After spinning at 10,000 rpm for 5 minutes, 10 μl of supernatant was Western blotted with antibody against CREB (a) and Bcl2 (b). Wild-type CHO-S cells were used as negative control.

Clone KB5037-4 and 5 showed high level of CREB expression. Clone KB5037-5 was chosen for continued study because of its wild-type CHO-S like morphology.

Clones KB5035-1 and KB5037-5 were cultured without Puromycin selection for more than 30 cell generations, and CREB expression was confirmed by Western blot indicating that these cells with high level of CREB expression were stable.

Example 16

Antibody Production from CHO-S Cells Expressing CREB

The DNA sequences encoding the heavy chain and light chain of chimeric IgG1kappa recombinant Antibody-1 were cloned into mammalian expression vectors under the control of CMV promoter to make vectors c15-2 and c13-2 for expression of the heavy and light chains respectively. Both vectors contained an 8 kb ubiquitous chromatin opening element (UCOE) adjacent to the CMV promoter to isolate it from position effects. The UCOE fragment was obtained from plasmid CET210 described in U.S. Pat. No. 6,689,606 and inserted immediately upstream of the hCMV-MIE promoter-enhancer in the appropriate orientation such that the hnRNPA2 promoter was proximal to the hCMV-MIE promoter. The light chain plasmid, c13-2 contained a hygromycin-resistance gene as a selectable marker.

$1 \times 10^7$ wild-type CHO-S, KB5035-1, and KB5037-5 cells were transfected with 10 µg of linearized anti-GMCSF antibody expression plasmids c15-2 and c13-2. Stable antibody expressing clones were obtained after limiting dilution in the presence of Puromycin (10 µg/ml) and Hygromycin (600 µg/ml) for 10 days. Transfectants were screened for secretion of assembled IgG by ELISA. ELISA plates were coated with 150 ng/well of Goat Anti-Human IgG (Sigma) and human antibody was detected with Anti-Human Fc-HRP conjugate (Sigma).

To compare CMV promoter activities in the CREB expressing cells and the wild-type CHO-S cells, antibody production rates of the selected stable clones were assayed by dilution ELISA. 0.5 ml ($4 \times 10^5$ cells/ml) of stable antibody producing cells selected from wild-type CHO-S, KB5035-1, and KB5037-5 cells were seeded into 24-well plates in fresh CHO-S-SFMII media (Invitrogen). After 24 hours, 10 µl of media was taken to assay antibody concentration by ELISA for assembled IgG as above. The positive control curve was obtained using purified human antibody. The results are shown in Table 4. Clearly, the clones generated from KB5035-1 and KB5037-5 cells exhibited more than 10-fold higher antibody production rate than those from the wild-type CHO-S cells, indicating that the CREB expressing cells had much higher CMV promoter activities and produced a higher levels of antibody secretion.

TABLE 4

Antibody production rate of stable clones from wild-type CHO-S, KB5035-1, and KB5037-5 cells

| CREB expressing cells | Antibody production rate (pg/cell day) | Wild-type CHO-S cells | Antibody production rate (pg/cell day) |
| --- | --- | --- | --- |
| KB5037-2A7 | 104 | GM4-3 | 2.5 |
| KB5035-1A3 | 25 | GM4-9 | 1.25 |
| KB5035-1A7 | 25 | GM4-8 | 0.3 |
| KB5035-1E5 | 25 | GM4-5 | 0.1 |
| KB5037-1G11 | 25 | GM4-1 | <0.1 |
| KB5037-2B4 | 25 | GM4-2 | <0.1 |
| KB5037-2C5 | 25 | GM4-4 | <0.1 |
| KB5035-1B11 | 12.5 | GM4-6 | <0.1 |
| KB5035-1C2 | 12.5 | GM4-7 | <0.1 |
| KB5035-1C10 | 12.5 | GM4-10 | <0.1 |
| KB5035-1E11 | 12.5 | | |

Example 17

Protection from Apoptosis by E1B or Bcl2D when Expressed from the RSV Promoter

The genomic DNA of the Ad5 E1a gene was PCR amplified using Primer 14 and following primer:

Primer 30:    (SEQ ID NO: 46)
CGCAGTACTAGTTTATGGCCTGGGGCGTTTACAGCTC.

The DNA fragment was then digested with HindIII and SpeI, and cloned into pGL-control plasmid (Promega) between HindIII and XbaI sites to give vector KB5041 in which the E1a coding sequence is expressed from the SV40 Early promoter.

The E1b-19K gene was PCR amplified from plasmid KB5026 using Primer 25 and following primer:

Primer 31:    GAGCTATTCCAGAAGTAGTG. (SEQ ID NO: 47)

The DNA fragment was cloned into plasmid KB5013 between HindIII and XbaI sites to give vector KB5038 in which the E1b-19K gene was expressed under the control of the RSV promoter.

A double expression vector for expression of E1a and E1B-19K was constructed by digesting plasmid KB5041 with BglII and BamHI, and cloning the 1718 bp DNA fragment into KB5038 linearized by BglII digestion followed by CIP (Calf Intestinal Alkaline Phosphatase, New England BioLabs) treatment. The ligation product in which the SV40 Early promoter transcribes away from the RSV promoter was designated vector KB5045. KB5045 is similar to vector KB5029 but in KB5045, E1A is expressed from the SV40 Early promoter and E1b-19K from the RSV promoter.

The deletion mutant Bcl2D was PCR amplified from plasmid KB5028 using Primers 31 and 27. The DNA fragment was cloned into plasmid KB5013 between HindIII and XbaI to give vector KB5040. It expresses Bcl2D from the RSV promoter.

A double expression vector for the expression of E1a and Bcl2D was constructed by digesting plasmid KB5041 with BglII and BamHI, and cloning the 1718 bp DNA fragment into KB5040 linearized by BglII digestion followed by CIP treatment. The ligation product in which the SV40 promoter transcribes away from the RSV promoter was designated vector KB5047. It expresses E1A from the SV40. Early promoter and Bcl2D from the RSV promoter.

To test if E1B-19K and Bcl2D can protect cells from E1A induced apoptosis when expressed from the SV40 promoter, plasmids KB5045 and KB5047 were linearized with EcoNI between the two transcription units and used to carry out the colony formation assay. These plasmids generated equivalent numbers of stable colonies as the control plasmid KB5008. This experiment indicates that similar anti-apoptosis effects of E1b-19K and Bcl2D can be achieved using the RSV promoter to direct expression of the apoptosis protective protein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as described should not be unduly limited to such specific embodiments.

What is claimed is:

1. A method of expressing a desired antibody in a mammalian host cell comprising the steps of:

growing the mammalian host cell containing a nucleic acid, said nucleic acid comprising:

a first cistron encoding a first desired antibody polypeptide under the control of a first promoter;

a second cistron encoding a second desired antibody polypeptide under the control of the first promoter;

a third cistron encoding a CREB protein under control of a second promoter, a fourth cistron encoding an apoptosis-protective protein under control of the second promoter or optionally under control of a third promoter, wherein said second promoter or said third promoter that controls said fourth cistron comprises a CREB-binding element;

wherein the first and second cistrons are on a retroviral vector and are separated by an internal ribosome entry site (IRES), the third cistron is on the same retroviral vector or optionally on a different vector, and the fourth cistron is on the same retroviral vector or optionally on a different vector;

expressing the CREB protein at a level that can cause host cell death in the absence of the apoptosis-protective protein;

expressing the apoptosis-protective protein at a level to inhibit death of the host cell from the CREB protein; and expressing the antibody polypeptide in the mammalian host cell, wherein the production rate of the desired antibody is enhanced at least five-fold by the combination of the CREB protein and the apoptosis-protective protein.

2. A mammalian host cell comprising:

a retroviral vector, comprising a cistron encoding an antibody polypeptide under control of a first promoter and a ubiquitous chromatin opening element (UCOE) operably linked to the cistron; and a cistron encoding a CREB protein under control of a second promoter, wherein the CREB protein is present in the host cell in amounts that could cause cell death of the host cell without an apoptosis protective protein;

a cistron encoding the apoptosis-protective protein under control of a third promoter, wherein the apoptosis-protective protein is present in the host cell in amounts sufficient to inhibit death of the host cell from the transactivator and wherein said third promoter comprises a CREB-binding element; and wherein the production rate of the desired antibody in the host cell is enhanced at least five-fold by the combination of the CREB protein and the apoptosis protective protein.

* * * * *

SEQUENCE LISTING

<160> NUMBER OF SEQ ID NOS: 56

<210> SEQ ID NO 1
<211> LENGTH: 236
<212> TYPE: PRT
<213> ORGANISM: Cricetulus longicaudatus

<400> SEQUENCE: 1

```
Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Val
            20                  25                  30

Gly Asp Val Asp Ala Ala Pro Leu Gly Ala Ala Pro Thr Pro Gly Ile
        35                  40                  45

Phe Ser Phe Gln Pro Glu Ser Asn Pro Thr Pro Ala Val His Arg Asp
    50                  55                  60

Met Ala Ala Arg Thr Ser Pro Leu Arg Pro Ile Val Ala Thr Thr Gly
65                  70                  75                  80

Pro Thr Leu Ser Pro Val Pro Val Val His Leu Thr Leu Arg Arg
                85                  90                  95

Ala Gly Asp Asp Phe Ser Arg Arg Tyr Arg Arg Asp Phe Ala Glu Met
            100                 105                 110

Ser Ser Gln Leu His Leu Thr Pro Phe Thr Ala Arg Gly Arg Phe Ala
        115                 120                 125

Thr Val Val Glu Glu Leu Phe Arg Asp Gly Val Asn Trp Gly Arg Ile
    130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
            180                 185                 190

Asp Ala Phe Val Glu Leu Tyr Gly Pro Ser Val Arg Pro Leu Phe Asp
        195                 200                 205

Phe Ser Trp Leu Ser Leu Lys Thr Leu Leu Ser Leu Ala Leu Val Gly
    210                 215                 220

Ala Cys Ile Thr Leu Gly Thr Tyr Leu Gly His Lys
225                 230                 235
```

<210> SEQ ID NO 2
<211> LENGTH: 195
<212> TYPE: PRT
<213> ORGANISM: Cricetulus longicaudatus

<400> SEQUENCE: 2

```
Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Val
            20                  25                  30

Gly Asp Val Asp Ala Ala Ala Ala Ala Ser Pro Val Pro Pro Val
        35                  40                  45

Val His Leu Thr Leu Arg Arg Ala Gly Asp Asp Phe Ser Arg Arg Tyr
    50                  55                  60

Arg Arg Asp Phe Ala Glu Met Ser Ser Gln Leu His Leu Thr Pro Phe
65                  70                  75                  80
```

```
Thr Ala Arg Gly Arg Phe Ala Thr Val Val Glu Glu Leu Phe Arg Asp
                85                  90                  95

Gly Val Asn Trp Gly Arg Ile Val Ala Phe Phe Glu Phe Gly Gly Val
            100                 105                 110

Met Cys Val Glu Ser Val Asn Arg Glu Met Ser Pro Leu Val Asp Asn
        115                 120                 125

Ile Ala Leu Trp Met Thr Glu Tyr Leu Asn Arg His Leu His Thr Trp
    130                 135                 140

Ile Gln Asp Asn Gly Gly Trp Asp Ala Phe Val Glu Leu Tyr Gly Pro
145                 150                 155                 160

Ser Val Arg Pro Leu Phe Asp Phe Ser Trp Leu Ser Leu Lys Thr Leu
                165                 170                 175

Leu Ser Leu Ala Leu Val Gly Ala Cys Ile Thr Leu Gly Thr Tyr Leu
            180                 185                 190

Gly His Lys
        195

<210> SEQ ID NO 3
<211> LENGTH: 588
<212> TYPE: DNA
<213> ORGANISM: Cricetulus longicaudatus

<400> SEQUENCE: 3
atggctcaag ctgggagaac agggtatgat aaccgagaga tcgtgatgaa gtacatccat     60
tataagctgt cacagagggg ctacgagtgg gatgtgggag atgtggacgc cgcggccgcg    120
gccgcgagcc ccgtgccacc tgtggtccac ctgaccctcc gccgggctgg ggatgacttc    180
tcccgtcgct accgtcgcga cttcgcggag atgtccagtc agctgcacct gacgcccttc    240
accgcgaggg gacgctttgc tacggtggtg gaggaactct tcaggatggg ggtgaactgg    300
gggaggattg tggccttctt tgagttcggt ggggtcatgt gtgtggagag cgtcaacagg    360
gagatgtcac ccctggtgga caacatcgcc ctgtggatga ccgagtacct gaaccggcat    420
ctgcacacct ggatccagga taacggaggc tgggacgcat ttgtggaact gtacggcccc    480
agtgtgaggc ctctgtttga tttctcttgg ctgtctctga agaccctgct cagcctggcc    540
ctggtcgggg cctgcatcac tctgggtacc tacctgggcc acaagtga                588

<210> SEQ ID NO 4
<211> LENGTH: 289
<212> TYPE: PRT
<213> ORGANISM: Human adenovirus type 5

<400> SEQUENCE: 4

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu His Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro His Leu Ser
            85                  90                  95

Arg Gln Pro Glu Gln Pro Glu Gln Arg Ala Leu Gly Pro Val Ser Met
            100                 105                 110
```

```
Pro Asn Leu Val Pro Glu Val Ile Asp Leu Thr Gly His Glu Ala Gly
    115                 120                 125

Phe Pro Pro Ser Asp Asp Glu Asp Glu Glu Gly Glu Glu Phe Val Leu
    130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
    195                 200                 205

Met Ala Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
    275                 280                 285

Pro

<210> SEQ ID NO 5
<211> LENGTH: 986
<212> TYPE: DNA
<213> ORGANISM: Human adenovirus type 5

<400> SEQUENCE: 5
atgagacata ttatctgcca cggaggtgtt attaccgaag aaatggccgc cagtcttttg      60
gaccagctga tcgaagaggt actggctgat aatcttccac ctcctagcca ttttgaacca    120
cctacccttc acgaactgca tgatttagac gtgacggccc ccgaagatcc caacgaggag    180
gcggtttcgc agatttttcc cgactctgta atgttggcgg tgcaggaagg gattgactta    240
ctcacttttc cgccggcgcc cggttctccg gagccgcctc acctttcccg gcagcccgag    300
cagccggagc agagagcctt gggtccggtt tctatgccaa accttgtacc ggaggtgatc    360
gatcttaccg ccacgaggc tggctttcca cccagtgacg acgaggatga agagggtgag    420
gagtttgtgt tagattatgt ggagcacccc gggcacggtt gcaggtcttg tcattatcac    480
cggaggaata cggggaccc agatattatg tgttcgcttt gctatatgag gacctgtggc    540
atgtttgtct acagtaagtg aaaattatgg gcagtgggtg atagagtggt gggtttggtg    600
tggtaatttt ttttttaatt tttacagttt tgtggtttaa agaattttgt attgtgattt    660
ttttaaaagg tcctgtgtct gaacctgagc ctgagcccga ccagaaccg agcctgcaa     720 gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataa                                         986
```

```
<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccgaattcg ccgccaccat gagacatatt atctgccac                              39

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccgtcgacc ttatggcctg gggcgttt                                          28

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccggtaccg ccgccaccat gagacatatt atctgccac                              39

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccgcggccg ccttatggcc tggggcgttt                                        30

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggaggtgatc gatcttaccg gccac                                             25

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctacccttc acgaactgca tgatttagac gtgacg                                 36
```

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 12

```
cgtcacgtct aaatcatgca gttcgtgaag ggtagg                              36
```

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

```
cccgaattcg ccgccaccat ggaggcttgg gagtgttt                            38
```

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 14

```
cccgtcgacc aacattcatt cccgagggt                                      29
```

<210> SEQ ID NO 15
<211> LENGTH: 558
<212> TYPE: DNA
<213> ORGANISM: Human adenovirus type 5

<400> SEQUENCE: 15

```
gaattcgccg ccaccatgga ggcttgggag tgtttggaag attttctgc tgtgcgtaac     60
ttgctggaac agagctctaa cagtacctct tggttttgga ggtttctgtg ggctcatcc    120
caggcaaagt tagtctgcag aattaaggag gattacaagt gggaatttga agagcttttg   180
aaatcctgtg gtgagctgtt tgattctttg aatctgggtc caggcgcct tttccaagag    240
aaggtcatca agactttgga tttttccaca ccggggcgcg ctgcggctgc tgttgctttt   300
ttgagtttta taaggataa atggagcgaa gaaacccatc tgagcggggg gtacctgctg    360
gattttctgg ccatgcatct gtggagagcg gttgtgagac acaagaatcg cctgctactg   420
ttgtcttccg tccgcccggc gataataccg acggaggagc agcagcagca gcaggaggaa   480
gccaggcggc ggcggcagga gcagagccca tggaacccga gaccggcct ggaccctcgg    540
gaatgaatgt tggtcgac                                                 558
```

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 16

```
cccgtcgacg ccgccaccat gccgcccaaa acccccg                            38
```

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
cccgcggccg ccggtcctga gatcctcatt tc                                   32

<210> SEQ ID NO 18
<211> LENGTH: 2824
<212> TYPE: DNA
<213> ORGANISM: Homo sapiens
<220> FEATURE:
<221> NAME/KEY: CDS
<222> LOCATION: (16)..(2799)

<400> SEQUENCE: 18

```
gtcgacgccg ccacc atg ccg ccc aaa acc ccc cga aaa acg gcc gcc acc        51
                 Met Pro Pro Lys Thr Pro Arg Lys Thr Ala Ala Thr
                 1               5                   10 gcc gcc gct gcc gcc gcg gaa ccc ccg gca ccg ccg ccg ccc cct             99
Ala Ala Ala Ala Ala Ala Glu Pro Pro Ala Pro Pro Pro Pro Pro
                15                  20                  25 cct gag gag gac cca gag cag gac agc ggc ccg gag gac ctg cct ctc        147
Pro Glu Glu Asp Pro Glu Gln Asp Ser Gly Pro Glu Asp Leu Pro Leu
         30                  35                  40 gtc agg ctt gag ttt gaa gaa aca gaa gaa cct gat ttt act gca tta        195
Val Arg Leu Glu Phe Glu Glu Thr Glu Glu Pro Asp Phe Thr Ala Leu
45                  50                  55                  60 tgt cag aaa tta aag ata cca gat cat gtc aga gag aga gct tgg tta        243
Cys Gln Lys Leu Lys Ile Pro Asp His Val Arg Glu Arg Ala Trp Leu
                 65                  70                  75 act tgg gag aaa gtt tca tct gtg gat gga gta ttg gga ggt tat att        291
Thr Trp Glu Lys Val Ser Ser Val Asp Gly Val Leu Gly Gly Tyr Ile
             80                  85                  90 caa aag aaa aag gaa ctg tgg gga atc tgt atc ttt att gca cga gtt        339
Gln Lys Lys Lys Glu Leu Trp Gly Ile Cys Ile Phe Ile Ala Arg Val
             95                  100                 105 gac cta gat gag atg tcg ttc act tta ctg agc tac aga aaa aca tac        387
Asp Leu Asp Glu Met Ser Phe Thr Leu Leu Ser Tyr Arg Lys Thr Tyr
     110                 115                 120 gaa atc agt gtc cat aaa ttc ttt aac tta cta aaa gaa att gat acc        435
Glu Ile Ser Val His Lys Phe Phe Asn Leu Leu Lys Glu Ile Asp Thr
125                 130                 135                 140 agt acc aaa gtt gat aat gct atg tca aga ctg ttg aag aag tat gat        483
Ser Thr Lys Val Asp Asn Ala Met Ser Arg Leu Leu Lys Lys Tyr Asp
                 145                 150                 155 gta ttg ttt gca ctc ttc agc aaa ttg gaa agg aca tgt gaa ctt ata        531
Val Leu Phe Ala Leu Phe Ser Lys Leu Glu Arg Thr Cys Glu Leu Ile
             160                 165                 170 tat ttg aca caa ccc agc agt tcg ata tct act gaa ata aat tct gca        579
Tyr Leu Thr Gln Pro Ser Ser Ser Ile Ser Thr Glu Ile Asn Ser Ala
             175                 180                 185 ttg gtg cta aaa gtt tct tgg atc aca ttt tta tta gct aaa ggg gaa        627
Leu Val Leu Lys Val Ser Trp Ile Thr Phe Leu Leu Ala Lys Gly Glu
     190                 195                 200 gta tta caa atg gaa gat gat ctg gtg att tca ttt cag tta atg cta        675
Val Leu Gln Met Glu Asp Asp Leu Val Ile Ser Phe Gln Leu Met Leu
205                 210                 215                 220
```

```
tgt gtc ctt gac tat ttt att aaa ctc tca cct ccc atg ttg ctc aaa      723
Cys Val Leu Asp Tyr Phe Ile Lys Leu Ser Pro Pro Met Leu Leu Lys
            225                 230                 235 gaa cca tat aaa aca gct gtt ata ccc att aat ggt tca cct cga aca      771
Glu Pro Tyr Lys Thr Ala Val Ile Pro Ile Asn Gly Ser Pro Arg Thr
        240                 245                 250 ccc agg cga ggt cag aac agg agt gca cgg ata gca aaa caa cta gaa      819
Pro Arg Arg Gly Gln Asn Arg Ser Ala Arg Ile Ala Lys Gln Leu Glu
    255                 260                 265 aat gat aca aga att att gaa gtt ctc tgt aaa gaa cat gaa tgt aat      867
Asn Asp Thr Arg Ile Ile Glu Val Leu Cys Lys Glu His Glu Cys Asn
270                 275                 280 ata gat gag gtg aaa aat gtt tat ttc aaa aat ttt ata cct ttt atg      915
Ile Asp Glu Val Lys Asn Val Tyr Phe Lys Asn Phe Ile Pro Phe Met
285                 290                 295                 300 aat tct ctt gga ctt gta aca tct aat gga ctt cca gag gtt gaa aat      963
Asn Ser Leu Gly Leu Val Thr Ser Asn Gly Leu Pro Glu Val Glu Asn
            305                 310                 315 ctt tct aaa cga tac gaa gaa att tat ctt aaa aat aaa gat cta gat     1011
Leu Ser Lys Arg Tyr Glu Glu Ile Tyr Leu Lys Asn Lys Asp Leu Asp
        320                 325                 330 cga aga tta ttt ttg gat cat gat aaa act ctt cag act gat tct ata     1059
Arg Arg Leu Phe Leu Asp His Asp Lys Thr Leu Gln Thr Asp Ser Ile
    335                 340                 345 gac agt ttt gaa aca cag aga aca cca cga aaa agt aac ctt gat gaa     1107
Asp Ser Phe Glu Thr Gln Arg Thr Pro Arg Lys Ser Asn Leu Asp Glu
350                 355                 360 gag gtg aat ata att cct cca cac act cca gtt agg act gtt atg aac     1155
Glu Val Asn Ile Ile Pro Pro His Thr Pro Val Arg Thr Val Met Asn
365                 370                 375                 380 act atc caa caa tta atg atg att tta aat tct gca agt gat caa cct     1203
Thr Ile Gln Gln Leu Met Met Ile Leu Asn Ser Ala Ser Asp Gln Pro
            385                 390                 395 tca gaa aat ctg att tcc tat ttt aac aac tgc aca gtg aat cca aaa     1251
Ser Glu Asn Leu Ile Ser Tyr Phe Asn Asn Cys Thr Val Asn Pro Lys
        400                 405                 410 gaa agt ata ctg aaa aga gtg aag gat ata gga tac atc ttt aaa gag     1299
Glu Ser Ile Leu Lys Arg Val Lys Asp Ile Gly Tyr Ile Phe Lys Glu
    415                 420                 425 aaa ttt gct aaa gct gtg gga cag ggt tgt gtc gaa att gga tca cag     1347
Lys Phe Ala Lys Ala Val Gly Gln Gly Cys Val Glu Ile Gly Ser Gln
430                 435                 440 cga tac aaa ctt gga gtt cgc ttg tat tac cga gta atg gaa tcc atg     1395
Arg Tyr Lys Leu Gly Val Arg Leu Tyr Tyr Arg Val Met Glu Ser Met
445                 450                 455                 460 ctt aaa tca gaa gaa gaa cga tta tcc att caa aat ttt agc aaa ctt     1443
Leu Lys Ser Glu Glu Glu Arg Leu Ser Ile Gln Asn Phe Ser Lys Leu
            465                 470                 475 ctg aat gac aac att ttt cat atg tct tta ttg gcg tgc gct ctt gag     1491
Leu Asn Asp Asn Ile Phe His Met Ser Leu Leu Ala Cys Ala Leu Glu
        480                 485                 490 gtt gta atg gcc aca tat agc aga agt aca tct cag aat ctt gat tct     1539
Val Val Met Ala Thr Tyr Ser Arg Ser Thr Ser Gln Asn Leu Asp Ser
    495                 500                 505 gga aca gat ttg tct ttc cca tgg att ctg aat gtg ctt aat tta aaa     1587
Gly Thr Asp Leu Ser Phe Pro Trp Ile Leu Asn Val Leu Asn Leu Lys
510                 515                 520 gcc ttt gat ttt tac aaa gtg atc gaa agt ttt atc aaa gca gaa ggc     1635
Ala Phe Asp Phe Tyr Lys Val Ile Glu Ser Phe Ile Lys Ala Glu Gly
525                 530                 535                 540
```

```
aac ttg aca aga gaa atg ata aaa cat tta gaa cga tgt gaa cat cga   1683
Asn Leu Thr Arg Glu Met Ile Lys His Leu Glu Arg Cys Glu His Arg
            545                 550                 555 atc atg gaa tcc ctt gca tgg ctc tca gat tca cct tta ttt gat ctt   1731
Ile Met Glu Ser Leu Ala Trp Leu Ser Asp Ser Pro Leu Phe Asp Leu
560                 565                 570 att aaa caa tca aag gac cga gaa gga cca act gat cac ctt gaa tct   1779
Ile Lys Gln Ser Lys Asp Arg Glu Gly Pro Thr Asp His Leu Glu Ser
        575                 580                 585 gct tgt cct ctt aat ctt cct ctc cag aat aat cac act gca gca gat   1827
Ala Cys Pro Leu Asn Leu Pro Leu Gln Asn Asn His Thr Ala Ala Asp
    590                 595                 600 atg tat ctt tct cct gta aga tct cca aag aaa aaa ggt tca act acg   1875
Met Tyr Leu Ser Pro Val Arg Ser Pro Lys Lys Lys Gly Ser Thr Thr
605                 610                 615                 620 cgt gta aat tct act gca aat gca gag aca caa gca acc tca gcc ttc   1923
Arg Val Asn Ser Thr Ala Asn Ala Glu Thr Gln Ala Thr Ser Ala Phe
        625                 630                 635 cag acc cag aag cca ttg aaa tct acc tct ctt tca ctg ttt tat aaa   1971
Gln Thr Gln Lys Pro Leu Lys Ser Thr Ser Leu Ser Leu Phe Tyr Lys
    640                 645                 650 aaa gtg tat cgg cta gcc tat ctc cgg cta aat aca ctt tgt gaa cgc   2019
Lys Val Tyr Arg Leu Ala Tyr Leu Arg Leu Asn Thr Leu Cys Glu Arg
655                 660                 665 ctt ctg tct gag cac cca gaa tta gaa cat atc atc tgg acc ctt ttc   2067
Leu Leu Ser Glu His Pro Glu Leu Glu His Ile Ile Trp Thr Leu Phe
        670                 675                 680 cag cac acc ctg cag aat gag tat gaa ctc atg aga gac agg cat ttg   2115
Gln His Thr Leu Gln Asn Glu Tyr Glu Leu Met Arg Asp Arg His Leu
685                 690                 695                 700 gac caa att atg atg tgt tcc atg tat ggc ata tgc aaa gtg aag aat   2163
Asp Gln Ile Met Met Cys Ser Met Tyr Gly Ile Cys Lys Val Lys Asn
            705                 710                 715 ata gac ctt aaa ttc aaa atc att gta aca gca tac aag gat ctt cct   2211
Ile Asp Leu Lys Phe Lys Ile Ile Val Thr Ala Tyr Lys Asp Leu Pro
                720                 725                 730 cat gct gtt cag gag aca ttc aaa cgt gtt ttg atc aaa gaa gag gag   2259
His Ala Val Gln Glu Thr Phe Lys Arg Val Leu Ile Lys Glu Glu Glu
        735                 740                 745 tat gat tct att ata gta ttc tat aac tcg gtc ttc atg cag aga ctg   2307
Tyr Asp Ser Ile Ile Val Phe Tyr Asn Ser Val Phe Met Gln Arg Leu
750                 755                 760 aaa aca aat att ttg cag tat gct tcc acc agg ccc cct acc ttg tca   2355
Lys Thr Asn Ile Leu Gln Tyr Ala Ser Thr Arg Pro Pro Thr Leu Ser
765                 770                 775                 780 cca ata cct cac att cct cga agc cct tac aag ttt cct agt tca ccc   2403
Pro Ile Pro His Ile Pro Arg Ser Pro Tyr Lys Phe Pro Ser Ser Pro
            785                 790                 795 tta cgg att cct gga ggg aac atc tat att tca ccc ctg aag agt cca   2451
Leu Arg Ile Pro Gly Gly Asn Ile Tyr Ile Ser Pro Leu Lys Ser Pro
                800                 805                 810 tat aaa att tca gaa ggt ctg cca aca cca aca aaa atg act cca aga   2499
Tyr Lys Ile Ser Glu Gly Leu Pro Thr Pro Thr Lys Met Thr Pro Arg
        815                 820                 825 tca aga atc tta gta tca att ggt gaa tca ttc ggg act tct gag aag   2547
Ser Arg Ile Leu Val Ser Ile Gly Glu Ser Phe Gly Thr Ser Glu Lys
830                 835                 840 ttc cag aaa ata aat cag atg gta tgt aac agc gac cgt gtg ctc aaa   2595
Phe Gln Lys Ile Asn Gln Met Val Cys Asn Ser Asp Arg Val Leu Lys
845                 850                 855                 860
```

```
aga agt gct gaa gga agc aac cct cct aaa cca ctg aaa aaa cta cgc    2643
Arg Ser Ala Glu Gly Ser Asn Pro Pro Lys Pro Leu Lys Lys Leu Arg
                865                 870                 875 ttt gat att gaa gga tca gat gaa gca gat gga agt aaa cat ctc cca    2691
Phe Asp Ile Glu Gly Ser Asp Glu Ala Asp Gly Ser Lys His Leu Pro
            880                 885                 890 gga gag tcc aaa ttt cag cag aaa ctg gca gaa atg act tct act cga    2739
Gly Glu Ser Lys Phe Gln Gln Lys Leu Ala Glu Met Thr Ser Thr Arg
        895                 900                 905 aca cga atg caa aag cag aaa atg aat gat agc atg gat acc tca aac    2787
Thr Arg Met Gln Lys Gln Lys Met Asn Asp Ser Met Asp Thr Ser Asn
    910                 915                 920 aag gaa gag aaa tgaggatctc aggaccggcg gccgc                        2824
Lys Glu Glu Lys
925

<210> SEQ ID NO 19
<211> LENGTH: 928
<212> TYPE: PRT
<213> ORGANISM: Homo sapiens

<400> SEQUENCE: 19

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
                20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Arg Val Asp Leu Asp Glu
            100                 105                 110

Met Ser Phe Thr Leu Leu Ser Tyr Arg Lys Thr Tyr Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270
```

-continued

```
Ile Ile Glu Val Leu Cys Lys Glu His Glu Cys Asn Ile Asp Val
        275                 280                 285
Lys Asn Val Tyr Phe Lys Asn Phe Ile Pro Phe Met Asn Ser Leu Gly
        290                 295                 300
Leu Val Thr Ser Asn Gly Leu Pro Glu Val Glu Asn Leu Ser Lys Arg
305                 310                 315                 320
Tyr Glu Glu Ile Tyr Leu Lys Asn Lys Asp Leu Asp Arg Arg Leu Phe
                325                 330                 335
Leu Asp His Asp Lys Thr Leu Gln Thr Asp Ser Ile Asp Ser Phe Glu
                340                 345                 350
Thr Gln Arg Thr Pro Arg Lys Ser Asn Leu Asp Glu Glu Val Asn Ile
                355                 360                 365
Ile Pro Pro His Thr Pro Val Arg Thr Val Met Asn Thr Ile Gln Gln
370                 375                 380
Leu Met Met Ile Leu Asn Ser Ala Ser Asp Gln Pro Ser Glu Asn Leu
385                 390                 395                 400
Ile Ser Tyr Phe Asn Asn Cys Thr Val Asn Pro Lys Glu Ser Ile Leu
                405                 410                 415
Lys Arg Val Lys Asp Ile Gly Tyr Ile Phe Lys Glu Lys Phe Ala Lys
                420                 425                 430
Ala Val Gly Gln Gly Cys Val Glu Ile Gly Ser Gln Arg Tyr Lys Leu
                435                 440                 445
Gly Val Arg Leu Tyr Tyr Arg Val Met Glu Ser Met Leu Lys Ser Glu
450                 455                 460
Glu Glu Arg Leu Ser Ile Gln Asn Phe Ser Lys Leu Leu Asn Asp Asn
465                 470                 475                 480
Ile Phe His Met Ser Leu Leu Ala Cys Ala Leu Glu Val Val Met Ala
                485                 490                 495
Thr Tyr Ser Arg Ser Thr Ser Gln Asn Leu Asp Ser Gly Thr Asp Leu
                500                 505                 510
Ser Phe Pro Trp Ile Leu Asn Val Leu Asn Leu Lys Ala Phe Asp Phe
                515                 520                 525
Tyr Lys Val Ile Glu Ser Phe Ile Lys Ala Glu Gly Asn Leu Thr Arg
                530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
                565                 570                 575
Lys Asp Arg Glu Gly Pro Thr Asp His Leu Glu Ser Ala Cys Pro Leu
                580                 585                 590
Asn Leu Pro Leu Gln Asn Asn His Thr Ala Ala Asp Met Tyr Leu Ser
                595                 600                 605
Pro Val Arg Ser Pro Lys Lys Lys Gly Ser Thr Thr Arg Val Asn Ser
610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
                645                 650                 655
Leu Ala Tyr Leu Arg Leu Asn Thr Leu Cys Glu Arg Leu Leu Ser Glu
                660                 665                 670
His Pro Glu Leu Glu His Ile Ile Trp Thr Leu Phe Gln His Thr Leu
                675                 680                 685
Gln Asn Glu Tyr Glu Leu Met Arg Asp Arg His Leu Asp Gln Ile Met
                690                 695                 700
```

```
Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925

<210> SEQ ID NO 20
<211> LENGTH: 1010
<212> TYPE: DNA
<213> ORGANISM: Rattus sp.
<220> FEATURE:
<221> NAME/KEY: CDS
<222> LOCATION: (16)..(996)

<400> SEQUENCE: 20
gaattcgccg ccacc atg acc atg gac tct gga gca gac aac cag cag agt      51
                Met Thr Met Asp Ser Gly Ala Asp Asn Gln Gln Ser
                1               5                   10 gga gat gca gct gta aca gaa gct gaa aac caa caa atg aca gtt caa       99
Gly Asp Ala Ala Val Thr Glu Ala Glu Asn Gln Gln Met Thr Val Gln
        15                  20                  25 gcc cag cca cag att gcc aca tta gcc cag gta tct atg cca gca gct      147
Ala Gln Pro Gln Ile Ala Thr Leu Ala Gln Val Ser Met Pro Ala Ala
    30                  35                  40 cat gca aca tca tct gct ccc acc gta act cta gta cag ctg ccc aat      195
His Ala Thr Ser Ser Ala Pro Thr Val Thr Leu Val Gln Leu Pro Asn
45                  50                  55                  60 ggg cag aca gtt caa gtc cat gga gtc att cag gcg gcc cag cca tca      243
Gly Gln Thr Val Gln Val His Gly Val Ile Gln Ala Ala Gln Pro Ser
                65                  70                  75 gtt att cag tct cca caa gtc caa aca gtt cag att tca act att gca      291
Val Ile Gln Ser Pro Gln Val Gln Thr Val Gln Ile Ser Thr Ile Ala
            80                  85                  90 gaa agt gaa gat tca cag gag tca gtg gat agt gta act gat tcc caa      339
Glu Ser Glu Asp Ser Gln Glu Ser Val Asp Ser Val Thr Asp Ser Gln
        95                  100                 105
```

```
aag cga agg gaa att ctt tca agg agg cct tcc ttc agg aaa att ttg      387
Lys Arg Arg Glu Ile Leu Ser Arg Arg Pro Ser Phe Arg Lys Ile Leu
    110                 115                 120 aat gac tta tct tct gat gca cca gga gtg cca agg att gaa gaa gag      435
Asn Asp Leu Ser Ser Asp Ala Pro Gly Val Pro Arg Ile Glu Glu Glu
125                 130                 135                 140 aag tct gaa gag gag gct tca gca cct gcc atc acc gct gta gcg gtg      483
Lys Ser Glu Glu Glu Ala Ser Ala Pro Ala Ile Thr Ala Val Ala Val
                145                 150                 155 cca acg cca att tac cgg act agc agt gga cag tat att acc att acc      531
Pro Thr Pro Ile Tyr Arg Thr Ser Ser Gly Gln Tyr Ile Thr Ile Thr
            160                 165                 170 cag aga gga gca ata cag ctg gct agc aat ggt acc gat ggg gta cag      579
Gln Arg Gly Ala Ile Gln Leu Ala Ser Asn Gly Thr Asp Gly Val Gln
        175                 180                 185 ggc ctg caa aca tta acc atg gcc aat gca gca gcc act cag ccg ggt      627
Gly Leu Gln Thr Leu Thr Met Ala Asn Ala Ala Ala Thr Gln Pro Gly
    190                 195                 200 act acc att cta cag tat gca cag acc act gat gga cag cag atc tta      675
Thr Thr Ile Leu Gln Tyr Ala Gln Thr Thr Asp Gly Gln Gln Ile Leu
205                 210                 215                 220 gtg ccc agc aac caa gtt gtt gtt caa gct gcc tct gga gac gta caa      723
Val Pro Ser Asn Gln Val Val Val Gln Ala Ala Ser Gly Asp Val Gln
                225                 230                 235 aca tac cag att cgc aca gca ccc act agc act att gcc cct gga gtt      771
Thr Tyr Gln Ile Arg Thr Ala Pro Thr Ser Thr Ile Ala Pro Gly Val
            240                 245                 250 gtt atg gca tcc tcc cca gca ctt cct aca cag cct gct gaa gaa gca      819
Val Met Ala Ser Ser Pro Ala Leu Pro Thr Gln Pro Ala Glu Glu Ala
        255                 260                 265 gca cga aag aga gag gtc cgt cta atg aag aac agg gaa gca gct cgt      867
Ala Arg Lys Arg Glu Val Arg Leu Met Lys Asn Arg Glu Ala Ala Arg
    270                 275                 280 gag tgt cgt aga aag aag aaa gaa tat gtg aaa tgt tta gaa aac aga      915
Glu Cys Arg Arg Lys Lys Lys Glu Tyr Val Lys Cys Leu Glu Asn Arg
285                 290                 295                 300 gtg gca gtg ctt gaa aat caa aac aag aca ttg att gag gag cta aaa      963
Val Ala Val Leu Glu Asn Gln Asn Lys Thr Leu Ile Glu Glu Leu Lys
                305                 310                 315 gca ctt aag gac ctt tac tgc cac aaa tca gat taatttgggt cgac         1010
Ala Leu Lys Asp Leu Tyr Cys His Lys Ser Asp
            320                 325

<210> SEQ ID NO 21
<211> LENGTH: 327
<212> TYPE: PRT
<213> ORGANISM: Rattus sp.

<400> SEQUENCE: 21

Met Thr Met Asp Ser Gly Ala Asp Asn Gln Gln Ser Gly Asp Ala Ala
1               5                   10                  15

Val Thr Glu Ala Glu Asn Gln Gln Met Thr Val Gln Ala Gln Pro Gln
            20                  25                  30

Ile Ala Thr Leu Ala Gln Val Ser Met Pro Ala Ala His Ala Thr Ser
        35                  40                  45

Ser Ala Pro Thr Val Thr Leu Val Gln Leu Pro Asn Gly Gln Thr Val
    50                  55                  60

Gln Val His Gly Val Ile Gln Ala Ala Gln Pro Ser Val Ile Gln Ser
65                  70                  75                  80
```

-continued

```
Pro Gln Val Gln Thr Val Gln Ile Ser Thr Ile Ala Glu Ser Glu Asp
                 85                  90                  95
Ser Gln Glu Ser Val Asp Ser Val Thr Asp Ser Gln Lys Arg Arg Glu
            100                 105                 110
Ile Leu Ser Arg Arg Pro Ser Phe Arg Lys Ile Leu Asn Asp Leu Ser
        115                 120                 125
Ser Asp Ala Pro Gly Val Pro Arg Ile Glu Glu Lys Ser Glu Glu
    130                 135                 140
Glu Ala Ser Ala Pro Ala Ile Thr Ala Val Ala Val Pro Thr Pro Ile
145                 150                 155                 160
Tyr Arg Thr Ser Ser Gly Gln Tyr Ile Thr Ile Thr Gln Arg Gly Ala
                165                 170                 175
Ile Gln Leu Ala Ser Asn Gly Thr Asp Gly Val Gln Gly Leu Gln Thr
            180                 185                 190
Leu Thr Met Ala Asn Ala Ala Ala Thr Gln Pro Gly Thr Thr Ile Leu
        195                 200                 205
Gln Tyr Ala Gln Thr Thr Asp Gly Gln Gln Ile Leu Val Pro Ser Asn
    210                 215                 220
Gln Val Val Gln Ala Ala Ser Gly Asp Val Gln Thr Tyr Gln Ile
225                 230                 235                 240
Arg Thr Ala Pro Thr Ser Thr Ile Ala Pro Gly Val Val Met Ala Ser
                245                 250                 255
Ser Pro Ala Leu Pro Thr Gln Pro Ala Glu Glu Ala Ala Arg Lys Arg
            260                 265                 270
Glu Val Arg Leu Met Lys Asn Arg Glu Ala Ala Arg Glu Cys Arg Arg
        275                 280                 285
Lys Lys Lys Glu Tyr Val Lys Cys Leu Glu Asn Arg Val Ala Val Leu
    290                 295                 300
Glu Asn Gln Asn Lys Thr Leu Ile Glu Glu Leu Lys Ala Leu Lys Asp
305                 310                 315                 320
Leu Tyr Cys His Lys Ser Asp
                325

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cccgaattcg ccgccaccat gaccatggac tctggagcag aca                     43

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcgacccaa attaatctga tttgtggcag                                    30

<210> SEQ ID NO 24
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
gtcaagcaag cttgccgcca ccatgagaca tattatctgc cacgg                    45

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcagtctcg agttatggcc tggggcgttt acagctc                             37

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cacctaccct tcacgaactg catgatttag acgtgacggc c                        41

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggccgtcacg tctaaatcat gcagttcgtg aagggtaggt g                        41

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cggaggtgat cgatcttacc ggccacgagg ctggctttcc ac                       42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggaaagcc agcctcgtgg ccggtaagat cgatcacctc cg                       42

<210> SEQ ID NO 30
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 30
gtcaagcaag cttgccgcca ccatgaccat ggaatctgga gc                        42

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgcagtggat ccttaatctg atttgtggca gtaaagg                              37

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtcattcaaa attttcctga aggaaggcct ccttgaaag                            39

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tctttcaagg aggccttcct tcaggaaaat tttgaatgac                           40

<210> SEQ ID NO 34
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggcattccaa gcttactgtt ggtaaagccg ccaccatgga ggcttgggag tgtttgg        57

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatcgactct agatcattcc cgagggtcca ggccgg                               36

<210> SEQ ID NO 36
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 36
taaagccacc atggctcaag ctgggagaac agggtatg                            38

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatcgactct agatcacttg tggcccaggt aggtaccc                            38

<210> SEQ ID NO 38
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgggagatg tggacgccgc ggccgcggcc gcgagccccg tgccacctgt ggtcc         55

<210> SEQ ID NO 39
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggaccacagg tggcacgggg ctcgcggccg cggccgcggc gtccacatct cccac         55

<210> SEQ ID NO 40
<211> LENGTH: 891
<212> TYPE: DNA
<213> ORGANISM: Human adenovirus type 5
<220> FEATURE:
<221> NAME/KEY: CDS
<222> LOCATION: (16)..(882)

<400> SEQUENCE: 40
aagcttgccg ccacc atg aga cat att atc tgc cac gga ggt gtt att acc    51
                Met Arg His Ile Ile Cys His Gly Gly Val Ile Thr
                1               5                   10 gaa gaa atg gcc gcc agt ctt ttg gac cag ctg atc gaa gag gta ctg     99
Glu Glu Met Ala Ala Ser Leu Leu Asp Gln Leu Ile Glu Glu Val Leu
            15                  20                  25 gct gat aat ctt cca cct cct agc cat ttt gaa cca cct acc ctt cac    147
Ala Asp Asn Leu Pro Pro Pro Ser His Phe Glu Pro Pro Thr Leu His
        30                  35                  40 gaa ctg tat gat tta gac gtg acg gcc ccc gaa gat ccc aac gag gag   195
Glu Leu Tyr Asp Leu Asp Val Thr Ala Pro Glu Asp Pro Asn Glu Glu
45                  50                  55                  60 gcg gtt tcg cag att ttt ccc gac tct gta atg ttg gcg gtg cag gaa   243
Ala Val Ser Gln Ile Phe Pro Asp Ser Val Met Leu Ala Val Gln Glu
                65                  70                  75
```

```
ggg att gac tta ctc act ttt ccg ccg gcg ccc ggt tct ccg gag ccg    291
Gly Ile Asp Leu Leu Thr Phe Pro Pro Ala Pro Gly Ser Pro Glu Pro
             80                  85                  90 cct cac ctt tcc cgg cag ccc gag cag ccg gag cag aga gcc ttg ggt    339
Pro His Leu Ser Arg Gln Pro Glu Gln Pro Glu Gln Arg Ala Leu Gly
             95                 100                 105 ccg gtt tct atg cca aac ctt gta ccg gag gtg atc gat ctt acc tgc    387
Pro Val Ser Met Pro Asn Leu Val Pro Glu Val Ile Asp Leu Thr Cys
        110                 115                 120 cac gag gct ggc ttt cca ccc agt gac gac gag gat gaa gag ggt gag    435
His Glu Ala Gly Phe Pro Pro Ser Asp Asp Glu Asp Glu Glu Gly Glu
125                 130                 135                 140 gag ttt gtg tta gat tat gtg gag cac ccc ggg cac ggt tgc agg tct    483
Glu Phe Val Leu Asp Tyr Val Glu His Pro Gly His Gly Cys Arg Ser
            145                 150                 155 tgt cat tat cac cgg agg aat acg ggg gac cca gat att atg tgt tcg    531
Cys His Tyr His Arg Arg Asn Thr Gly Asp Pro Asp Ile Met Cys Ser
            160                 165                 170 ctt tgc tat atg agg acc tgt ggc atg ttt gtc tac agt cct gtg tct    579
Leu Cys Tyr Met Arg Thr Cys Gly Met Phe Val Tyr Ser Pro Val Ser
        175                 180                 185 gaa cct gag cct gag ccc gag cca gaa ccg gag cct gca aga cct acc    627
Glu Pro Glu Pro Glu Pro Glu Pro Glu Pro Glu Pro Ala Arg Pro Thr
190                 195                 200 cgc cgt cct aaa atg gcg cct gct atc ctg aga cgc ccg aca tca cct    675
Arg Arg Pro Lys Met Ala Pro Ala Ile Leu Arg Arg Pro Thr Ser Pro
205                 210                 215                 220 gtg tct aga gaa tgc aat agt agt acg gat agc tgt gac tcc ggt cct    723
Val Ser Arg Glu Cys Asn Ser Ser Thr Asp Ser Cys Asp Ser Gly Pro
            225                 230                 235 tct aac aca cct cct gag ata cac ccg gtg gtc ccg ctg tgc ccc att    771
Ser Asn Thr Pro Pro Glu Ile His Pro Val Val Pro Leu Cys Pro Ile
        240                 245                 250 aaa cca gtt gcc gtg aga gtt ggt ggg cgt cgc cag gct gtg gaa tgt    819
Lys Pro Val Ala Val Arg Val Gly Gly Arg Arg Gln Ala Val Glu Cys
            255                 260                 265 atc gag gac ttg ctt aac gag cct ggg caa cct ttg gac ttg agc tgt    867
Ile Glu Asp Leu Leu Asn Glu Pro Gly Gln Pro Leu Asp Leu Ser Cys
270                 275                 280 aaa cgc ccc agg cca taactcgag                                      891
Lys Arg Pro Arg Pro
285

<210> SEQ ID NO 41
<211> LENGTH: 891
<212> TYPE: DNA
<213> ORGANISM: Human adenovirus type 5
<220> FEATURE:
<221> NAME/KEY: CDS
<222> LOCATION: (16)..(882)

<400> SEQUENCE: 41
aagcttgccg ccacc atg aga cat att atc tgc cac gga ggt gtt att acc    51
                 Met Arg His Ile Ile Cys His Gly Gly Val Ile Thr
                  1               5                  10 gaa gaa atg gcc gcc agt ctt ttg gac cag ctg atc gaa gag gta ctg    99
Glu Glu Met Ala Ala Ser Leu Leu Asp Gln Leu Ile Glu Glu Val Leu
            15                  20                  25 gct gat aat ctt cca cct cct agc cat ttt gaa cca cct acc ctt cac   147
Ala Asp Asn Leu Pro Pro Pro Ser His Phe Glu Pro Pro Thr Leu His
        30                  35                  40
```

```
gaa ctg cat gat tta gac gtg acg gcc ccc gaa gat ccc aac gag gag      195
Glu Leu His Asp Leu Asp Val Thr Ala Pro Glu Asp Pro Asn Glu Glu
 45              50                  55                  60 gcg gtt tcg cag att ttt ccc gac tct gta atg ttg gcg gtg cag gaa      243
Ala Val Ser Gln Ile Phe Pro Asp Ser Val Met Leu Ala Val Gln Glu
                 65                  70                  75 ggg att gac tta ctc act ttt ccg ccg gcg ccc ggt tct ccg gag ccg      291
Gly Ile Asp Leu Leu Thr Phe Pro Pro Ala Pro Gly Ser Pro Glu Pro
             80                  85                  90 cct cac ctt tcc cgg cag ccc gag cag ccg gag cag aga gcc ttg ggt      339
Pro His Leu Ser Arg Gln Pro Glu Gln Pro Glu Gln Arg Ala Leu Gly
         95                 100                 105 ccg gtt tct atg cca aac ctt gta ccg gag gtg atc gat ctt acc tgc      387
Pro Val Ser Met Pro Asn Leu Val Pro Glu Val Ile Asp Leu Thr Cys
     110                 115                 120 cac gag gct ggc ttt cca ccc agt gac gac gag gat gaa gag ggt gag      435
His Glu Ala Gly Phe Pro Pro Ser Asp Asp Glu Asp Glu Glu Gly Glu
125                 130                 135                 140 gag ttt gtg tta gat tat gtg gag cac ccc ggg cac ggt tgc agg tct      483
Glu Phe Val Leu Asp Tyr Val Glu His Pro Gly His Gly Cys Arg Ser
                145                 150                 155 tgt cat tat cac cgg agg aat acg ggg gac cca gat att atg tgt tcg      531
Cys His Tyr His Arg Arg Asn Thr Gly Asp Pro Asp Ile Met Cys Ser
            160                 165                 170 ctt tgc tat atg agg acc tgt ggc atg ttt gtc tac agt cct gtg tct      579
Leu Cys Tyr Met Arg Thr Cys Gly Met Phe Val Tyr Ser Pro Val Ser
        175                 180                 185 gaa cct gag cct gag ccc gag cca gaa ccg gag cct gca aga cct acc      627
Glu Pro Glu Pro Glu Pro Glu Pro Glu Pro Glu Pro Ala Arg Pro Thr
    190                 195                 200 cgc cgt cct aaa atg gcg cct gct atc ctg aga cgc ccg aca tca cct      675
Arg Arg Pro Lys Met Ala Pro Ala Ile Leu Arg Arg Pro Thr Ser Pro
205                 210                 215                 220 gtg tct aga gaa tgc aat agt agt acg gat agc tgt gac tcc ggt cct      723
Val Ser Arg Glu Cys Asn Ser Ser Thr Asp Ser Cys Asp Ser Gly Pro
                225                 230                 235 tct aac aca cct cct gag ata cac ccg gtg gtc ccg ctg tgc ccc att      771
Ser Asn Thr Pro Pro Glu Ile His Pro Val Val Pro Leu Cys Pro Ile
            240                 245                 250 aaa cca gtt gcc gtg aga gtt ggt ggg cgt cgc cag gct gtg gaa tgt      819
Lys Pro Val Ala Val Arg Val Gly Gly Arg Arg Gln Ala Val Glu Cys
        255                 260                 265 atc gag gac ttg ctt aac gag cct ggg caa cct ttg gac ttg agc tgt      867
Ile Glu Asp Leu Leu Asn Glu Pro Gly Gln Pro Leu Asp Leu Ser Cys
    270                 275                 280 aaa cgc ccc agg cca taactcgag                                        891
Lys Arg Pro Arg Pro
285

<210> SEQ ID NO 42
<211> LENGTH: 1047
<212> TYPE: DNA
<213> ORGANISM: Cricetulus longicaudatus
<220> FEATURE:
<221> NAME/KEY: CDS
<222> LOCATION: (16)..(1038)

<400> SEQUENCE: 42
aagcttgccg ccacc atg acc atg gaa tct gga gca gac aac cag cag agt       51
                Met Thr Met Glu Ser Gly Ala Asp Asn Gln Gln Ser
                 1               5                  10
```

```
gga gat gct gct gta aca gaa gct gaa aat caa caa atg aca gct caa      99
Gly Asp Ala Ala Val Thr Glu Ala Glu Asn Gln Gln Met Thr Ala Gln
        15                  20                  25 gcc caa cca cag att gcc aca tta gcc cag gta tcc atg cca gca gct     147
Ala Gln Pro Gln Ile Ala Thr Leu Ala Gln Val Ser Met Pro Ala Ala
    30                  35                  40 cat gcg aca tca tct gct ccc act gta acc tta gtg cag ctg ccc aat     195
His Ala Thr Ser Ser Ala Pro Thr Val Thr Leu Val Gln Leu Pro Asn
45                  50                  55                  60 ggg cag aca gtc caa gtc cat gga gtt att cag gcg gcc cag cca tca     243
Gly Gln Thr Val Gln Val His Gly Val Ile Gln Ala Ala Gln Pro Ser
            65                  70                  75 gtt att cag tct cca caa gtc caa aca gtt cag tct tcc tgt aag gac     291
Val Ile Gln Ser Pro Gln Val Gln Thr Val Gln Ser Ser Cys Lys Asp
        80                  85                  90 tta aaa aga ctt ttc tcc gga act cag att tca act att gca gaa agt     339
Leu Lys Arg Leu Phe Ser Gly Thr Gln Ile Ser Thr Ile Ala Glu Ser
    95                  100                 105 gag gat tca cag gaa tct gtg gat agt gta act gat tcc caa aag cga     387
Glu Asp Ser Gln Glu Ser Val Asp Ser Val Thr Asp Ser Gln Lys Arg
110                 115                 120 agg gaa att ctt tca agg agg cct tcc tac agg aaa att ttg aat gac     435
Arg Glu Ile Leu Ser Arg Arg Pro Ser Tyr Arg Lys Ile Leu Asn Asp
125                 130                 135                 140 tta tct tct gat gca cca ggg gtg cca agg att gaa gaa gaa aag tcg     483
Leu Ser Ser Asp Ala Pro Gly Val Pro Arg Ile Glu Glu Glu Lys Ser
            145                 150                 155 gaa gag gag act tca gcc cct gcc atc acc act gtg aca gtg cca act     531
Glu Glu Glu Thr Ser Ala Pro Ala Ile Thr Thr Val Thr Val Pro Thr
        160                 165                 170 ccg att tac cag aca agc agt ggg cag tat att gcc att acc cag gga     579
Pro Ile Tyr Gln Thr Ser Ser Gly Gln Tyr Ile Ala Ile Thr Gln Gly
    175                 180                 185 gga gct ata cag ctg gct aac aat ggt acc gat ggg gta cag ggc ctt     627
Gly Ala Ile Gln Leu Ala Asn Asn Gly Thr Asp Gly Val Gln Gly Leu
190                 195                 200 cag aca tta acc atg acc aat gca gct gcc act cag ccg ggt acc act     675
Gln Thr Leu Thr Met Thr Asn Ala Ala Ala Thr Gln Pro Gly Thr Thr
205                 210                 215                 220 att cta cag tat gca cag acc act gat gga cag cag att cta gtg ccc     723
Ile Leu Gln Tyr Ala Gln Thr Thr Asp Gly Gln Gln Ile Leu Val Pro
            225                 230                 235 agc aac caa gtt gtt gtt caa gct gcc tct ggc gat gta caa aca tac     771
Ser Asn Gln Val Val Val Gln Ala Ala Ser Gly Asp Val Gln Thr Tyr
        240                 245                 250 caa att cgt aca gca ccc act agc acc atc gcc cct gga gtt gtt atg     819
Gln Ile Arg Thr Ala Pro Thr Ser Thr Ile Ala Pro Gly Val Val Met
    255                 260                 265 gca tcc tcc cca gca ctt cct acg cag cct gct gaa gaa gca gcc cgg     867
Ala Ser Ser Pro Ala Leu Pro Thr Gln Pro Ala Glu Glu Ala Ala Arg
270                 275                 280 aag aga gag gtt cgt cta atg aag aac agg gaa gca gca aga gaa tgt     915
Lys Arg Glu Val Arg Leu Met Lys Asn Arg Glu Ala Ala Arg Glu Cys
285                 290                 295                 300 cgt aga aag aag aaa gaa tat gtg aaa tgt tta gag aac aga gtg gca     963
Arg Arg Lys Lys Lys Glu Tyr Val Lys Cys Leu Glu Asn Arg Val Ala
            305                 310                 315
```

```
gtg ctt gaa aac caa aac aag aca ttg att gag gag cta aaa gca ctt        1011
Val Leu Glu Asn Gln Asn Lys Thr Leu Ile Glu Glu Leu Lys Ala Leu
        320                 325                 330 aag gac ctt tac tgc cac aaa tca gat taaggatcc                          1047
Lys Asp Leu Tyr Cys His Lys Ser Asp
        335                 340

<210> SEQ ID NO 43
<211> LENGTH: 1047
<212> TYPE: DNA
<213> ORGANISM: Cricetulus longicaudatus
<220> FEATURE:
<221> NAME/KEY: CDS
<222> LOCATION: (16)..(1038)

<400> SEQUENCE: 43
aagcttgccg ccacc atg acc atg gaa tct gga gca gac aac cag cag agt         51
                Met Thr Met Glu Ser Gly Ala Asp Asn Gln Gln Ser
                  1               5                  10 gga gat gct gct gta aca gaa gct gaa aat caa caa atg aca gct caa         99
Gly Asp Ala Ala Val Thr Glu Ala Glu Asn Gln Gln Met Thr Ala Gln
        15                  20                  25 gcc caa cca cag att gcc aca tta gcc cag gta tcc atg cca gca gct        147
Ala Gln Pro Gln Ile Ala Thr Leu Ala Gln Val Ser Met Pro Ala Ala
    30                  35                  40 cat gcg aca tca tct gct ccc act gta acc tta gtg cag ctg ccc aat        195
His Ala Thr Ser Ser Ala Pro Thr Val Thr Leu Val Gln Leu Pro Asn
45                  50                  55                  60 ggg cag aca gtc caa gtc cat gga gtt att cag gcg gcc cag cca tca        243
Gly Gln Thr Val Gln Val His Gly Val Ile Gln Ala Ala Gln Pro Ser
                65                  70                  75 gtt att cag tct cca caa gtc caa aca gtt cag tct tcc tgt aag gac        291
Val Ile Gln Ser Pro Gln Val Gln Thr Val Gln Ser Ser Cys Lys Asp
            80                  85                  90 tta aaa aga ctt ttc tcc gga act cag att tca act att gca gaa agt        339
Leu Lys Arg Leu Phe Ser Gly Thr Gln Ile Ser Thr Ile Ala Glu Ser
        95                 100                 105 gag gat tca cag gaa tct gtg gat agt gta act gat tcc caa aag cga        387
Glu Asp Ser Gln Glu Ser Val Asp Ser Val Thr Asp Ser Gln Lys Arg
    110                 115                 120 agg gaa att ctt tca agg agg cct tcc tcc agg aaa att ttg aat gac        435
Arg Glu Ile Leu Ser Arg Arg Pro Ser Ser Arg Lys Ile Leu Asn Asp
125                 130                 135                 140 tta tct tct gat gca cca ggg gtg cca agg att gaa gaa gaa aag tcg        483
Leu Ser Ser Asp Ala Pro Gly Val Pro Arg Ile Glu Glu Glu Lys Ser
                145                 150                 155 gaa gag gag act tca gcc cct gcc atc acc act gtg aca gtg cca act        531
Glu Glu Glu Thr Ser Ala Pro Ala Ile Thr Thr Val Thr Val Pro Thr
            160                 165                 170 ccg att tac cag aca agc agt ggg cag tat att gcc att acc cag gga        579
Pro Ile Tyr Gln Thr Ser Ser Gly Gln Tyr Ile Ala Ile Thr Gln Gly
        175                 180                 185 gga gct ata cag ctg gct aac aat ggt acc gat ggg gta cag ggc ctt        627
Gly Ala Ile Gln Leu Ala Asn Asn Gly Thr Asp Gly Val Gln Gly Leu
    190                 195                 200 cag aca tta acc atg acc aat gca gct gcc act cag ccg ggt acc act        675
Gln Thr Leu Thr Met Thr Asn Ala Ala Ala Thr Gln Pro Gly Thr Thr
205                 210                 215                 220 att cta cag tat gca cag acc act gat gga cag cag att cta gtg ccc        723
Ile Leu Gln Tyr Ala Gln Thr Thr Asp Gly Gln Gln Ile Leu Val Pro
                225                 230                 235
```

| | | | | | | | | | | | | | | | | |
|---|---|---|---|---|---|---|---|---|---|---|---|---|---|---|---|---|
| agc | aac | caa | gtt | gtt | gtt | caa | gct | gcc | tct | ggc | gat | gta | caa | aca | tac | 771 |
| Ser | Asn | Gln | Val | Val | Val | Gln | Ala | Ala | Ser | Gly | Asp | Val | Gln | Thr | Tyr | |
| | | 240 | | | | | 245 | | | | | 250 | | | | |

| | | | | | | | | | | | | | | | | |
|---|---|---|---|---|---|---|---|---|---|---|---|---|---|---|---|---|
| caa | att | cgt | aca | gca | ccc | act | agc | acc | atc | gcc | cct | gga | gtt | gtt | atg | 819 |
| Gln | Ile | Arg | Thr | Ala | Pro | Thr | Ser | Thr | Ile | Ala | Pro | Gly | Val | Val | Met | |
| | | 255 | | | | | 260 | | | | | 265 | | | | |

| | | | | | | | | | | | | | | | | |
|---|---|---|---|---|---|---|---|---|---|---|---|---|---|---|---|---|
| gca | tcc | tcc | cca | gca | ctt | cct | acg | cag | cct | gct | gaa | gaa | gca | gcc | cgg | 867 |
| Ala | Ser | Ser | Pro | Ala | Leu | Pro | Thr | Gln | Pro | Ala | Glu | Glu | Ala | Ala | Arg | |
| 270 | | | | | 275 | | | | | 280 | | | | | | |

| | | | | | | | | | | | | | | | | |
|---|---|---|---|---|---|---|---|---|---|---|---|---|---|---|---|---|
| aag | aga | gag | gtt | cgt | cta | atg | aag | aac | agg | gaa | gca | gca | aga | gaa | tgt | 915 |
| Lys | Arg | Glu | Val | Arg | Leu | Met | Lys | Asn | Arg | Glu | Ala | Ala | Arg | Glu | Cys | |
| 285 | | | | | 290 | | | | | 295 | | | | | 300 | |

| | | | | | | | | | | | | | | | | |
|---|---|---|---|---|---|---|---|---|---|---|---|---|---|---|---|---|
| cgt | aga | aag | aag | aaa | gaa | tat | gtg | aaa | tgt | tta | gag | aac | aga | gtg | gca | 963 |
| Arg | Arg | Lys | Lys | Lys | Glu | Tyr | Val | Lys | Cys | Leu | Glu | Asn | Arg | Val | Ala | |
| | | | | 305 | | | | | 310 | | | | | 315 | | |

| | | | | | | | | | | | | | | | | |
|---|---|---|---|---|---|---|---|---|---|---|---|---|---|---|---|---|
| gtg | ctt | gaa | aac | caa | aac | aag | aca | ttg | att | gag | gag | cta | aaa | gca | ctt | 1011 |
| Val | Leu | Glu | Asn | Gln | Asn | Lys | Thr | Leu | Ile | Glu | Glu | Leu | Lys | Ala | Leu | |
| | | 320 | | | | | 325 | | | | | 330 | | | | |

| | | | | | | | | | |
|---|---|---|---|---|---|---|---|---|---|
| aag | gac | ctt | tac | tgc | cac | aaa | tca | gat | taaggatcc | 1047 |
| Lys | Asp | Leu | Tyr | Cys | His | Lys | Ser | Asp | | |
| | | 335 | | | | | 340 | | | |

<210> SEQ ID NO 44
<211> LENGTH: 564
<212> TYPE: DNA
<213> ORGANISM: Human adenovirus type 5
<220> FEATURE:
<221> NAME/KEY: CDS
<222> LOCATION: (28)..(555)

<400> SEQUENCE: 44

| | | | | | | | | | | | | | |
|---|---|---|---|---|---|---|---|---|---|---|---|---|---|
| aagcttactg | ttggtaaagc | cgccacc | atg | gag | gct | tgg | gag | tgt | ttg | gaa | gat | | 54 |
| | | | Met | Glu | Ala | Trp | Glu | Cys | Leu | Glu | Asp | | |
| | | | 1 | | | | 5 | | | | | | |

| | | | | | | | | | | | | | | | | |
|---|---|---|---|---|---|---|---|---|---|---|---|---|---|---|---|---|
| ttt | tct | gct | gtg | cgt | aac | ttg | ctg | gaa | cag | agc | tct | aac | agt | acc | tct | 102 |
| Phe | Ser | Ala | Val | Arg | Asn | Leu | Leu | Glu | Gln | Ser | Ser | Asn | Ser | Thr | Ser | |
| 10 | | | | | 15 | | | | | 20 | | | | | 25 | |

| | | | | | | | | | | | | | | | | |
|---|---|---|---|---|---|---|---|---|---|---|---|---|---|---|---|---|
| tgg | ttt | tgg | agg | ttt | ctg | tgg | ggc | tca | tcc | cag | gca | aag | tta | gtc | tgc | 150 |
| Trp | Phe | Trp | Arg | Phe | Leu | Trp | Gly | Ser | Ser | Gln | Ala | Lys | Leu | Val | Cys | |
| | | | | 30 | | | | | 35 | | | | | 40 | | |

| | | | | | | | | | | | | | | | | |
|---|---|---|---|---|---|---|---|---|---|---|---|---|---|---|---|---|
| aga | att | aag | gag | gat | tac | aag | tgg | gaa | ttt | gaa | gag | ctt | ttg | aaa | tcc | 198 |
| Arg | Ile | Lys | Glu | Asp | Tyr | Lys | Trp | Glu | Phe | Glu | Glu | Leu | Leu | Lys | Ser | |
| | | 45 | | | | | 50 | | | | | 55 | | | | |

| | | | | | | | | | | | | | | | | |
|---|---|---|---|---|---|---|---|---|---|---|---|---|---|---|---|---|
| tgt | ggt | gag | ctg | ttt | gat | tct | ttg | aat | ctg | ggt | cac | cag | gcg | ctt | ttc | 246 |
| Cys | Gly | Glu | Leu | Phe | Asp | Ser | Leu | Asn | Leu | Gly | His | Gln | Ala | Leu | Phe | |
| | | 60 | | | | | 65 | | | | | 70 | | | | |

| | | | | | | | | | | | | | | | | |
|---|---|---|---|---|---|---|---|---|---|---|---|---|---|---|---|---|
| caa | gag | aag | gtc | atc | aag | act | ttg | gat | ttt | tcc | aca | ccg | ggg | cgc | gct | 294 |
| Gln | Glu | Lys | Val | Ile | Lys | Thr | Leu | Asp | Phe | Ser | Thr | Pro | Gly | Arg | Ala | |
| 75 | | | | | 80 | | | | | 85 | | | | | | |

| | | | | | | | | | | | | | | | | |
|---|---|---|---|---|---|---|---|---|---|---|---|---|---|---|---|---|
| gcg | gct | gct | gtt | gct | ttt | ttg | agt | ttt | ata | aag | gat | aaa | tgg | agc | gaa | 342 |
| Ala | Ala | Ala | Val | Ala | Phe | Leu | Ser | Phe | Ile | Lys | Asp | Lys | Trp | Ser | Glu | |
| 90 | | | | | 95 | | | | | 100 | | | | | 105 | |

| | | | | | | | | | | | | | | | | |
|---|---|---|---|---|---|---|---|---|---|---|---|---|---|---|---|---|
| gaa | acc | cat | ctg | agc | ggg | ggg | tac | ctg | ctg | gat | ttt | ctg | gcc | atg | cat | 390 |
| Glu | Thr | His | Leu | Ser | Gly | Gly | Tyr | Leu | Leu | Asp | Phe | Leu | Ala | Met | His | |
| | | | | 110 | | | | | 115 | | | | | 120 | | |

| | | | | | | | | | | | | | | | | |
|---|---|---|---|---|---|---|---|---|---|---|---|---|---|---|---|---|
| ctg | tgg | aga | gcg | gtt | gtg | aga | cac | aag | aat | cgc | ctg | cta | ctg | ttg | tct | 438 |
| Leu | Trp | Arg | Ala | Val | Val | Arg | His | Lys | Asn | Arg | Leu | Leu | Leu | Leu | Ser | |
| | | | | 125 | | | | | 130 | | | | | 135 | | |

| | | | | | | | | | | | | | | | | |
|---|---|---|---|---|---|---|---|---|---|---|---|---|---|---|---|---|
| tcc | gtc | cgc | ccg | gcg | ata | ata | ccg | acg | gag | gag | cag | cag | cag | cag | cag | 486 |
| Ser | Val | Arg | Pro | Ala | Ile | Ile | Pro | Thr | Glu | Glu | Gln | Gln | Gln | Gln | Gln | |
| | | 140 | | | | | 145 | | | | | 150 | | | | |

```
gag gaa gcc agg cgg cgg cgg cag gag cag agc cca tgg aac ccg aga      534
Glu Glu Ala Arg Arg Arg Arg Gln Glu Gln Ser Pro Trp Asn Pro Arg
    155                 160                 165 gcc ggc ctg gac cct cgg gaa tgatctaga                                564
Ala Gly Leu Asp Pro Arg Glu
170             175

<210> SEQ ID NO 45
<211> LENGTH: 596
<212> TYPE: DNA
<213> ORGANISM: Cricetulus longicaudatus
<220> FEATURE:
<221> NAME/KEY: CDS
<222> LOCATION: (3)..(587)

<400> SEQUENCE: 45 cc atg gct caa gct ggg aga aca ggg tat gat aac cga gag atc gtg       47
   Met Ala Gln Ala Gly Arg Thr Gly Tyr Asp Asn Arg Glu Ile Val
   1               5                   10                  15 atg aag tac atc cat tat aag ctg tca cag agg ggc tac gag tgg gat      95
Met Lys Tyr Ile His Tyr Lys Leu Ser Gln Arg Gly Tyr Glu Trp Asp
                20                  25                  30 gtg gga gat gtg gac gcc gcg gcc gcg gcc gcg agc ccc gtg cca cct     143
Val Gly Asp Val Asp Ala Ala Ala Ala Ala Ala Ser Pro Val Pro Pro
        35                  40                  45 gtg gtc cac ctg acc ctc cgc cgg gct ggg gat gac ttc tcc cgt cgc     191
Val Val His Leu Thr Leu Arg Arg Ala Gly Asp Asp Phe Ser Arg Arg
    50                  55                  60 tac cgt cgc gac ttc gcg gag atg tcc agt cag ctg cac ctg acg ccc     239
Tyr Arg Arg Asp Phe Ala Glu Met Ser Ser Gln Leu His Leu Thr Pro
65                  70                  75 ttc acc gcg agg gga cgc ttt gct acg gtg gtg gag gaa ctc ttc agg     287
Phe Thr Ala Arg Gly Arg Phe Ala Thr Val Val Glu Glu Leu Phe Arg
80                  85                  90                  95 gat ggg gtg aac tgg ggg agg att gtg gcc ttc ttt gag ttc ggt ggg     335
Asp Gly Val Asn Trp Gly Arg Ile Val Ala Phe Phe Glu Phe Gly Gly
                100                 105                 110 gtc atg tgt gtg gag agc gtc aac agg gag atg tca ccc ctg gtg gac     383
Val Met Cys Val Glu Ser Val Asn Arg Glu Met Ser Pro Leu Val Asp
            115                 120                 125 aac atc gcc ctg tgg atg acc gag tac ctg aac cgg cat ctg cac acc     431
Asn Ile Ala Leu Trp Met Thr Glu Tyr Leu Asn Arg His Leu His Thr
        130                 135                 140 tgg atc cag gat aac gga ggc tgg gac gca ttt gtg gaa ctg tac ggc     479
Trp Ile Gln Asp Asn Gly Gly Trp Asp Ala Phe Val Glu Leu Tyr Gly
    145                 150                 155 ccc agt gtg agg cct ctg ttt gat ttc tct tgg ctg tct ctg aag acc     527
Pro Ser Val Arg Pro Leu Phe Asp Phe Ser Trp Leu Ser Leu Lys Thr
160                 165                 170                 175 ctg ctc agc ctg gcc ctg gtc ggg gcc tgc atc act ctg ggt acc tac     575
Leu Leu Ser Leu Ala Leu Val Gly Ala Cys Ile Thr Leu Gly Thr Tyr
                180                 185                 190 ctg ggc cac aag tgatctaga                                            596
Leu Gly His Lys
            195

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 46
cgcagtacta gtttatggcc tggggcgttt acagctc                                    37

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagctattcc agaagtagtg                                                       20

<210> SEQ ID NO 48
<211> LENGTH: 289
<212> TYPE: PRT
<213> ORGANISM: Human adenovirus type 5

<400> SEQUENCE: 48

Met Arg His Ile Ile Cys His Gly Gly Val Ile Thr Glu Glu Met Ala
1               5                   10                  15

Ala Ser Leu Leu Asp Gln Leu Ile Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Glu Glu Phe Val Leu
    130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
        195                 200                 205

Met Ala Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
        275                 280                 285

Pro
```

-continued

```
<210> SEQ ID NO 49
<211> LENGTH: 289
<212> TYPE: PRT
<213> ORGANISM: Human adenovirus type 5

<400> SEQUENCE: 49

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu His Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Glu Glu Phe Val Leu
    130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
        195                 200                 205

Met Ala Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
        275                 280                 285

Pro

<210> SEQ ID NO 50
<211> LENGTH: 341
<212> TYPE: PRT
<213> ORGANISM: Cricetulus longicaudatus

<400> SEQUENCE: 50

Met Thr Met Glu Ser Gly Ala Asp Asn Gln Gln Ser Gly Asp Ala Ala
1               5                   10                  15

Val Thr Glu Ala Glu Asn Gln Gln Met Thr Ala Gln Ala Gln Pro Gln
            20                  25                  30

Ile Ala Thr Leu Ala Gln Val Ser Met Pro Ala Ala His Ala Thr Ser
        35                  40                  45
```

-continued

```
Ser Ala Pro Thr Val Thr Leu Val Gln Leu Pro Asn Gly Gln Thr Val
    50                  55                  60

Gln Val His Gly Val Ile Gln Ala Ala Gln Pro Ser Val Ile Gln Ser
65                  70                  75                  80

Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
        115                 120                 125

Ser Arg Arg Pro Ser Tyr Arg Lys Ile Leu Asn Asp Leu Ser Ser Asp
    130                 135                 140

Ala Pro Gly Val Pro Arg Ile Glu Glu Lys Ser Glu Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
            180                 185                 190

Leu Ala Asn Asn Gly Thr Asp Gly Val Gln Gly Leu Gln Thr Leu Thr
        195                 200                 205

Met Thr Asn Ala Ala Ala Thr Gln Pro Gly Thr Thr Ile Leu Gln Tyr
    210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
                245                 250                 255

Ala Pro Thr Ser Thr Ile Ala Pro Gly Val Val Met Ala Ser Ser Pro
            260                 265                 270

Ala Leu Pro Thr Gln Pro Ala Glu Glu Ala Arg Lys Arg Glu Val
        275                 280                 285

Arg Leu Met Lys Asn Arg Glu Ala Ala Arg Glu Cys Arg Arg Lys Lys
    290                 295                 300

Lys Glu Tyr Val Lys Cys Leu Glu Asn Arg Val Ala Val Leu Glu Asn
305                 310                 315                 320

Gln Asn Lys Thr Leu Ile Glu Glu Leu Lys Ala Leu Lys Asp Leu Tyr
                325                 330                 335

Cys His Lys Ser Asp
            340

<210> SEQ ID NO 51
<211> LENGTH: 341
<212> TYPE: PRT
<213> ORGANISM: Cricetulus longicaudatus

<400> SEQUENCE: 51

Met Thr Met Glu Ser Gly Ala Asp Asn Gln Gln Ser Gly Asp Ala Ala
1               5                   10                  15

Val Thr Glu Ala Glu Asn Gln Gln Met Thr Ala Gln Ala Gln Pro Gln
            20                  25                  30

Ile Ala Thr Leu Ala Gln Val Ser Met Pro Ala Ala His Ala Thr Ser
        35                  40                  45

Ser Ala Pro Thr Val Thr Leu Val Gln Leu Pro Asn Gly Gln Thr Val
    50                  55                  60

Gln Val His Gly Val Ile Gln Ala Ala Gln Pro Ser Val Ile Gln Ser
65                  70                  75                  80
```

```
Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
        115                 120                 125

Ser Arg Arg Pro Ser Ser Arg Lys Ile Leu Asn Asp Leu Ser Ser Asp
    130                 135                 140

Ala Pro Gly Val Pro Arg Ile Glu Glu Lys Ser Glu Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
            180                 185                 190

Leu Ala Asn Asn Gly Thr Asp Gly Val Gln Gly Leu Gln Thr Leu Thr
        195                 200                 205

Met Thr Asn Ala Ala Ala Thr Gln Pro Gly Thr Thr Ile Leu Gln Tyr
    210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
                245                 250                 255

Ala Pro Thr Ser Thr Ile Ala Pro Gly Val Val Met Ala Ser Ser Pro
            260                 265                 270

Ala Leu Pro Thr Gln Pro Ala Glu Ala Ala Arg Lys Arg Glu Val
        275                 280                 285

Arg Leu Met Lys Asn Arg Glu Ala Ala Arg Glu Cys Arg Arg Lys Lys
    290                 295                 300

Lys Glu Tyr Val Lys Cys Leu Glu Asn Arg Val Ala Val Leu Glu Asn
305                 310                 315                 320

Gln Asn Lys Thr Leu Ile Glu Glu Leu Lys Ala Leu Lys Asp Leu Tyr
                325                 330                 335

Cys His Lys Ser Asp
            340

<210> SEQ ID NO 52
<211> LENGTH: 176
<212> TYPE: PRT
<213> ORGANISM: Human adenovirus type 5

<400> SEQUENCE: 52

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110
```

Tyr Leu Leu Asp Phe Leu Ala Met His Leu Trp Arg Ala Val Val Arg
    115                 120                 125

His Lys Asn Arg Leu Leu Leu Ser Ser Val Arg Pro Ala Ile Ile
    130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
                165                 170                 175

<210> SEQ ID NO 53
<211> LENGTH: 195
<212> TYPE: PRT
<213> ORGANISM: Cricetulus longicaudatus

<400> SEQUENCE: 53

Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Val
                20                  25                  30

Gly Asp Val Asp Ala Ala Ala Ala Ala Ser Pro Val Pro Pro Val
            35                  40                  45

Val His Leu Thr Leu Arg Arg Ala Gly Asp Asp Phe Ser Arg Arg Tyr
    50                  55                  60

Arg Arg Asp Phe Ala Glu Met Ser Ser Gln Leu His Leu Thr Pro Phe
65                  70                  75                  80

Thr Ala Arg Gly Arg Phe Ala Thr Val Val Glu Glu Leu Phe Arg Asp
                85                  90                  95

Gly Val Asn Trp Gly Arg Ile Val Ala Phe Phe Glu Phe Gly Gly Val
            100                 105                 110

Met Cys Val Glu Ser Val Asn Arg Glu Met Ser Pro Leu Val Asp Asn
        115                 120                 125

Ile Ala Leu Trp Met Thr Glu Tyr Leu Asn Arg His Leu His Thr Trp
    130                 135                 140

Ile Gln Asp Asn Gly Gly Trp Asp Ala Phe Val Glu Leu Tyr Gly Pro
145                 150                 155                 160

Ser Val Arg Pro Leu Phe Asp Phe Ser Trp Leu Ser Leu Lys Thr Leu
                165                 170                 175

Leu Ser Leu Ala Leu Val Gly Ala Cys Ile Thr Leu Gly Thr Tyr Leu
            180                 185                 190

Gly His Lys
    195

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Val Leu Thr Arg
1               5

<210> SEQ ID NO 55
<211> LENGTH: 5
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 55

Gly Gly Gly Gly Ser
1               5

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Met Ala Tyr Pro Asp Tyr Val Pro Asp Tyr Ala Val
1               5                   10
```